US008744778B2

(12) United States Patent
Tan et al.

(10) Patent No.: US 8,744,778 B2
(45) Date of Patent: Jun. 3, 2014

(54) METHODS FOR CHARACTERIZING AGONISTS AND PARTIAL AGONISTS OF TARGET MOLECULES

(75) Inventors: Yejun Tan, Seattle, WA (US); Hongyue Dai, Chestnut Hill, MA (US); Pek Yee Lum, Seattle, WA (US); John Ryan Thompson, Scotch Plains, NJ (US); Joel Peter Berger, Hoboken, NJ (US); Eric Stanley Muise, New York, NY (US); Richard F. Raubertas, Essex, VT (US); Kenny Kin Chung Wong, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 469 days.

(21) Appl. No.: 13/209,156

(22) Filed: Aug. 12, 2011

(65) Prior Publication Data

US 2011/0294696 A1 Dec. 1, 2011

Related U.S. Application Data

(62) Division of application No. 11/397,327, filed on Apr. 4, 2006, now Pat. No. 8,014,954.

(60) Provisional application No. 60/668,773, filed on Apr. 5, 2005.

(51) Int. Cl.
*G01N 33/48* (2006.01)
*C12Q 1/68* (2006.01)
*G06G 7/58* (2006.01)

(52) U.S. Cl.
USPC ............... 702/19; 702/20; 435/6.1; 435/6.12; 435/6.13

(58) Field of Classification Search
None
See application file for complete search history.

(56) References Cited

U.S. PATENT DOCUMENTS 6,294,559 B1 9/2001 Smith

FOREIGN PATENT DOCUMENTS

| WO | 9937817 A1 | 7/1999 |
|---|---|---|
| WO | 02059560 A2 | 8/2002 |

*Primary Examiner* — Michael Borin
(74) *Attorney, Agent, or Firm* — Christensen O'Connor Johnson Kindness PLLC

(57) ABSTRACT

In one aspect, the present invention provides methods of determining whether an agent is more like a partial agonist of a target molecule than a full agonist of the same target molecule. In another aspect, the present invention provides methods to select a candidate compound that may reduce blood plasma glucose concentration in a mammal. Populations of genes are provided that are useful in the practice of the present invention.

4 Claims, 1 Drawing Sheet

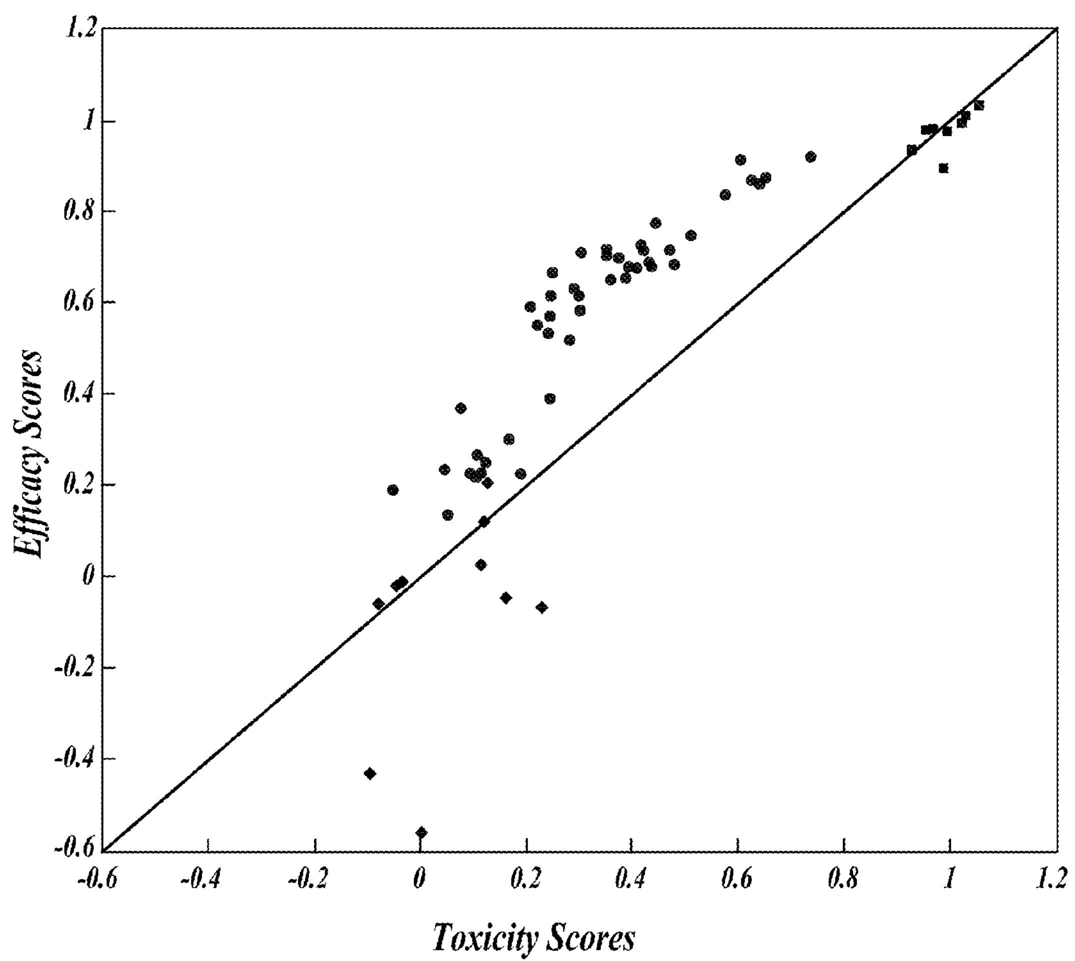
1.2
1
0.8
0.6
0.4
0.2
0
-0.2
-0.4
-0.6
-0.6
-0.4
-0.2
0
0.2
0.4
0.6
0.8
1
1.2
Efficacy Scores
Toxicity Scores

METHODS FOR CHARACTERIZING AGONISTS AND PARTIAL AGONISTS OF TARGET MOLECULES

CROSS-REFERENCE TO RELATED APPLICATION

This application is a division of application Ser. No. 11/397,327, filed Apr. 4, 2006, which claims the benefit of Provisional Application No. 60/668,773, filed Apr. 5, 2005, both of which are herein incorporated by reference.

STATEMENT REGARDING SEQUENCE LISTING

The sequence listing associated with this application is provided in text format in lieu of a paper copy and is hereby incorporated by reference into the specification. The name of the text file containing the sequence listing is 37452SeqFinal.txt. The text file is 96 KB; was created on Aug. 11, 2011; and is being submitted via EFS-Web with the filing of the specification.

FIELD OF THE INVENTION

The present invention relates to methods for screening biologically active agents, such as candidate drug molecules, to identify agents that possess a desired biological activity.

BACKGROUND OF THE INVENTION

Identifying new drug molecules for treating human diseases is a time consuming and expensive process. A candidate drug molecule is usually first identified in a laboratory using an assay for a desired biological activity. The candidate drug is then tested in animals to identify any adverse side effects that might be caused by the drug. This phase of preclinical research and testing may take more than five years. See, e.g., J. A. Zivin, "Understanding Clinical Trials," *Scientific American*, pp. 69-75 (April 2000). The candidate drug is then subjected to extensive clinical testing in humans to determine whether it continues to exhibit the desired biological activity, and whether it induces undesirable, perhaps fatal, side effects. This process may take up to a decade. Id. Adverse effects are often not identified until late in the clinical testing phase when considerable expense has been incurred testing the candidate drug.

For example, an agonist (also referred to as a full agonist) is a chemical substance that binds to a target molecule (e.g., a receptor molecule), in or on a cell, to produce a biochemical and/or physiological effect. A partial agonist is a chemical substance that binds to a target molecule, but does not produce as great a magnitude of a biochemical and/or physiological effect as the agonist. The maximum magnitude of the biochemical and/or physiological effect produced by an agonist of a target molecule cannot be produced by a partial agonist of the same target molecule, even by increasing the dosage of the partial agonist. Some agonists of a target molecule are medically useful drugs that typically produce both desirable and undesirable biological effects. In contrast, partial agonists of a target molecule, that are medically useful drugs, often produce a weaker undesirable biological response than does an agonist of the same target molecule. Thus, partial agonists may be better drugs than full agonists because a partial agonist causes a desirable biological effect, and causes little or no undesirable biological effects.

There is a need, therefore, for methods for identifying partial agonists of target molecules that possess a desirable biological activity, and which cause fewer, or less severe, adverse effects than an agonist of the same target molecules.

SUMMARY OF THE INVENTION

In accordance with the foregoing, in one aspect the present invention provides methods for determining whether an agent is more like a partial agonist of a target molecule than a full agonist of the same target molecule. The methods of the invention thereby facilitate identification of partial agonists that may be medically useful drugs having limited undesirable side effects compared to a full agonist of the same target molecule. As described more fully herein, the methods of this aspect of the invention compare the expression of populations of genes in response to an agent to determine whether the agent is more like a partial agonist of a target molecule than a full agonist of the same target molecule.

Accordingly, in one aspect, the present invention provides methods for determining whether an agent is more like a partial agonist of a target molecule than a full agonist of the same target molecule. The methods each include the steps of (a) comparing the magnitude of gene expression of a first population of genes, in a cell type, in response to an agent, to the magnitude of gene expression of the first population of genes, in the cell type, in response to a full agonist of a target molecule, to produce a first comparison result, wherein the first comparison result is represented by a first numerical value; (b) comparing the magnitude of gene expression of a second population of genes, in a cell type, in response to the agent to the magnitude of gene expression of the second population of genes, in the cell type, in response to the full agonist of the target molecule, to produce a second comparison result, wherein the second comparison result is represented by a second numerical value; and (c) using the first numerical value and the second numerical value to determine whether the agent is more like a partial agonist of the target molecule than the full agonist of the target molecule, wherein any part of step (a) can occur before, during, or after any part of step (b). The methods of this aspect of the invention are useful, for example, for determining whether an agent (e.g., chemical compound) induces a biological response in a living thing that is more like the biological response induced in the living thing by a partial agonist of a target molecule(e.g., a receptor, such as a PPARγ molecule described more fully herein) than the biological response induced in the living thing by a full agonist of the target molecule (e.g., PPARγ). The methods of this aspect of the present invention are dose-independent.

In another aspect, the present invention provides methods to screen compounds to identify a candidate compound that may reduce blood plasma glucose concentration in a mammal (e.g., a human being). The methods of this aspect of the invention each include the step of contacting a cell of a cell type with a compound and determining whether the compound causes a significant increase in the level of expression of a population of 29 genes that each hybridize under stringent conditions to a different member of the group of nucleic acid molecules consisting of SEQ ID NOS:1-29, wherein if the compound causes a significant increase in the level of expression of the population of 29 genes then the compound is selected as a candidate compound that may reduce blood plasma glucose concentration in a mammal. SEQ ID NOS:1-29 are cDNA molecules that correspond to 29 different genes as described herein. The methods of this aspect of the invention are useful, for example, for selecting partial agonists of PPARγ that reduce blood plasma glucose concentration in a mammal.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

The FIGURE shows a graph of gene score 1 (GS1) versus gene score 2 (GS2) for several partial and full agonists of PPARγ, as described in Example 2.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual,* 2d ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

In one aspect, the present invention provides methods for determining whether an agent is more like a partial agonist of a target molecule than a full agonist of the same target molecule. The methods of the present invention permit comparison of the magnitudes of expression levels of populations of genes in a living thing to determine whether an agent is more like a partial agonist of a target molecule than a full agonist of the same target molecule. The methods each include the steps of (a) comparing the magnitude of gene expression of a first population of genes, in cells of a cell type, in response to an agent to the magnitude of gene expression of the first population of genes, in cells of the cell type, in response to a full agonist of a target molecule, to produce a first comparison result, wherein the first comparison result is represented by a first numerical value; (b) comparing the magnitude of gene expression of a second population of genes, in cells of the cell type, in response to the agent to the magnitude of gene expression of the second population of genes, in cells of the cell type, in response to the full agonist of the target molecule, to produce a second comparison result, wherein the second comparison result is represented by a second numerical value; and (c) using the first numerical value and the second numerical value to determine whether the agent is more like a partial agonist of the target molecule than the full agonist of the target molecule, wherein any part of step (a) can occur before, during, or after any part of step (b).

The methods of this aspect of the present invention are dose-independent (i.e., in the practice of the methods it is not necessary to use the same dose, or a comparable dose based on $EC_{50}$, of the agent and the full agonist of the target molecule in order to determine whether the agent is more like a partial agonist of the target molecule than the full agonist of the same target molecule). Thus, for example, the methods of the present invention are particularly useful for high-throughput screening of numerous candidate drug molecules because it is not necessary to determine the $EC_{50}$ of each test compound, and to match the dosage of each test compound to the dosage of the reference compound(s) so that comparable $EC_{50}$s of the candidate and reference compounds are used. An additional advantage of the methods of this aspect of the present invention is that it is not necessary to identify compound-specific signature genes, or proteins, to practice the methods of this aspect of the present invention.

As used herein, the term "agent" encompasses any physical, chemical, or energetic agent that induces a biological response in a living organism in vivo and/or in vitro. Thus, for example, the term "agent" encompasses chemical molecules, such as therapeutic molecules, or candidate therapeutic molecules, that may be useful for treating one or more diseases in a living organism, such as in a mammal (e.g., a human being). The term "agent" also encompasses energetic stimuli, such as ultraviolet light. The term "agent" also encompasses physical stimuli, such as forces applied to living cells (e.g., pressure, stretching or shear forces).

For example, the methods of the present invention can be used to determine whether an agent is more like a full agonist or a partial agonist of a target molecule (e.g., a receptor molecule). A full agonist is a chemical substance that binds to a target molecule, in or on a cell, to produce a biochemical and/or physiological effect. A partial agonist also binds to a target molecule, but does not produce as great a magnitude of a biochemical or physiological effect as the full agonist. The maximum magnitude of the biochemical and/or physiological effect produced by a full agonist of a target molecule cannot be produced by a partial agonist of the same target molecule, even by increasing the dosage of the partial agonist.

An example of a receptor molecule is the peroxisome proliferator-activated receptor gamma (hereinafter referred to as PPARγ). A family of structurally and functionally related PPARγs exists in mammals. PPARγs are nuclear hormone receptors, activated by fatty acids, and their eicosanoid metabolites, and by some synthetic compounds, such as the thiazolidinedione (abbreviated as TZD) class of compounds. PPARγs play an important physiological role in metabolism, maintenance of cellular energy homeostasis, and cellular differentiation. Two members of the TZD class of compounds (rosiglitazone and pioglitazone) are PPARγ agonists that reduce hyperglycemia in type 2 diabetes patients. See, e.g., J. L. Oberfield et al., *Proc. Nat'l Acad. Sci. U.S.A.* 96:6102-6106 (1999). In spite of their significant antidiabetic activity, however, the use of TZDs has been limited by adverse side-effects, such as plasma volume expansion and weight gain. Thus, there is a need to identify other ligands that bind to PPARγs and that have desirable biological effects (e.g., reducing blood plasma glucose concentration) but that do not have significant adverse biological effects.

Contacting a Living Cell with an Agent:

In the practice of the present invention comparisons are made between populations of genes that are expressed in at least one living cell (typically in multiple living cells) of a cell type. For ease of description, the use of multiple living cells will be described, although it will be understood that the following description also applies to the use of a single living cell of a cell type. The living cells of the cell type are contacted with an agent before the comparisons are made between populations of genes that are expressed in the living cells.

The living cells can be any type of living cell (e.g., prokaryotic cell or eukaryotic cell, including animal cell and plant cell), although typically the living cells are mammalian cells. In order to be useful in the practice of the present invention, the living cells must include sufficient target molecules (e.g., PPARγ receptors) to provide a measurable response to an agonist, or partial agonist, of the target molecules. The living cells can be cultured in vitro, or can be living cells in vivo. Typically, numerous living cells (e.g., a population of cells cultured in vitro, or a multiplicity of living cells that exist within a living tissue, organ or organism) are contacted with an agent.

An example of a method for contacting living cells, cultured in vitro, with a chemical agent is addition of the agent to the medium in which the living cells are cultured. Examples of methods for contacting living cells, in vivo, with an agent is injection into the bloodstream, or injection into a target tissue or organ, or nasal administration of the agent, or transdermal administration of the agent, or use of a drug delivery device that is implanted into the body of a living subject and which gradually releases the agent into the living body.

First Population of Genes and Second Population of Genes:

the present invention provides methods for determining whether an agent is more like a partial agonist of a target molecule than a full agonist of the same target molecule. The methods of the present invention use a first population of genes. Each member of the first population of genes is selected from a population of regulated genes wherein each gene is regulated by a partial agonist of a target molecule, and also by a full agonist of the same target molecule. The population of regulated genes only includes genes that are regulated in the same direction by the partial agonist and by the full agonist (i.e., only genes that are either upregulated by both the full and partial agonist, or genes that are downregulated by both the full and partial agonist are present in the population of regulated genes).

With respect to each member of the first population of genes, the ratio of the magnitude of regulation of the gene by a partial agonist of a target molecule to the magnitude of regulation of the gene by a full agonist of the same target molecule is consistently greater than the same ratio (magnitude of regulation by the partial agonist/magnitude of regulation by the full agonist) for any of the regulated genes that are not included in the first population of genes.

An example of a first population of genes is an efficacy-related population of genes. As used herein, the phrase "efficacy-related population of genes" refers to a population of genes, present in a living thing, that yields at least one expression pattern, in response to a full agonist of a target molecule, and in response to a partial agonist of the target molecule, that correlates (positively or negatively) with the presence of at least one desired biological response caused by the full or partial agonist in the living thing. By way of example, SEQ ID NOS:1-29 are cDNA molecules that correspond to a population of 29 different efficacy-related genes as described herein. It will be understood that SEQ ID NOS:1-29 are cDNA sequences, and that the expression of the corresponding gene transcripts (e.g., mRNA molecules) are analyzed in the practice of the present invention.

The methods of the present invention also use a second population of genes. Each member of the second population of genes is selected from a population of regulated genes wherein each gene is regulated by a partial agonist of a target molecule, and also by a full agonist of the same target molecule. The population of regulated genes only includes genes that are regulated in the same direction by the partial agonist and by the full agonist (i.e., only genes that are either upregulated by both the full and partial agonist, or genes that are downregulated by both the full and partial agonist are present in the population of regulated genes).

With respect to each member of the second population of genes, the ratio of the magnitude of regulation of the gene by a partial agonist of a target molecule to the magnitude of regulation of the gene by a full agonist of the same target molecule is consistently lower than the same ratio (magnitude of regulation by the partial agonist/magnitude of regulation by the full agonist) for any of the regulated genes that are not included in the second population of genes.

An example of a second population of genes is a toxicity-related population of genes. As used herein, the phrase "toxicity-related population of genes" refers to a population of genes, present in a living thing, that yields at least one expression pattern, in response to a full agonist of a target molecule, and in response to a partial agonist of the target molecule, that correlates (positively or negatively) with the presence of at least one undesirable biological response caused by the full or partial agonist in the living thing. By way of example, SEQ ID NOS:30-40 are cDNA molecules that correspond to a population of 11 different toxicity-related genes as described herein. It will be understood that SEQ ID NOS:30-40 are cDNA sequences, and that the expression of the corresponding gene transcripts (e.g., mRNA molecules) is analyzed in the practice of the present invention.

The magnitude and/or pattern of expression of a first population of genes and/or second population of genes can be measured, for example, by measuring the magnitude and/or pattern of expression of gene transcripts (e.g., mRNA that is present in total RNA extracted from a living thing, or completely or partially purified mRNA extracted from a living thing), or by measuring the magnitude and/or pattern of expression of proteins encoded by the genes.

Useful first and second populations of genes can be identified by any method, or combination of methods, that permits detection and measurement of the expression of a population of genes (e.g., protein microarrays and/or nucleic acid microarrays). EXAMPLE 1 herein describes a representative procedure for identifying the efficacy-related population of genes that corresponds to SEQ ID NOS:1-29, and for identifying the toxicity-related population of genes that corresponds to SEQ ID NOS:30-40.

Detecting Gene Expression by Measuring Gene Transcript Expression:

In the practice of the present invention, the magnitude of gene expression of a first population of genes, and the magnitude of gene expression of a second population of genes are measured in cells of a cell type that have been contacted with an agent.

Gene expression may be measured, for example, by extracting (and optionally purifying) mRNA from the living thing, and using the mRNA as a template to synthesize cDNA which is then labeled (e.g., with a fluorescent dye) and can be used to measure gene expression. While the following, exemplary, description is directed to embodiments of the invention in which the extracted mRNA is used as a template to synthesize cDNA, which is then labeled, it will be understood that the extracted mRNA can also be used as a template to synthesize cRNA which can then be labeled and can be used to measure gene expression.

RNA molecules useful as templates for cDNA synthesis can be isolated from any organism or part thereof, including organs, tissues, and/or individual cells. Any suitable RNA preparation can be utilized, such as total cellular RNA, or such as cytoplasmic RNA or such as an RNA preparation that is enriched for messenger RNA (mRNA), such as RNA preparations that include greater than 70%, or greater than 80%, or greater than 90%, or greater than 95%, or greater than 99% messenger RNA. Typically, RNA preparations that are enriched for messenger RNA are utilized to provide the RNA template in the practice of the methods of this aspect of the invention. Messenger RNA can be purified in accordance with any art-recognized method, such as by the use of oligo-dT columns (see, e.g., Sambrook et al., 1989, *Molecular*

*Cloning—A Laboratory Manual* (*2nd Ed.*), Vol. 1, Chapter 7, Cold Spring Harbor Laboratory, Cold Spring Harbor, N.Y.).

Total RNA may be isolated from cells by procedures that involve breaking open the cells and, typically, denaturation of the proteins contained therein. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells using guanidinium thiocyanate lysis followed by CsCl centrifugation to separate the RNA from DNA (Chirgwin et al., 1979, *Biochemistry* 18:5294-5299). Messenger RNA may be selected with oligo-dT cellulose (see Sambrook et al., supra). Separation of RNA from DNA can also be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

The sample of total RNA typically includes a multiplicity of different mRNA molecules, each different mRNA molecule having a different nucleotide sequence (although there may be multiple copies of the same mRNA molecule). In a specific embodiment, the mRNA molecules in the RNA sample comprise at least 100 different nucleotide sequences. In other embodiments, the mRNA molecules of the RNA sample comprise at least 500, 1,000, 5,000, 10,000, 20,000, 30,000, 40,000, 50,000, 60,000, 70,000, 80,000, 90,000 or 100,000 different nucleotide sequences. In another specific embodiment, the RNA sample is a mammalian RNA sample, the mRNA molecules of the mammalian RNA sample comprising about 20,000 to 30,000 different nucleotide sequences, or comprising substantially all of the different mRNA sequences that are expressed in the cell(s) from which the mRNA was extracted.

In the context of the present example, cDNA molecules are synthesized that are complementary to the RNA template molecules. Each cDNA molecule is preferably sufficiently long (e.g., at least 50 nucleotides in length) to subsequently serve as a specific probe for the mRNA template from which it was synthesized, or to serve as a specific probe for a DNA sequence that is identical to the sequence of the mRNA template from which the cDNA molecule was synthesized. Individual DNA molecules can be complementary to a whole RNA template molecule, or to a portion thereof. Thus, a population of cDNA molecules is synthesized that includes individual DNA molecules that are each complementary to all, or to a portion, of a template RNA molecule. Typically, at least a portion of the complementary sequence of at least 95% (more typically at least 99%) of the template RNA molecules are represented in the population of cDNA molecules.

Any reverse transcriptase molecule can be utilized to synthesize the cDNA molecules, such as reverse transcriptase molecules derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT). A reverse transcriptase lacking RNaseH activity (e.g., SUPERSCRIPT II™ sold by Stratagene, La Jolla, Calif.) has the advantage that, in the absence of an RNaseH activity, synthesis of second strand cDNA molecules does not occur during synthesis of first strand cDNA molecules. The reverse transcriptase molecule should also preferably be thermostable so that the cDNA synthesis reaction can be conducted at as high a temperature as possible, while still permitting hybridization of any required primer(s) to the RNA template molecules.

The synthesis of the cDNA molecules can be primed using any suitable primer, typically an oligonucleotide in the range of ten to 60 bases in length. Oligonucleotides that are useful for priming the synthesis of the cDNA molecules can hybridize to any portion of the RNA template molecules, including the oligo-dT tail. In some embodiments, the synthesis of the cDNA molecules is primed using a mixture of primers, such as a mixture of primers having random nucleotide sequences. Typically, for oligonucleotide molecules less than 100 bases in length, hybridization conditions are 5° C. to 10° C. below the homoduplex melting temperature (Tm); see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987).

A primer for priming cDNA synthesis can be prepared by any suitable method, such as phosphotriester and phosphodiester methods of synthesis, or automated embodiments thereof. It is also possible to use a primer that has been isolated from a biological source, such as a restriction endonuclease digest. An oligonucleotide primer can be DNA, RNA, chimeric mixtures or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming cDNA synthesis.

An oligonucleotide primer for priming cDNA synthesis can be derived by cleavage of a larger nucleic acid fragment using non-specific nucleic acid cleaving chemicals or enzymes or site-specific restriction endonucleases; or by synthesis by standard methods known in the art, e.g., by use of an automated DNA synthesizer (such as are commercially available from Biosearch, Applied Biosystems, etc.) and standard phosphoramidite chemistry. As examples, phosphorothioate oligonucleotides may be synthesized by the method of Stein et al. (*Nucl. Acids Res.* 16:3209-3221, 1988), methylphosphonate oligonucleotides can be prepared by use of controlled pore glass polymer supports (Sarin et al., 1988, *Proc. Natl. Acad. Sci. U.S.A.* 85:7448-7451).

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined, for example, by examining the oligonucleotide that has been separated on an acrylamide gel, or by measuring the optical density at 260 nm in a spectrophotometer.

After cDNA synthesis is complete, the RNA template molecules can be hydrolyzed, and all, or substantially all (typically more than 99%), of the primers can be removed. Hydrolysis of the RNA template can be achieved, for example, by alkalinization of the solution containing the RNA template (e.g., by addition of an aliquot of a concentrated sodium hydroxide solution). The primers can be removed, for example, by applying the solution containing the RNA template molecules, cDNA molecules, and the primers, to a column that separates nucleic acid molecules on the basis of size. The purified, cDNA molecules, can then, for example, be precipitated and redissolved in a suitable buffer.

The cDNA molecules are typically labeled to facilitate the detection of the cDNA molecules when they are used as a probe in a hybridization experiment, such as a probe used to screen a DNA microarray, to identify an efficacy-related population of genes. The cDNA molecules can be labeled with any useful label, such as a radioactive atom (e.g., $^{32}P$), but typically the cDNA molecules are labeled with a dye. Examples of suitable dyes include fluorophores and chemiluminescers.

By way of example, cDNA molecules can be coupled to dye molecules via aminoallyl linkages by incorporating allylamine-derivatized nucleotides (e.g., allylamine-dATP, allylamine-dCTP, allylamine-dGTP, and/or allylamine-dTTP) into the cDNA molecules during synthesis of the cDNA molecules. The allylamine-derivatized nucleotide(s) can then be coupled, via an aminoallyl linkage, to N-hydroxysuccinimide ester derivatives (NHS derivatives) of dyes (e.g., Cy-NHS, Cy3-NHS and/or Cy5-NHS). Again by way of example, in another embodiment, dye-labeled nucleotides may be incorporated into the cDNA molecules during synthesis of the cDNA molecules, which labels the cDNA molecules directly.

It is also possible to include a spacer (usually 5-16 carbon atoms long) between the dye and the nucleotide, which may improve enzymatic incorporation of the modified nucleotides during synthesis of the cDNA molecules.

In the context of the present example, the labeled cDNA is hybridized to a DNA array that includes hundreds, or thousands, of identified nucleic acid molecules (e.g., cDNA molecules) that correspond to genes that are expressed in the type of cells wherein gene expression is being analyzed. Typically, hybridization conditions used to hybridize the labeled cDNA to a DNA array are no more than 25° C. to 30° C. (for example, 10° C.) below the melting temperature (Tm) of the native duplex of the cDNA that has the lowest melting temperature (see generally, Sambrook et al. *Molecular Cloning: A Laboratory Manual,* 2nd ed., Cold Spring Harbor Press, 1987; Ausubel et al., *Current Protocols in Molecular Biology*, Greene Publishing, 1987). Tm for nucleic acid molecules greater than about 100 bases can be calculated by the formula Tm=81.5+0.41% (G+C)−log(Na+). For oligonucleotide molecules less than 100 bases in length, exemplary hybridization conditions are 5° to 10° C. below Tm.

Preparation of Microarrays.

Nucleic acid molecules can be immobilized on a solid substrate by any art-recognized means. For example, nucleic acid molecules (such as DNA or RNA molecules) can be immobilized to nitrocellulose, or to a synthetic membrane capable of binding nucleic acid molecules, or to a nucleic acid microarray, such as a DNA microarray. A DNA microarray, or chip, is a microscopic array of DNA fragments, such as synthetic oligonucleotides, disposed in a defined pattern on a solid support, wherein they are amenable to analysis by standard hybridization methods (see, Schena, *BioEssays* 18:427, 1996).

The DNA in a microarray may be derived, for example, from genomic or cDNA libraries, from fully sequenced clones, or from partially sequenced cDNAs known as expressed sequence tags (ESTs). Methods for obtaining such DNA molecules are generally known in the art (see, e.g., Ausubel et al. (eds.), 1994, *Current Protocols in Molecular Biology*, Vol. 2, Current Protocols Publishing, New York). Again by way of example, oligonucleotides may be synthesized by conventional methods, such as the methods described herein.

Microarrays can be made in a number of ways, of which several are described below. However produced, microarrays preferably share certain characteristics. The arrays are preferably reproducible, allowing multiple copies of a given array to be produced and easily compared with each other. Preferably the microarrays are small, usually smaller than 5 $cm^2$, and they are made from materials that are stable under nucleic acid hybridization conditions. A given binding site or unique set of binding sites in the microarray should specifically bind the product of a single gene (or a nucleic acid molecule that represents the product of a single gene, such as a cDNA molecule that is complementary to all, or to part, of an mRNA molecule). Although there may be more than one physical binding site (hereinafter "site") per specific gene product, for the sake of clarity the discussion below will assume that there is a single site.

In one embodiment, the microarray is an array of polynucleotide probes, the array comprising a support with at least one surface and typically at least 100 different polynucleotide probes, each different polynucleotide probe comprising a different nucleotide sequence and being attached to the surface of the support in a different location on the surface. For example, the nucleotide sequence of each of the different polynucleotide probes can be in the range of 40 to 80 nucleotides in length. For example, the nucleotide sequence of each of the different polynucleotide probes can be in the range of 50 to 70 nucleotides in length. For example, the nucleotide sequence of each of the different polynucleotide probes can be in the range of 50 to 60 nucleotides in length. In specific embodiments, the array comprises polynucleotide probes of at least 2,000, 4,000, 10,000, 15,000, 20,000, 50,000, 80,000, or 100,000 different nucleotide sequences.

Thus, the array can include polynucleotide probes for most, or all, genes expressed in a cell, tissue, organ or organism. In a specific embodiment, the cell or organism is a mammalian cell or organism. In another specific embodiment, the cell or organism is a human cell or organism. In specific embodiments, the nucleotide sequences of the different polynucleotide probes of the array are specific for at least 50%, at least 75%, at least 80%, at least 85%, at least 90%, at least 95%, or at least 99% of the genes in the genome of the cell or organism. Most preferably, the nucleotide sequences of the different polynucleotide probes of the array are specific for all of the genes in the genome of the cell or organism. In specific embodiments, the polynucleotide probes of the array hybridize specifically and distinguishably to at least 10,000, to at least 20,000, to at least 50,000, to at least 80,000, or to at least 100,000 different polynucleotide sequences. In other specific embodiments, the polynucleotide probes of the array hybridize specifically and distinguishably to at least 90%, at least 95%, or at least 99% of the genes or gene transcripts of the genome of a cell or organism. Most preferably, the polynucleotide probes of the array hybridize specifically and distinguishably to the genes or gene transcripts of the entire genome of a cell or organism.

In specific embodiments, the array has at least 100, at least 250, at least 1,000, or at least 2,500 probes per 1 $cm^2$, preferably all or at least 25% or 50% of which are different from each other. In another embodiment, the array is a positionally addressable array (in that the sequence of the polynucleotide probe at each position is known). In another embodiment, the nucleotide sequence of each polynucleotide probe in the array is a DNA sequence. In another embodiment, the DNA sequence is a single-stranded DNA sequence. The DNA sequence may be, e.g., a cDNA sequence, or a synthetic sequence.

When a cDNA molecule that corresponds to an mRNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) DNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In some embodiments, cDNA molecule populations prepared from RNA from two different cell populations, or tissues, or organs, or whole organisms, are hybridized to the binding sites of the array. A single array can be used to simultaneously screen more than one cDNA sample. For example, in the context of the present invention, a single array can be used to simultaneously screen a cDNA sample prepared from a living thing that has been contacted with an agent (e.g., candidate partial agonist of PPARγ), and the same type of living thing that has not been contacted with the agent. The cDNA molecules in the two samples are differently labeled so that they can be distinguished. In one embodiment, for example, cDNA molecules from a cell population treated with a drug is synthesized using a fluorescein-labeled NTP, and cDNA molecules from a control cell population, not treated with the drug, is synthesized using a rhodamine-labeled NTP. When the two populations of cDNA molecules are mixed and hybridized to the DNA array, the relative intensity of signal from each population of cDNA molecules is determined for each site on the array, and any relative difference in abundance of a particular mRNA detected.

In this representative example, the cDNA molecule population from the drug-treated cells will fluoresce green when the fluorophore is stimulated, and the cDNA molecule population from the untreated cells will fluoresce red. As a result, when the drug treatment has no effect, either directly or indirectly, on the relative abundance of a particular mRNA in a cell, the mRNA will be equally prevalent in treated and untreated cells and red-labeled and green-labeled cDNA molecules will be equally prevalent. When hybridized to the DNA array, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Schena et al., 1995, *Science* 270:467-470, which is incorporated by reference in its entirety for all purposes. An advantage of using cDNA molecules labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA molecules from a single cell, and compare, for example, the absolute amount of a particular mRNA in, e.g., a drug-treated or an untreated cell.

Exemplary microarrays and methods for their manufacture and use are set forth in T. R. Hughes et al., *Nature Biotechnology* 19:342-347 (April 2001), which publication is incorporated herein by reference.

Preparation of Nucleic Acid Molecules for Immobilization on Microarrays.

As noted above, the "binding site" to which a particular, cognate, nucleic acid molecule specifically hybridizes is usually a nucleic acid, or nucleic acid analogue, attached at that binding site. In one embodiment, the binding sites of the microarray are DNA polynucleotides corresponding to at least a portion of some or all genes in an organism's genome. These DNAs can be obtained by, for example, polymerase chain reaction (PCR) amplification of gene segments from genomic DNA, cDNA (e.g., by reverse transcription or RT-PCR), or cloned sequences. Nucleic acid amplification primers are chosen, based on the known sequence of the genes or cDNA, that result in amplification of unique fragments (i.e., fragments that typically do not share more than 10 bases of contiguous identical sequence with any other fragment on the microarray). Computer programs are useful in the design of primers with the required specificity and optimal amplification properties. See, e.g., Oligo version 5.0 (National Biosciences). Typically each gene fragment on the microarray will be between about 50 bp and about 2000 bp, more typically between about 100 bp and about 1000 bp, and usually between about 300 bp and about 800 bp in length.

Nucleic acid amplification methods are well known and are described, for example, in Innis et al., eds., 1990, *PCR Protocols: A Guide to Methods and Applications*, Academic Press Inc., San Diego, Calif., which is incorporated by reference in its entirety for all purposes. Computer controlled robotic systems are useful for isolating and amplifying nucleic acids.

An alternative means for generating the nucleic acid molecules for the microarray is by synthesis of synthetic polynucleotides or oligonucleotides, e.g., using N-phosphonate or phosphoramidite chemistries (e.g., Froehler et al., 1986, *Nucleic Acid Res* 14:5399-5407). Synthetic sequences are typically between about 15 and about 100 bases in length, such as between about 20 and about 50 bases.

In some embodiments, synthetic nucleic acids include non-natural bases, e.g., inosine. Where the particular base in a given sequence is unknown or is polymorphic, a universal base, such as inosine or 5-nitroindole, may be substituted. Additionally, it is possible to vary the charge on the phosphate backbone of the oligonucleotide, for example, by thiolation or methylation, or even to use a peptide rather than a phosphate backbone. The making of such modifications is within the skill of one trained in the art.

As noted above, nucleic acid analogues may be used as binding sites for hybridization. An example of a suitable nucleic acid analogue is peptide nucleic acid (see, e.g., Egholm et al., 1993, *Nature* 365:566-568; see also U.S. Pat. No. 5,539,083).

In another embodiment, the binding (hybridization) sites are made from plasmid or phage clones of genes, cDNAs (e.g., expressed sequence tags), or inserts therefrom (Nguyen et al., 1995, *Genomics* 29:207-209). In yet another embodiment, the polynucleotide of the binding sites is RNA.

Attaching Nucleic Acids to the Solid Support.

The nucleic acids, or analogues, are attached to a solid support, which may be made, for example, from glass, silicon, plastic (e.g., polypropylene, nylon, polyester), polyacrylamide, nitrocellulose, cellulose acetate or other materials. In general, non-porous supports, and glass in particular, are preferred. The solid support may also be treated in such a way as to enhance binding of oligonucleotides thereto, or to reduce non-specific binding of unwanted substances thereto. For example, a glass support may be treated with polylysine or silane to facilitate attachment of oligonucleotides to the slide.

Methods of immobilizing DNA on the solid support may include direct touch, micropipetting (see, e.g., Yershov et al., *Proc. Natl. Acad. Sci. USA* 93(10):4913-4918 (1996)), or the use of controlled electric fields to direct a given oligonucleotide to a specific spot in the array. Oligonucleotides are typically immobilized at a density of 100 to 10,000 oligonucleotides per $cm^2$, such as at a density of about 1000 oligonucleotides per $cm^2$.

A preferred method for attaching the nucleic acids to a surface is by printing on glass plates, as is described generally by Schena et al., 1995, Science 270:467-470. This method is especially useful for preparing microarrays of cDNA. (See also DeRisi et al., 1996, *Nature Genetics* 14:457-460; Shalon et al., 1996, *Genome Res.* 6:639-645; and Schena et al., *Proc. Natl. Acad. Sci. USA* 93(20):10614-19, 1996.)

In an alternative to immobilizing pre-fabricated oligonucleotides onto a solid support, it is possible to synthesize oligonucleotides directly on the support (see, e.g., Maskos et al., *Nucl. Acids Res.* 21:2269-70, 1993; Lipshutz et al., 1999, *Nat. Genet.* 21(1 Suppl):20-4). Methods of synthesizing oligonucleotides directly on a solid support include photolithography (see McGall et al., *Proc. Natl. Acad. Sci.* (*USA*) 93:13555-60, 1996) and piezoelectric printing (Lipshutz et al., 1999, *Nat. Genet.* 21(1 Suppl):20-4).

A high-density oligonucleotide array may be employed. Techniques are known for producing arrays containing thousands of oligonucleotides complementary to defined sequences, at defined locations on a surface using photolithographic techniques for synthesis in situ (see Pease et al., 1994, *Proc. Natl. Acad. Sci. USA* 91:5022-5026; Lockhart et al., 1996, *Nature Biotechnol.* 14:1675-80) or other methods for rapid synthesis and deposition of defined oligonucleotides (Lipshutz et al., 1999, *Nat. Genet.* 21(1 Suppl):20-4.).

In some embodiments, microarrays are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioeletronics* 11:687-690; Blanchard, 1998, in *Synthetic DNA Arrays in Genetic Engineering*, Vol. 20, J. K. Setlow (ed.), Plenum Press, New York at pages 111-123; U.S. Pat. No. 6,028,189 to Blanchard. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

Other methods for making microarrays, e.g., by masking (Maskos and Southern, 1992, *Nuc. Acids Res.* 20:1679-1684), may also be used. In principle, any type of array, for example dot blots on a nylon hybridization membrane (see Sambrook et al., 1989, *Molecular Cloning—A Laboratory Manual* (2d ed.), Vols. 1-3, Cold Spring Harbor Laboratory, Cold Spring Harbor, N.Y.), could be used, although, as will be recognized by those of skill in the art, very small arrays are typically preferred because hybridization volumes will be smaller.

Signal Detection and Data Analysis.

When fluorescently labeled probes are used, the fluorescence emissions at each site of an array can be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Research* 6:639-645, which is incorporated by reference in its entirety for all purposes). In one embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Shalon et al., 1996, Genome Res. 6:639-645 and in other references cited herein. Alternatively, the fiber-optic bundle described by Ferguson et al., 1996, *Nature Biotechnol.* 14:1681-1684, may be used to monitor mRNA abundance levels at a large number of sites simultaneously.

Signals are recorded and may be analyzed by computer, e.g., using a 12 bit analog to digital board. In some embodiments the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration.

The relative abundance of an mRNA in two biological samples is scored as a perturbation and its magnitude determined (i.e., the abundance is different in the two sources of mRNA tested), or as not perturbed (i.e., the relative abundance is the same). Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

By way of example, two samples, each labeled with a different fluor, are hybridized simultaneously to permit differential expression measurements. If neither sample hybridizes to a given spot in the array, no fluorescence will be seen. If only one hybridizes to a given spot, the color of the resulting fluorescence will correspond to that of the fluor used to label the hybridizing sample (for example, green if the sample was labeled with Cy3, or red, if the sample was labeled with Cy5). If both samples hybridize to the same spot, an intermediate color is produced (for example, yellow if the samples were labeled with fluorescein and rhodamine). Then, applying methods of pattern recognition and data analysis known in the art, it is possible to quantify differences in gene expression between the samples. Methods of pattern recognition and data analysis are described in e.g., International Publication WO 00/24936, which is incorporated by reference herein.

Measuring Gene Expression by Measuring Magnitude of Expression of a Population of Proteins:

The magnitude of expression of a first population of genes and/or a second population of genes can be measured, for example, by measuring the magnitude of expression of proteins encoded by the genes.

Any useful method for measuring protein expression patterns can be used. Typically all, or substantially all, proteins are extracted from a living thing, or a portion thereof. The living thing is typically treated to disrupt cells, for example by homogenizing the cellular material in a blender, or by grinding (in the presence of acid-washed, siliconized, sand if desired) the cellular material with a mortar and pestle, or by subjecting the cellular material to osmotic stress that lyses the cells. Cell disruption may be carried out in the presence of a buffer that maintains the released contents of the disrupted cells at a desired pH, such as the physiological pH of the cells. The buffer may optionally contain inhibitors of endogenous proteases. Physical disruption of the cells can be conducted in the presence of chemical agents (e.g., detergents) that promote the release of proteins.

The cellular material may be treated in a manner that does not disrupt a significant proportion of cells, but which removes proteins from the surface of the cellular material, and/or from the interstices between cells. For example, cellular material can be soaked in a liquid buffer, or, in the case of plant material, can be subjected to a vacuum, in order to remove proteins located in the intercellular spaces and/or in the plant cell wall. If the cellular material is a microorganism, proteins can be extracted from the microorganism culture medium.

It may be desirable to include one or more protease inhibitors in the protein extraction buffer. Representative examples of protease inhibitors include: serine protease inhibitors (such as phenylmethylsulfonyl fluoride (PMSF), benzamide, benzamidine HCl, ϵ-Amino-n-caproic acid and aprotinin (Trasylol)); cysteine protease inhibitors, such as sodium p-hydroxymercuribenzoate; competitive protease inhibitors, such as antipain and leupeptin; covalent protease inhibitors, such as iodoacetate and N-ethylmaleimide; aspartate (acidic) protease inhibitors, such as pepstatin and diazoacetylnorleucine methyl ester (DAN); metalloprotease inhibitors, such as EGTA [ethylene glycol bis(β-aminoethyl ether) N,N,N',N'-tetraacetic acid], and the chelator 1, 10-phenanthroline.

The mixture of released proteins may, or may not, be treated to completely or partially purify some of the proteins for further analysis, and/or to remove non-protein contaminants (e.g., carbohydrates and lipids). In some embodiments, the complete mixture of released proteins is analyzed to determine the amount and/or identity of some or all of the proteins. For example, the protein mixture may be applied to a substrate bearing antibody molecules that specifically bind to one or more proteins in the mixture. The unbound proteins are removed (e.g., washed away with a buffer solution), and the amount of bound protein(s) is measured. Representative techniques for measuring the amount of protein using antibodies are described in Harlow and Lane, 1988, *Antibodies: A Laboratory Manual*, Cold Spring Harbor, N.Y., and include such techniques as the ELISA assay. Moreover, protein microarrays can be used to simultaneously measure the amount of a multiplicity of proteins. A surface of the microarray bears protein binding agents, such as monoclonal antibodies specific to a plurality of protein species. Preferably, antibodies are present for a substantial fraction of the encoded proteins, or at least for those proteins whose amount is to be measured. Methods for making monoclonal antibodies are well known (see, e.g., Harlow and Lane, 1988, Antibodies: A Laboratory Manual, Cold Spring Harbor, N.Y.). Protein binding agents are not restricted to monoclonal antibodies, and can be, for example, scFv/Fab diabodies, affibodies, and aptamers. Protein microarrays are generally described by M. F. Templin et al., Protein Microarray Technology, *Trends in Biotechnology,* 20(4): 160-166(2002). Representative examples of protein microarrays are described by H. Zhu et al., Global Analysis of Protein Activities Using Proteome Chips, *Science,* 293:2102-2105 (2001); and G. MacBeath and S. L. Schreiber, Printing Proteins as Microarrays for High-Throughput Function Determination, *Science,* 289:1760-1763 (2000).

In some embodiments, the released protein is treated to completely or partially purify some of the proteins for further analysis, and/or to remove non-protein contaminants. Any useful purification technique, or combination of techniques, can be used. For example, a solution containing extracted proteins can be treated to selectively precipitate certain proteins, such as by dissolving ammonium sulfate in the solution, or by adding trichloroacetic acid. The precipitated material can be separated from the unprecipitated material, for example by centrifugation, or by filtration. The precipitated material can be further fractionated if so desired.

By way of example, a number of different neutral or slightly acidic salts have been used to solubilize, precipitate, or fractionate proteins in a differential manner. These include NaCl, $Na_2SO_4$, $MgSO_4$ and $NH_4(SO_4)_2$. Ammonium sulfate is a commonly used precipitant for salting proteins out of solution. The solution to be treated with ammonium sulfate may first be clarified by centrifugation. The solution should be in a buffer at neutral pH unless there is a reason to conduct the precipitation at another pH; in most cases the buffer will have ionic strength close to physiological. Precipitation is usually performed at 0-4° C. (to reduce the rate of proteolysis caused by proteases in the solution), and all solutions should be precooled to that temperature range.

Representative examples of other art-recognized techniques for purifying, or partially purifying, proteins from a living thing are exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of protein purification, hydrophobic interaction chromatography depends on surface hydrophobic groups and is usually carried out under conditions which maintain the integrity of the protein molecule. Reversed-phase chromatography depends on the native hydrophobicity of the protein and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding proteins at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that can be applied to the purification of proteins is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish band-spreading, and (3) the columns are operated at 10-60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography.

An exemplary technique that is useful for measuring the amounts of individual proteins in a mixture of proteins is two dimensional gel electrophoresis. This technique typically involves isoelectric focussing of a protein mixture along a first dimension, followed by SDS-PAGE of the focussed proteins along a second dimension (see, e.g., Hames et al., 1990, *Gel Electrophoresis of Proteins: A Practical Approach*, IRL Press, New York; Shevchenko et al., 1996, *Proc. Nat'l Acad. Sci. U.S.A.* 93:1440-1445; Sagliocco et al., 1996, *Yeast* 12:1519-1533; Lander, 1996, *Science* 274:536-539; and Beaumont et al., *Life Science News*, 7, 2001, Amersham Pharmacia Biotech. The resulting series of protein "spots" on the second dimension SDS-PAGE gel can be measured to reveal the amount of one or more specific proteins in the mixture. The identity of the measured proteins may, or may not, be known; it is only necessary to be able to identify and measure specific protein "spots" on the second dimension gel. Numerous techniques are available to measure the amount of protein in a "spot" on the second dimension gel. For example, the gel can be stained with a reagent that binds to proteins and yields a visible protein "spot" (e.g., Coomassie blue dye, or staining with silver nitrate), and the density of the stained spot can be measured. Again by way of example, all, or most, proteins in a mixture can be measured with a fluorescent reagent before electrophoretic separation, and the amount of fluorescence in some, or all, of the resolved protein "spots" can be measured (see, e.g., Beaumont et al., *Life Science News*, 7, 2001, Amersham Pharmacia Biotech).

Again by way of example, any HPLC technique (e.g., exclusion chromatography, ion-exchange chromatography, hydrophobic interaction chromatography, reversed-phase chromatography and immobilized metal affinity chromatography) can be used to separate proteins in a mixture, and the separated proteins can thereafter be directed to a detector (e.g., spectrophotometer) that detects and measures the amount of individual proteins.

In some embodiments of the invention it is desirable to both identify and measure the amount of specific proteins. A technique that is useful in these embodiments of the invention is mass spectrometry, in particular the techniques of electrospray ionization mass spectrometry (ESI-MS) and matrix-assisted laser desorption/ionization mass spectrometry (MALDI-MS), although it is understood that mass spectrometry can be used only to measure the amounts of proteins without also identifying (by function and/or sequence) the proteins. These techniques overcame the problem of generating ions from large, non-volatile, analytes, such as proteins, without significant analyte fragmentation (see, e.g., R. Aebersold and D. R. Goodlett, Mass Spectrometry in Proteomics, *Chemical Reviews,* 102(2): 269-296 (2001)).

Thus, for example, proteins can be extracted from cells of a living thing and individual proteins purified therefrom using, for example, any of the art-recognized purification techniques described herein (e.g., HPLC). The purified proteins are subjected to enzymatic degradation using a protein-degrading agent (e.g., an enzyme, such as trypsin) that cleaves proteins at specific amino acid sequences. The resulting protein fragments are subjected to mass spectrometry. If the sequence of the complete genome (or at least the sequence of part of the genome) of the living thing from which the proteins were isolated is known, then computer algorithms are available that can compare the observed protein fragments to the protein fragments that are predicted to exist by cleaving the proteins encoded by the genome with the agent used to cleave the extracted proteins. Thus, the identity, and the amount, of the proteins from which the observed fragments are derived can be determined.

Again by way of example, the use of isotope-coded affinity tags in conjunction with mass spectrometry is a technique that is adapted to permit comparison of the identities and amounts of proteins expressed in different samples of the same type of living thing subjected to different treatments (e.g., the same type of living tissue cultured, in vitro, in the presence or absence of a candidate drug) (see, e.g., S. P. Gygi et al., Quantitative Analysis of Complex Protein Mixtures Using Isotope-Coded Affinity Tags (ICATs), *Nature Biotechnology,* 17:994-999(1999)). In an exemplary embodiment of this method, two different samples of the same type of living thing are subjected to two different treatments (treatment 1 and treatment 2). Proteins are extracted from the treated living things and are labeled (via cysteine residues) with an ICAT reagent that includes (1) a thiol-specific reactive group, (2) a linker that can include eight deuteriums (yielding a heavy ICAT reagent) or no deuteriums (yielding a light ICAT reagent), and (3) a biotin molecule. Thus, for example, the proteins from treatment 1 may be labeled with the heavy ICAT reagent, and proteins from treatment 2 may be labelled with the light ICAT reagent. The labeled proteins from treatment 1 and treatment 2 are combined and enzymatically cleaved to generate peptide fragments. The tagged (cysteine-containing) fragments are isolated by avidin affinity chromatography (that binds the biotin moiety of the ICAT reagent). The isolated peptides are then separated by mass spectrometry. The quantity and identity of the peptides (and the proteins from which they are derived) may be determined. The method is also applicable to proteins that do not include cysteines by using ICAT reagents that label other amino acids.

Numerical Values Representing Comparison Results:

the magnitudes of the expression of gene populations are compared in the practice of the present invention, and the resulting comparison results are expressed as numerical values. For example, the magnitude of gene expression of a first population of genes, in a cell type, in response to an agent is compared to the magnitude of gene expression of the first population of genes, in the same cell type, in response to a full agonist (functioning as a reference compound) of a target molecule, to produce a first comparison result, wherein the first comparison result is represented by a first numerical value.

Any useful mathematical technique can be used to obtain a numerical value that represents a comparison result obtained in the practice of the present invention. For example, the first and second numerical values used in the practice of the present invention can be represented by the scale factor S as defined in the following exemplary statistical methods:

(1).

$$S = \sum_{i=1}^{n} X_i \Big/ \sum_{i=1}^{n} R_i;$$

wherein n stands for the number of genes and/or proteins.

(2).

$$S = \left(\sum_{i=1}^{n} X_i / R_i\right) \Big/ n$$

(3). Fit a straight line by: $X_i = S*R_i$ (4). Least $\chi^2$ fitting: choose a value of S to minimize the $\chi^2$:

$$\chi^2 = \sum_{i=1}^{n} (S*R_i - X_i)^2 / (\sigma_{Ri}^2 + \sigma_{Xi}^2)$$

(5). Least square fitting: choose a value of S to minimize the $Q^2$:

$$Q^2 = \sum_{i=1}^{n} (S*R_i - X_i)^2$$

In the foregoing formulae, Ri, $\sigma_{Ri}$ stand for the log(Ratio) and error of the log(Ratio) for ith gene, or ith protein, from the template experiment; Xi and $\sigma_{Xi}$ stand for the log(Ratio) and error of log(Ratio) of the same gene, or protein, expressed in response to a candidate agent. The template experiment is the experiment that yields gene expression data, or protein expression data, in response to an agent having a known biological activity.

Almost all statistical "fitting" algorithms can be used to generate a scale factor for comparing the expression responses (transcriptional, proteomic or metabolic) produced by an agent with the expression responses produced by a reference agent.

Another exemplary method that can be used to analyze or compare gene expression profiles is averaging. For example, the average expression value for each gene, in a first or second population of genes, response to the candidate agent is divided by the average expression value for each gene in response to the reference agent to yield a percentage expression value for each gene. The mean of all of the percentage expression values is calculated and is the comparison value for the candidate agent. Similarly, for example, if protein expression levels are being measured, the average expression value for each protein in response to the candidate agent is divided by the average expression value for each protein in response to the reference agent to yield a percentage expression value for each protein. The mean of all of the percentage expression values is calculated and is the comparison value for the candidate agent.

Standard statistical techniques can be found in statistical texts, such as *Modern Elementary Statistics*, John E. Freund, 7th edition, published by Prentice-Hall; and *Practical Statistics for Environmental and Biological Scientists*, John Townend, published by John Wiley & Sons, Ltd.

Using the First Numerical Value and the Second Numerical Value:

In the practice of the present invention the first numerical value and the second numerical value are used to determine whether the agent is more like a partial agonist of the target molecule than a full agonist of the same target molecule. Typically, an agent is more like a partial agonist of a target molecule than a full agonist of the same target molecule if the comparison result for the first population of genes is significantly greater than the comparison result for the second population of genes (i.e., the first numerical value for the first population of genes is significantly greater than the second numerical value for the second population of genes).

For example, a chi-square fitting algorithm can be used to compute first and second comparison results (each represented by a numerical value) for several reference full agonists (or, for example, for several different doses of a single full agonist). The first and second comparison results for each reference agonist (or dosage) are plotted on an x-y graph (such as the x-y graph shown in THE FIGURE); the first comparison results are plotted on the y-axis, and the second comparison results are plotted on the x-axis. A best fitting straight line for these data is plotted using a standard statistical fitting technique, which may also provide the confidence intervals for the plotted data. If the intersection of the first and second numerical results, for a candidate agent, on the x-y graph is located at a point above the best fitting straight line, and the distance between the point and the best fitting straight line is statistically larger than the confidence interval for the best fitting straight line, then the agent is more like a partial agonist than an agonist of the target molecule.

Again by way of example, the ratio of the first numerical value to the second numerical value can be calculated. If the ratio of the first numerical value to the second numerical value is significantly greater than a defined value (e.g., greater than 1) then the agent is more like a partial agonist than an agonist of the target molecule.

Ranking Candidate Compounds:

The methods of the present invention can include the step of ranking agents wherein the position of the agent in the rank indicates the level of similarity of the agent to a partial agonist of a target molecule. For example, the ratio of the first numerical value to the second numerical value can be calculated for each agent. The agents can then be ranked based on the value of the foregoing ratio, wherein the agent having the largest ratio is ranked at the top and is considered to be most like a partial agonist of a target molecule, and the candidate having the smallest ratio is ranked at the bottom and is considered to be least like a partial agonist of the same target molecule. Some of the ranked agents may be chosen for further study. For example, agents ranked at or near the top may be chosen for further study.

Screening for Compounds that Reduce Blood Plasma Glucose Levels:

In another aspect, the present invention provides methods to screen compounds to identify a candidate compound that may reduce blood plasma glucose concentration in a mammal (e.g., a human being). The methods of this aspect of the invention each include the step of contacting a cell, of a cell type, with a compound and determining whether the compound causes a significant increase in the level of expression of a population of 29 genes that each hybridize under stringent conditions to a different member of the group of nucleic acid molecules consisting of SEQ ID NOS:1-29, wherein if the compound causes a significant increase in the level of expression of the population of 29 genes then the compound is selected as a candidate compound that may reduce blood plasma glucose concentration in a mammal. Selected compounds may be administered to a mammal to determine whether the selected compounds reduce blood plasma glucose concentration in the mammal.

This aspect of the invention relies, at least in part, on the discovery that the level of expression of the population of genes corresponding to SEQ ID NOS:1-29 is significantly increased by partial agonists of PPARγ. Partial agonists of PPARγ have the property of being able to reduce blood plasma glucose concentration in a mammal when administered to the mammal in an effective amount. Thus, a significant increase in the level of expression of the genes corresponding to SEQ ID NOS:1-29 correlates with a reduction in blood plasma glucose concentration in a mammal.

SEQ ID NOS:1-29 are cDNA molecules that correspond to 29 different genes as described herein. Each of the 29 genes hybridizes under stringent conditions to its corresponding cDNA having a nucleic acid sequence set forth in one of SEQ ID NOS:1-29, but not to any other of the 29 cDNAs having the sequences set forth in SEQ ID NOS:1-29. In this context, stringent hybridization conditions are at least of 5×SSC at 55° C. for one hour. Other exemplary stringent hybridization conditions are 5×SSC at 65° C. for one hour. The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

In the practice of this aspect of the invention, the level of expression of the aforementioned population of 29 genes in response to a compound is typically compared to the level of expression of the aforementioned population of 29 genes in a control cell of the same cell type, wherein the control cell has been treated identically to the cell contacted with the compound, except that the control cell has not been contacted with the compound. If the level of expression of the aforementioned population of 29 genes is significantly higher in the cell contacted with the compound, compared to the level of expression of the aforementioned population of 29 genes in the control cell, then the compound is typically selected as a candidate compound that may reduce blood plasma glucose concentration in a mammal.

The selected compound is typically subjected to further study to determine whether the compound reduces blood plasma glucose concentration in a mammal (e.g., a controlled experiment is conducted wherein the selected compound is administered to a group of mammals, such as rats or mice, and the effect of the compound on blood plasma glucose concentration is determined).

The level of expression of the aforementioned population of 29 genes in a cell (or population of cells) may be measured, for example, by any of the gene expression measurement techniques described herein. For example, any of the statistical techniques described in the portion of the present patent application entitled "Numerical Values Representing Comparison Results" can be used to compare the level of expression of the aforementioned population of 29 genes in a cell (or population of cells) contacted with a compound, with the level of expression of the aforementioned population of 29 genes in a control cell (or population of control cells) not contacted with the compound, and to determine whether a significant difference exists between the levels of gene expression in the contacted and uncontacted cell(s).

The methods of this aspect of the present invention may include the additional step of determining the ratio of gene expression of the aforementioned population of 29 genes, to the ratio of gene expression of a population of 11 genes, wherein the 11 genes each hybridize under stringent conditions to a different member of the group of nucleic acid molecules consisting of SEQ ID NOS:30-40. SEQ ID NOS: 30-40 are cDNA molecules that correspond to 11 different genes as described herein. In this context, stringent hybridization conditions are at least 5×SSC at 55° C. for one hour. Other exemplary stringent hybridization conditions are 5×SSC at 65° C. for one hour.

A multiplicity of candidate compounds may be ranked based on the ratio of gene expression of the 29 genes to the 11 genes, wherein compounds producing a ratio higher than a selected ratio value are further tested to determine whether the compounds reduce blood plasma glucose concentration in a mammal.

The following examples merely illustrate the best mode now contemplated for practicing the invention, but should not be construed to limit the invention.

EXAMPLE 1

This example describes the identification of an efficacy-related population of genes (SEQ ID NOS:1-29) and a toxicity-related population of genes (SEQ ID NOS:30-40) that can be used to determine whether an agent is more like a partial agonist of PPARγ than a full agonist of PPARγ. This Example also discloses the sequences of a population of 29 oligonucleotide probes (SEQ ID NOS:41-69) that are hybridization probes for the 29 genes of the efficacy-related population of genes (SEQ ID NOS:1-29), and the sequences of a population of 17 oligonucleotide probes (SEQ ID NOS:70-86) that are hybridization probes for the 11 genes of the toxicity-related population of genes (SEQ ID NOS:30-40).

Table 1 shows the GenBank accession number and gene name for each member of the efficacy-related population of genes.

TABLE 1

| Accession number | Gene Name | Gene SEQ ID NO | Probe SEQ ID NO |
|---|---|---|---|
| NM_016740 | S100a11 | 1 | 41 |
| AK020722 | 1110003F05Rik | 2 | 42 |
| AK004305 | D10Ertd749e | 3 | 43 |
| NM_025662 | Pigk | 4 | 44 |
| AK016205 | Dixdc1 | 5 | 45 |
| AK011301 | Nap111 | 6 | 46 |
| AK010169 | 2310075E07Rik | 7 | 47 |
| AK014794 | Zmynd17 | 8 | 48 |
| AK014487 | Sdsl | 9 | 49 |
| AK007076 | 1700095D18Rik | 10 | 50 |
| NM_011598 | Fabp9 | 11 | 51 |
| AK010321 | 2410001C21Rik | 12 | 52 |
| NM_026519 | 2610318K02Rik | 13 | 53 |
| BF318286 | 3110043O21Rik | 14 | 54 |
| AK004659 | Cfl2 | 15 | 55 |
| NM_028333 | Angptl1 | 16 | 56 |
| BB326776 | BB326776 | 17 | 57 |
| AK010936 | Ak2 | 18 | 58 |
| AK009798 | 2310044E02Rik | 19 | 59 |
| NM_010918 | Nktr | 20 | 60 |
| NM_019930 | Ranbp9 | 21 | 61 |
| AK003201 | 1110001A23Rik | 22 | 62 |
| AK010201 | 2310076K21Rik | 23 | 63 |
| M20497 | Fabp4 | 24 | 64 |
| BE457517 | Ppp2r5a | 25 | 65 |
| M13264 | Fabp4 | 26 | 66 |
| AF011360 | Rgs7 | 27 | 67 |
| U53228 | Rora | 28 | 68 |
| L23108 | Cd36 | 29 | 69 |

Table 2 shows the GenBank accession number and gene name for each member of the toxicity-related population of genes.

TABLE 2

| Accession number | Gene Name | Gene SEQ ID NO | Probe SEQ ID NO |
|---|---|---|---|
| BC019496 | Agt | 30 | 70 |
| AK005080 | Suclg1 | 31 | 71 |
| AK075624 | Slc25a20 | 32 | 72 |
| BC005792 | Pte1 | 33 | 73 |
| NM_024446 | Nudt7 | 34 | 74 |
| BC009134 | D14Wsu89e | 35 | 75 |
| Z71189 | Acadvl | 36 | 76 |
| | | | 77 |
| | | | 78 |
| D13664 | Postn | 37 | 79 |
| D50834 | Cyp4b1 | 38 | 80 |
| | | | 81 |
| | | | 82 |
| U37501 | Lama5 | 39 | 83 |
| X89998 | Hsd17b4 | 40 | 84 |
| | | | 85 |
| | | | 86 |

The magnitude of expression of a first population of genes (e.g., an efficacy-related population of genes) useful in the practice of the present invention is consistently more regulated by partial agonists of a target molecule than by full agonists of the same target molecule. In the present Example, genes for inclusion in an efficacy-related population of genes were consistently more regulated by partial agonists of PPARγ than by full agonists of PPARγ.

The criteria applied to determining that a gene was consistently more regulated by partial agonists of PPARγ than by full agonists of PPARγ were: (1) the ratio of the magnitude of gene expression caused by the partial agonists over the magnitude of gene expression caused by the full agonists was consistently larger than the average of such ratio determined by using all robust signature genes (wherein signature genes are genes that show greater regulation by the partial agonists than by the full agonists); and (2) the ratio of the magnitude of gene expression caused by the partial agonists of PPARγ over the ratio of gene expression caused by the full agonists of PPARγ was consistently equal to or larger than the ratio of the endpoint efficacy (Glucose Correction) effect caused by the partial agonists of PPARγ to the endpoint efficacy (Glucose Correction) caused by the full agonists of PPARγ.

Genetically altered, diabetic, mice (db/db strain, available from the Jackson Laboratory, Bar Harbor, Me., U.S.A., as strain C57B1/KFJ, and described by Chen et al., *Cell* 84:491-495 (1996), and by Combs et al., *Endocrinology* 142:998-1007 (2002)) were treated with two PPARγ full agonists, and 7 PPARγ partial agonists. The compounds were administered to the animals daily. Serum glucose measurements were taken at the onset (before dosing) and 24 hr after the 7th dose. Glucose Correction was computed as 100−(db Treated With Drug-Lean Treated With Vehicle)/(dbTreated With Vehicle-Lean Treated With Vehicle)*100, all using Day7 glucose measurements. Glucose Lowering was computed as (Day7−Day0)/Day0 for each treatment. Epididymal white adipose tissue (EWAT tissue) was removed from the treated mice 6 hours after the 8th dose and was subsequently profiled using Agilent v1.2 25K mouse DNA microarrays.

Table 3 shows the identity and dosage of the two PPARγ full agonists, and 7 PPARγ partial agonists administered to the mice.

TABLE 3

| Chemical Name | Type | Doses (mg/kg/day) |
|---|---|---|
| 5-(4-{2-[methyl(pyridin-2-yl)amino]ethoxy}benzyl)-1,3-thiazolidine-2,4-dione) | Full (Rosiglitazone) | 3, 30, 100 |
| {2-[2-(4-phenoxy-2-propylphenoxy)ethyl]-1H-indol-5-yl}acetic acid | Full | 3, 30 |
| sodium (2R)-2-(3-{[3-(4-chlorophenoxy)-2-methyl-6-(trifluoromethoxy)-1H-indol-1-yl]methyl}phenoxy)butanoate | Partial | 3, 20 |
| sodium (2R)-2-(4-chloro-3-{[3-(6-methoxy-1,2-benzisoxazol-3-yl)-2-methyl-6-(trifluoromethoxy)-1H-indol-1-yl]methyl}phenoxy)propanoate | Partial | 10, 30 |
| sodium (2R)-2-(4-chloro-3-{[3-(6-methoxy-1,2-benzisoxazol-3-yl)-2-methyl-6-(trifluoromethoxy)-1H-indol-1-yl]methyl}phenoxy)butanoate | Partial | 5, 20 |
| sodium (2S)-2-(2-chloro-5-{[3-(4-chlorophenoxy)-2-methyl-6-(trifluoromethoxy)-1H-indol-1-yl]methyl}phenoxy)propanoate | Partial | 10, 50 |

TABLE 3-continued

| Chemical Name | Type | Doses (mg/kg/day) |
|---|---|---|
| 5-chloro-1-(4-chlorobenzyl)-3-(phenylthio)-1H-indole-2-carboxylic acid | Partial | 10, 30 |
| Partial Agonist No: 1 | Partial | 10, 30 |
| sodium (2S)-2-(3-{[3-(4-chlorophenoxy)-2-methyl-6-(trifluoromethoxy)-1H-indol-1-yl]methyl}phenoxy)propanoate | Partial | 5, 30 |

The first population of genes was selected using the following procedures:

(1) Selecting robust efficacy-related genes: Genes were selected that had expression that was significantly correlated (pvalue for the correlation <0.01) with the efficacy endpoint (Glucose correction). The selected genes were then compared to genes that showed robust regulation (pvalue for replicate combined log Ratio <0.01, and fold change >1.2×) in at least two out of four of the following animal groups that were each treated with one of the following four high doses of the PPARγ full agonist rosiglitazone: rosiglitazone administered at a dosage of 30 mg/kg/day; rosiglitazone administered at a dosage of 100 mg/kg/day; rosiglitazone administered at a dosage of 30 mg/kg/day (in the second batch of the profiling experiment); and {2-[2-(4-phenoxy-2-propylphenoxy)ethyl]-1H-indol-5-yl}acetic acid administered at a dosage of 30 mg/kg/day. 1205 genes were identified using this method.

(2) Computing a fullness score for each treatment: Replicate gene expression profiles of mice treated with 100 mg/kg/day rosiglitazone were combined (error weighted average) into one template experiment. The 1205 genes identified in step (1) were further compared with the robust signature genes that had a replicate combined pvalue <0.01, and a fold change in the magnitude of gene expression >1.3× in the template experiment. 610 genes were identified using this method.

Chi-square fitting of the expression data of the selected 610 genes was used to obtain a fullness score for each treatment (i.e., for each dosage of each PPARγ full or partial agonist). The chi-square fitting formula was:

$$\chi^2 = \sum_{i=1}^{n} (S * R_i - X_i)^2 / (\sigma_{Ri}^2 + \sigma_{Xi}^2)$$

Where Ri, σRi stand for the log Ratio and error for log Ratio of the full template. Xi and σXi stand for the log Ratio and error for log Ratio of the tested compound. This chi square fitting method is described, for example, by W. Press et al., Numerical Recipes in C, Chapter 14, Cambridge University Press (1991).

The fullness score is represented by S in the above formula, and is a measure of the average ratio of the level of gene expression of the 610 genes caused by a test compound (e.g., PPARγ partial agonist) versus the level of gene expression caused by the template compound (e.g., PPARγ full agonist).

(3) Using the fullness score to select genes having expression that was more regulated by PPARγ partial agonists than by the template compound: animals were selected that had been treated with a PPARγ partial agonist, and that had a fullness score (S) greater than 0.3. Genes that were expressed in the selected animals were selected wherein the ratio of regulation (log Ratio) by the PPARγ partial agonist over regulation by the template compound was larger than the fullness score in more than 80% of the selected animals.

(4) Using efficacy end point data to select genes that were more regulated by PPARγ partial agonists than by the template compound: animals were selected that had been treated with PPARγ partial agonists and that had the following efficacy end point measurements: Glucose Correction >40% and Glucose Lowering >40%. Genes were then selected wherein the regulation (log Ratio) of gene expression by the PPARγ partial agonists over the regulation (log Ratio) of gene expression by the template compound was equal to or larger than the ratio of the glucose correction by the PPARγ partial agonists over the glucose correction by the template compound in more than 80% of the selected animals.

(5) Identification of efficacy-related genes: 29 genes (SEQ ID NOS:1-29) were identified that occurred in each of the gene populations identified in foregoing steps (1), (3) and (4). These 29 genes (SEQ ID NOS:1-29) consistently showed more regulation by PPARγ partial agonists than by PPARγ full agonists.

(6) Similar criteria were applied to the Sprague Dawley Rat profiling experiments to select a second population of genes that consistently showed less regulation by PPARγ partial agonists than by PPARγ full agonists. The rat animal model was used because it is believed to be a better animal model to study toxicity effects of PPARγ agonists. The selected rat genes were then mapped to mouse sequences and 11 homologous mouse genes (SEQ ID NOS:30-40) were obtained, so that the first (efficacy-related) populations of genes (SEQ ID NOS:1-29), and the second (toxicity-related) populations of genes (SEQ ID NOS:30-40) can both be used to study the effects of PPARγ agonists and PPARγ partial agonists in the same model organism (mice).

EXAMPLE 2

This example shows the use of the efficacy-related population of genes (SEQ ID NOS:1-29) and the toxicity-related population of genes (SEQ ID NOS:30-40) to distinguish between representative PPARγ partial agonists and representative PPARγ full agonists.

Experiment:

3T3-L1 cells were induced to fully differentiate into adipocytes by the protocol described in *Endocrinology* 143(6): 2106-18 (2002). At day 8, cells were incubated with the testing compound for 24 hours.

The testing compounds included eleven partial PPARγ agonists, two full PPARγ agonists, and two compounds that did not interact with PPARγ: compound L-023499 (a liver X-receptor), and compound L-634273 (a PPARα agonist). The testing compounds and their dosages are set forth in Table 4.

TABLE 4

| Chemical Name | Type | Dose (μM) |
|---|---|---|
| 5-(4-{2-[methyl(pyridin-2-yl)amino]ethoxy}benzyl)-1,3-thiazolidine-2,4-dione) | Rosiglitazone | 1, 10 |
| 5-{4-[2-(5-ethylpyridin-2-yl)ethoxy]benzyl}-1,3-thiazolidine-2,4-dione | Full | 10, 30 |
| sodium (2R)-2-(4-chloro-3-{[3-(6-methoxy-1,2-benzisoxazol-3-yl)-2-methyl-6-(trifluoromethoxy)-1H-indol-1-yl]methyl}phenoxy)propanoate | Partial | 1, 10 |
| Partial Agonist No: 2 | Partial | 1, 10 |
| Partial Agonist No: 3 | Partial | 1, 10 |

TABLE 4-continued

| Chemical Name | Type | Dose (μM) |
|---|---|---|
| Partial Agonist No: 4 | Partial | 1, 10 |
| Partial Agonist No: 5 | Partial | 1, 10 |
| Partial Agonist No: 6 | Partial | 1, 10 |
| Partial Agonist No: 7 | Partial | 1, 10 |
| Partial Agonist No: 8 | Partial | 1, 10 |
| Partial Agonist No: 9 | Partial | 1, 10 |
| Partial 9 | Partial | 1, 10 |
| Partial Agonist No: 10 | Partial | 1, 10 |
| WY14643 ({4-chloro-6-[(2,3-dimethylphenyl)amino]pyrimidin-2-yl}thio)acetic acid | PPAR alpha | 1, 10 |
| 3-(3-{[7-propyl-3-(trifluoromethyl)-1,2-benzisoxazol-6-yl]oxy}propyl)dihydropyrimidine-2,4(1H,3H)-dione | LXR agonist | 1, 10 |

Analysis:

The following method was used to distinguish between PPARγ partial agonists and PPARγ full agonists using the efficacy-related population of genes (SEQ ID NOS:1-29) and the toxicity-related population of genes (SEQ ID NOS:30-40) described in Example 1.

(1) A gene expression score was computed using the expression data of the population of 29 efficacy-related genes (SEQ ID NOS:1-29). Replicate gene expression profiles from 3T3L1 adipocytes treated with rosiglitazone (at a concentration of 10 μM) were combined (error weighted average) into one template experiment. The expression data from the 29 efficacy-related genes (SEQ ID NOS:1-29) were subjected to chi-square fitting (as described in step (2) of Example 1) to obtain a gene score (GS1) for each treatment.

(2) Step (1) of this Example was repeated using the 11 toxicity-related genes (SEQ ID NOS:30-40) to obtain a gene score (GS2) for each treatment.

(3) The FIGURE shows the comparison plot that was generated using the two gene scores (GS1-vs-GS2). The comparison plot shows that the PPARγ full agonists distributed along the 45 degree diagonal line, while the PPARγ partial agonists distributed above the diagonal line. The vehicle samples and compounds that were not PPARγ agonists, or PPARγ partial agonists, distributed around zero, or below the diagonal line.

The observed distinction between PPARγ partial agonists and PPARγ full agonists is independent of the dosage. The results of additional experiments (data not shown) demonstrated that PPARγ full agonists, used at medium dosage, also distributed along the diagonal line, and that the PPARγ partial agonists and PPARγ full agonists can be distinguished regardless of dosage.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method to screen compounds to identify a candidate compound that may reduce blood plasma glucose concentration in a mammal, the method comprising the step of contacting a cell of a cell type with a compound and determining whether the compound causes a significant increase in the level of expression of a population of 29 genes that each hybridize under stringent conditions to a different member of the group of nucleic acid molecules consisting of SEQ ID NOS:1-29, wherein if the compound causes a significant increase in the level of expression of the population of 29 genes then the compound is selected as a candidate compound that may reduce blood plasma glucose concentration in a mammal.

2. The method of claim 1 wherein the selected compound is administered to a mammal to determine whether the selected compound reduces blood plasma glucose concentration in the mammal.

3. The method of claim 1, further comprising the step of determining the ratio of gene expression of the population of 29 genes that each hybridize under stringent conditions to a different member of the group of nucleic acid molecules consisting of SEQ ID NOS:1-29, to the ratio of gene expression of a population of 11 genes, that each hybridize under stringent conditions to a different member of the group of nucleic acid molecules consisting of SEQ ID NOS:30-40.

4. The method of claim 3, further comprising the step of ranking a multiplicity of candidate compounds based on the ratio of gene expression of the 29 genes to the 11 genes, wherein compounds producing a ratio higher than a selected ratio value are further tested to determine whether the compounds reduce blood plasma glucose concentration in a mammal.

* * * * *

SEQUENCE LISTING

```
<160> NUMBER OF SEQ ID NOS: 86

<210> SEQ ID NO 1
<211> LENGTH: 504
<212> TYPE: DNA
<213> ORGANISM: Mus musculus

<400> SEQUENCE: 1

ccgactcctg tcccagccac cgtcagccac agtcgcagcc ggacctcgct cctcaacttg      60

aagcaaaaat gcctacagag actgagagat gcattgagtc cctgattgct gttttccaaa     120

agtacagcgg gaaggatgga aacaacactc aactctccaa aactgaattc ctttccttca     180

tgaacacaga gctggctgcc ttcacaaaga accagaagga tcctggtgtc cttgaccgca     240

tgatgaagaa gctggacctc aactgtgacg ggcagctaga tttccaagag tttctcaacc     300

tcattggtgg cttagctata gcgtgccatg attctttcat ccaaacttcc cagaagcgaa     360

tctaatcctc ttagttccat ccaaccacca agtcatcacc tcccccgacc ccatccacac     420

ctgcactgag cccagcacac ctaccacaac atgtatccca cgcctgctgg caaaaataaa     480

acaatgccat tttttttaa atgt                                              504

<210> SEQ ID NO 2
<211> LENGTH: 837
<212> TYPE: DNA
<213> ORGANISM: Mus musculus

<400> SEQUENCE: 2

ggaaaaatct tacaggatcc agaacaaaca aacaaacaaa aaaaaaaaac cctcttagaa      60

tgaattttac ttttgaagta atggtttata ttttgaaatt gtatttaaga atcctaaaaa     120

ttaagggttg agttctatca taactttctg aaaggacact gttaaaatac tgctctgtgc     180

atatatgaag ctcagaatag tgagcttagt ttaattatct ctgatcattt ttggtcctgc     240
```

```
acatacggaa tatctctgtt aagaggagga gaccgtgtca tatcactggg tagacaggta    300

cccattacct tagcaagtat gtttagtgct cagtgagcgt ttcagacact gtcaagcttc    360

tgctgcacaa aagctccaat ggtaatatgt tataacagtt gaggaagaac ttatgtgctg    420

tttaatgttc tctgaagcct gtgtatgcag tctcatcctg ttttcagtga gggcacttga    480

tttatgtctc atcaccacca ttcctattga aaatgttgct caaagactca catggtgcaa    540

atagtgtggt atgccacatt ttcatgtaag tgcagtagta tcacacagcc tgatgatggg    600

ataggaatgt tctagtgtca ctttcttagt tgatgctgtt tggtgaaatg gttatctgtg    660

ttttattcaa aaggctggtg atattgatgt acttagtgaa gtatctttta tttttatttt    720

tctttaggaa aaatatctag gaaaacatga tatgaaaatt atattcactt cattgtagtg    780

tagcattttc atgtatggca gtgcctgtgt gaaggagttg tagaaatgcc ctgtccg       837
```

```
<210> SEQ ID NO 3
<211> LENGTH: 1775
<212> TYPE: DNA
<213> ORGANISM: Mus musculus

<400> SEQUENCE: 3

gaaaggcgtg gtgagcgaca gaacgatggc ggacgcggag aaaaacgctg ttgcggagaa     60

aaacaacgct gttgcgacga aagaggttct ggctgaggca gcagccattc tagaacctgt    120

aggcttgcag gaagaagcag agctgcctgc caagatcatg gaggagttta tgaggaactc    180

gcggaagaaa gacaaactgc tctgtagcca gcttcaagta gtgaacttct tacagacttt    240

tctggctcag gaggacactg agcagagccc tgatgctctg gcttctgaag atgccagtcg    300

gcaaaaggca actgaaacta aggagcagtg gaaggacatg aaggccacat acatggatca    360

cgtggatgtc ataaaatgtg ccctgtctga ggccttaccc caggttaaag aggctcacag    420

gaagtacaca gagcttcaga aggcttttga gcaactcgag gctaagaagc gagttcttga    480

ggagaaactt cagctggctc agaagcagtg ggtactgcaa cagaagcgtt tgcagaacct    540

gacaaagatt tctgcagagg tcaagaggcg ccggaagagg gctctggaga agcttgacgg    600

atcccatcag gaactggaaa ccttgaagca gcaagcgggg caggaacagg agaagctgca    660

gaggaaccag agctacctcc agctgctgtg ttcgctgcag aataagctgg tcatctctga    720

gggcaaggct gaggacaaag atgtgaaagg gcgagccctt acagccaaat cctaatctcc    780

ttatagatga aaggatgaga agagagccgt attcataccc tgcttgggct gagaccagat    840

tggtttcttc actgttgtat ctctaggcct aagcctggag tttgttgctc tgtacatcta    900

atctccagct gatcacatct ggcatctctt gctttcagtg actgttgtgt tttgtctcat    960

gctaactttg acagtatatt ctggcttgtt ctgtcttcac ctgtgtctaa cttgctgtcc   1020

ttgcaacctg tctctgtaaa agtgtaccag tgatactcac acgcatgcat gcacgcacac   1080

aggcacgcat gccacaacca cccttttctc tcgctgatct tcagtagtct ctcctcttgt   1140

cctctctttt tctttgtctt ctctccctac cagatgtgaa agcaacttta tgcgcctgct   1200

gtaattgttg tctgaggatt actgcgagta agctcaccct ttgtagttac taaactggcc   1260

ggctggctgg gtcagtccgc tgtactggtt cataacccgg cttcaagttg actgattcaa   1320

aggggcctct cttggcttct gactgaactg ctctgcttgg aaagtctgat ggacttcagg   1380

aacagaactg tactgactgc cctgactcag ctgaactcaa ctacaccaaa ttcattggtt   1440

ctctctgctg tactgctctt aggtagcctc tctcctgtgc tgtcctcctg agtcgtgctg   1500

tcaaatctct ctctgattca tcactttgcc cctcaattag actggcagtt tcaaacacgg   1560
```

```
cacttaacat ttcagttgta gtcacttgat actgcattcc gaacttgagt ctattgaatc   1620

cagaatgtga atccatgcct ttgtgactgt gacctcactc tcttcagtat tgtgtaaaag   1680

ttttaggaac tctccaagta aatacttggt aattgctcat tgatagaaca gaaaaatgct   1740

gtgtagataa taaataaaca tataactata agatt                              1775
```

<210> SEQ ID NO 4
<211> LENGTH: 1533
<212> TYPE: DNA
<213> ORGANISM: Mus musculus

<400> SEQUENCE: 4

```
gtcttcgggg cgtgagaagc cggcaaacat ggcggccccc tgcttcctca ctctgcgggt     60

ggctaccctg gccgccttgg cgctcttgtc tctcggcagc tctgccgctg gacacatcga    120

ggatcaagcc gaacagttct ttagaagtgg acacacaaat aactgggctg ttttggtgtg    180

cacatcccga ttctggttta actaccgaca tgttgcaaat actctttctg tttatagaag    240

cgtcaagagg ctaggtatcc cggacagtca cattgtcctg atgcttgctg atgacatggc    300

gtgcaatgct cggaacccca agccagccac agtgttcagc cacaagaaca tggagctcaa    360

tgtgtatgga gacgatgtgg aagtggacta cagaagctat gaggtaactg tggagaactt    420

tttaagggta ttgaccggga ggggttccac ccagtacccc tcgctcaaag cgtcttcttt    480

ccgacgacag aagcaatatc ctcatttata tgacaggtca tggagggaat ggtttcttga    540

aattccaaga ttctgaagaa atcaccaaca tagaacttgc agatgcgttt gaacagatgt    600

ggcagaagag acgctacaat gagctgctgt tcattattga cacttgccag ggcgcgtcca    660

tgtacgagcg gttctactct cctaacatca tggccttggc tagtagccag gtgggagagg    720

attcgctgtc gcaccagcct gaccctgcga ttggagttca tcttatggat aggtacacgt    780

tttatgtctt ggaatttttg gaagaaatta atccagctag ccaaactaac atgaacgacc    840

tttttcaagt gtgtcccaaa agtctctgtg tgtcgacccc tggacatcgc actgaccttt    900

tccagcgaga tccaaaaaat gtcgtgatca ccgatttctt cggaagtgtg cgcaaggtgg    960

aaatcacaac agagaagatc agtttgcagt gggattcaca agtcgtggac agcagttcta   1020

aagaagacgg cacggccgag gagcgcatgg gacctctcaa gtatgctgag cagctcccgg   1080

tggctcagat aatacaccag aagccaaagc cgagagactg gcaccctccc ggaggcttca   1140

tcctggggct gtgggcgctc atcatcatgg tcttcttcaa gacctatggg atcaagcata   1200

tgaagttcat tttctaagac tcaaggatgt atgaggaaga atgaatggaa gactgcagcc   1260

ttggagcaaa acttaggttt tcatatgttt ttaaatatgt tgcttttgtg taaatttggg   1320

aagaaaatta ggaaaattga atattaatga acttttgact ttaaaacata atattgttaa   1380

tgcacttgtt tactggccac agaatatatc tttcattgtg tttgtgtgtt tgagttatag   1440

aaagcagaga gcaatgacat tggaacttta tgcttaattc tttttaccct cctctcattg   1500

taaaagtgag tagtaaaggt gttagttccc acc                                1533
```

<210> SEQ ID NO 5
<211> LENGTH: 1484
<212> TYPE: DNA
<213> ORGANISM: Mus musculus

<400> SEQUENCE: 5

```
gagagagctc ccagggagct gagctgatcg cctttgtgta cagagggaag agacggtggc     60

gtgaccccac ccgggaagcc ccgcggcagg aacaatgcta gcctgcttga cccgcgggaa    120
```

```
cttactggac gtcctgcaag agggcttcaa tgagcaacag ctacaggcct acgtggcctg    180

ggtgaatgcc cagctgaaga agaggccatc cgtgaagcct gtgcaggacc tgcgacagga    240

tctccgagat ggggtgatcc tggcctatct catcgagatt gttggtcagt tggccttgga    300

ctctgatgct agtgtagacg agagaactga cttctttctt ctccattcgc ccttcaaagc    360

aggttgttcc ttctttagaa tgcatggcaa cagcgtcggg aaatacctaa aagtacttgc    420

cctggttaat ctacgtgttg gtcaataaat gctgtgtgcc aggtgctgta ttgtatggga    480

agatgttaac tctgccagtg ccctcagagg ttcctagtct aattgaaaag actggagagt    540

gaggtctgtt ttattactgt ccttagtatt ctgatggagg gaggcagagg aggatacata    600

gaagagatgc cctccttagt cctagggctc aggaatggca gaccagaaga attagtgtct    660

gaatagggaa ggacaacatc cagaagaact gctgtctgaa ttaaaagaca gaagtgggat    720

ggctagaaag ttggctcagc cattgagaac acaggctgct ctagcagagg acctgggttc    780

aattcctagc acccacgtag cagccgacaa ccagtcccag gggaacccac acttttttct    840

gcacaatata catgcaggca aaacactcac acacacacac acacacacac acacacacac    900

acacacacac acacacatgg gggtggcggg agaagaaaca acagggagta gcattcaggc    960

caaaagagaa aatgtcacca gcaaaaggac tggcctccat gacattcaga cccaagtgtt   1020

gaaggggttt gctcttcact tttggggctg ttcttcttat agcattatgc ccatgatgtt   1080

tgtccatagc ttgctatgat ttctctcccc tgactagcaa ttagccatga tttagactga   1140

gcttttaaag aggttgttac actgtatttt gctttttttgg ttccacgaac cctagtcgga   1200

tgcacagaat aagttctcca acatttatta ttggtcagtt gatgttgctt agtgtcccca   1260

gaggtctgtg gtgtggaggg agctgctttc cacaggcagc ctatctgtga atactttctt   1320

gtattcacga ggcagtagta accacggctg ctaggatgga atgctttcta tcttgtgtga   1380

attgatttgg ccatcatacc cttagaaaat agatattatc attcctgttt tcaggaaaca   1440

aaaggaaaaa tctataaaaa taaataaaga cttaagtatg tgtc                    1484
```

<210> SEQ ID NO 6
<211> LENGTH: 1960
<212> TYPE: DNA
<213> ORGANISM: Mus musculus

<400> SEQUENCE: 6

```
gaaaggagat tgatatttga aagacgagtt tgttctacct agcaccctag ctctagctct     60

gtcagatacg ttaatgcata catcctctct aatgcatgtt catttattgc tgcagtttgg    120

ttcttctgga gtattttcat catttagcta ttggaataca attatgaaaa ccaactgttg    180

aacatacttg gagtagctgt ttctttccta aagaaccaaa gttgttttca gctaatagaa    240

caggttgaag tccgcctgca ttagctgtgt tttccctcat cttgttagag ggatgcacag    300

ggcacggtga catcatttcc ctcatgttgt tagagggatg cacagggcac ggtgacatca    360

tttgagggag gaaaattgtc gttaagaatt tccagtaaga tcaaacttaa taactgagat    420

tatgaaagca tttttatgtt ttcgatgata taaacaaaag tcaactcgtt tatagcaagg    480

tgaacaaacc ctaggttctc ttgaagttga tagtatttaa tgtattttga aaattaacct    540

ccattaatta aatcttttct ttgtggtagg gcctaccttc tgctttcctg gaaaagatga    600

atatacatca tatgaaccta ttttgagttt ttctgttgtt tgtttgccta attttgtttt    660

tatagcctaa aataaaaata tgacacagtt ttagctctca tgggatgctg tctcggtttg    720

tactgattga ggctattgca gagggttagt tggaattcag ggtgcctag ttttctatat    780
```

```
tgaacaacgc tggaggagct aatacacacg tgctttaaaa aaagtgatat gctctagttt    840

gagcagaaag gtacagttgt gcttgttaga actgaaacct ttgtttggac tttgtttatt    900

ctgtcctcag gaggatgagg agtgtcggga gccatgctgt ttatttactg tgcataacca    960

agaatgggtg ggactgttga ttcaactacc tcaactctgt taaggcatat tggggtatat   1020

ctcacaaact ctcagtctta cttgcaaaat gctcaaaaaa ttgggcctct ataccatgag   1080

tgtgatattc agcattatat tcacaccaag ctttgatgat taaactggag aatgaagttt   1140

aaacacttct attctagatc tgagcatgtg gctccaattt tagtgggaag gaatgaaagt   1200

agtgtatgat ttcaagagat tgaagagttt tgggattttt gagttttacc cccttcaga    1260

tatttcaagt gaccacatta taaaacaccc taaggtggta acgaggcagg ggaggatggc   1320

atgaagttgc attaagtttc agaccactga gagccacatt taaaatacct caggctaatt   1380

actgttcact ttggggcagg agtaggtttt gccagggtat agtaattgga ttgcactcca   1440

aggaaagttc ctattgttaa taaaatttac gtagaggaga aacgtttgtt tgaggtggta   1500

gttctttctg tgaggtttta gtattcgaac tcttagaatg tgaacacatt cgagagctga   1560

cttcttcctg agagttttaa ctactggaaa tccttaacca attatatttt ctttattttg   1620

agaatgattt ggttgctttt tcttagatgg tttctgctat ttctgtaatt catagttcat   1680

ctaaacacag cctattttcg tgaacattga agtttgtaac ggaaagatag gatctcattt   1740

tcagtgaact tccagactag cgcactcttc ccttccctct gtaggaagta gctgttgcca   1800

aagcgaagag gtagctggct cttgtataat gggaaagtgc cgtgtggagc ttcaggggtc   1860

agtgtttatt atgacatctg tcagtcccca aatggttcta ttctctacaa gtctgaaata   1920

tgtaatctga aatccttaat aaaattggat ctaattttat                         1960
```

```
<210> SEQ ID NO 7
<211> LENGTH: 1201
<212> TYPE: DNA
<213> ORGANISM: Mus musculus

<400> SEQUENCE: 7

aaattccacg aagataaaat gtgtgtagag agacctttgc ccagaggtgg cccactggaa     60

gacttgaggg tctttggggg aactaaggca atagggtgag gtaaaaggca gagtgtttgg    120

tggataaagg ccccaccaaa ataagcagaa ggcgggtaga gcctgggaaa gggtggtagg    180

tgtgtgggga gaggggctta tttacaaagc tacaaaacct gcacacagga gcacgtgagt    240

tttctttgga aagagagagg aagctagaag agggttgaaa tggaattaga aagaaatgcc    300

cttgttaaca acacaaagaa attcaagagt cccactttgg taggatctca agacagcagg    360

gcagcttccg ggtcaggagg gaagtcagtt ttagaaagtg tgttccaaag agacgtcagc    420

ctgattggat tctctcttcc agaatctagg aactgccttc cgggaagcct tgttttccat    480

gcccggaaaa ttagggttcc agcagggggc agcagcgagt tgtggagaac tggcagctgg    540

ggaaagcaag gtgcctctgg agctgagctc cctagctgga agctggagca gcagggccag    600

ctggcttgcc caccctaact ccctctcagc tgcttctacc atggatcttt ctctaatgtg    660

aaactttaga gcttgccaag accctcctgt gttccttgcc tttggggccc cctttacctg    720

aaagttgggg agagtggggt gctgcttcat gtccaaggct tgatttctta tagttactga    780

ccaggttttc tcctaaggac acatttgttc cccctttaat ggctgatcag gagcaggcaa    840

cacctccccc aattgatagc tacaggctac ttccttctcc tcacctacat gtattccctg    900

cttcttagaa ttgtagctca ttgatatttt ggggtgggga ggggatgaaa accacaaacc    960
```

```
ttttatacca tacaaagctt tgctttttat tttttatttt taattttttt tttcttggtc   1020

cccttccctc ctctgaatgc ttggagacgg agaagctgag gagggtgggt aagtgttgga   1080

tgaggtcctc tgtgctgatg ggctaatgtt gtgggcagat gcagtttcct gtgggctcta   1140

ggggagtccc ttgagttgct gtgttctggt gagcagccgg accaataaac ctgcttttct   1200

c                                                                   1201
```

```
<210> SEQ ID NO 8
<211> LENGTH: 1606
<212> TYPE: DNA
<213> ORGANISM: Mus musculus

<400> SEQUENCE: 8

gacttcactt ggtggaaaga gaaggaagga agcctagggc ttaacaggca ctggtcccca     60

agttcattgg tcatggctcc tcgttcacgg cggcgaaagc acaagaaacc cccaccagtg    120

attcccatga ttgaaatccc acccacagaa gtgtctccag tatctccagc cctctcaaaa    180

cctggcccta gcattgatgc acttggcttc atttccttgg acaataatgt accaggtctg    240

tcccagttga tcctccaaaa gctgaacatg aaaaactatg aagaatacaa gttggtgata    300

aatgggggaa ccccagtatc aagctttgga tttcgatgtc aacaagaaat gttccagaag    360

atggaggaca cattcagatt ctgtgcttat tgtaaagtgc tccctcatgg cctttccaat    420

tgcaaggttc tccggcactg taagaggtgc agaaatgtct attactgtga tacagagtgc    480

cagaggtcag attggccagc acataggaag gtttgtcgag agctccgtct tgtggctgta    540

gatcgtgtca tggaatggct tctggtcaca ggtgattttg tcctaccctc aggaccttgg    600

ccatggctac ctgaagatat acagaattgg gatacctggt tttctatgag ggggtttacag    660

ctagaatcta cattgaatgc tcttctgggt agtcactcta tgaccatgct ttgggcaagt    720

ctaggaaggc cacggccaga cccagatgtc ttgcatggct ctttgaagcg gttgatgaca    780

gatgttctgt cacggccctt gaccctgggc ttagggcttc ggactgtggc aatagatgtt    840

gggaagactg gaggaagcac attgcatgtg gttggtgctt cccacgtaga gacatttctt    900

attcgttctg gagattatga tgagcttggc tacatgtttc ctgaacacct tggctttcat    960

gtgatcatgg tgggtgtgga tgtggctact gaccttttac agagttcttc atctttatcc   1020

ttggagcctg gaacaattca gcttagtggc cacagggccc tgtatcatga cttctgggag   1080

gagcaaatag agactgggat tctggcccat ccagatttgg tggctgcatt ccatccaggt   1140

ttccatgcct ccccaggctt gatggaagct tggttaccca ccctgctgct acttcgtgac   1200

tatgagattc caacattgat tactgtttac agccaacagg aactggaagc ctctttgcag   1260

attctggtga acttggatac acacatcatt gcttgtggag ctaatccttt cgcatccctc   1320

aaaccagaac aagtctattc taatcccaac aagcaaccag tatacagcag tgcctactac   1380

atcatgtttc ttggaagttc ccctgccaat tagataagaa gcaacgagaa ggaaaaaaaa   1440

aaaaaacaaa accagatgat tttcagtaa ttgaaccaag tctttactga atgcctggaa   1500

aatgaaagct taatcaactt accctgttga tgtcagattt ttgccagctt tgaaccctgt   1560

ggtatgctaa accttattca cagttcaaat aaagatgttt aaaccg                  1606
```

```
<210> SEQ ID NO 9
<211> LENGTH: 824
<212> TYPE: DNA
<213> ORGANISM: Mus musculus

<400> SEQUENCE: 9
```

```
ggggaagggg ccgaggtcca gctgactggg aaagtctggg atgaagccaa tgtaaaagca     60

caagaactgg ccacaaggga tggctgggtg aacgtctccc cgtttgacca tccccttata    120

tgggaaggcc atgccagcct agtgcgggag ctgaaggagt cactagggac ccctccaggt    180

gctgtggtgc tggccgtggg gggcggaggg ctcctggcag gtgtgactgc tggcctgctg    240

gaggtgggct ggcagcatgt gcccatcgtt gccatggaga cccgcggggc gcacagtttc    300

aattcggcct tgcaggcagg caggccggtc accctgccag acatcaccag tgtagccaag    360

agcctcggag ccaagacggt ggctgcacgg accttggagt gtgcaaagga gtgtgaggtc    420

ctctctgagg tggtagaaga ccgggaggct gtcagcgctg tgcagaggtt cctggacgat    480

gagcgcatgc tggtggaacc tgcctgcggt gccgccctgg ccgccatcta ctcgggcatc    540

ctgtggaggc tccaggctga gggccgcctg agttctgccc tagcttccgt tgtggtcatc    600

gtgtgcggtg gcaacaacat tagtagccaa cagcttcagg agctgaaaat ccagctgggc    660

tgcagctgaa gaatctcagg aactccccca gaggttcctg gacaccttgg tgggtcactc    720

aagggacctc ggttccagtg gtcctgccct cttccttcca ggtagccctc ctgggttgct    780

ctcagtggct ccctgctgtc cagtgaataa acctgactga gctg                     824
```

<210> SEQ ID NO 10
<211> LENGTH: 687
<212> TYPE: DNA
<213> ORGANISM: Mus musculus

<400> SEQUENCE: 10

```
ttagttgtca gccccagtcc acttccctcc ccacatcaag gaggaatgca tcctgagcag     60

ctgaccctgg agccacacag aatgtgggta cagaaggcac ccttggccac atcctcccca    120

cttaagacct ctgggatttc ttttggagta cctgaaggct tcgcgaattg ctctaagcga    180

attgctattt tgagcaccca gcccagtcct tttctccacc cctcccaacc taaacccaga    240

cagttcatcc actcgttgcc ccacgcccag tcccactctc acactcactc tgaagaagca    300

gcagtttcca cagcaggacg cgggacagca gctccatggc gcctgcgggg gacgtgcttt    360

gtcttactca gctctaactc tccagaaaaa cagccgaccc cctctccctg ccagcacccg    420

ctgacatcac ggagccctgg gccgggtctg ggccccgccc actgcgctgc tcaactgctt    480

ggcctccccc atcttgactg gcctataatg ctgcaaacac cctgtccggg cccagttggt    540

gggagggtct gagtagaggc tcggccagtc actggtcagt cttggggagg agcagtagct    600

cagtcctggg acagaagacg aggcctggat gtgaagattc ctgaggccaa gcgggtgcca    660

agcatctggt aaacttcctg agtttcg                                        687
```

<210> SEQ ID NO 11
<211> LENGTH: 399
<212> TYPE: DNA
<213> ORGANISM: Mus musculus

<400> SEQUENCE: 11

```
atgattgaac ccttcttggg gacctggaaa ctggtctcca gtgaaaactt cgagaattac     60

gtgagggaac tgggagtgga atgtgaaccc cggaaagttg catgtttaat aaagccaagt    120

gttagcatta gtttcaatgg ggaaaggatg gacatccaag caggaagtgc atgcaggaac    180

acgaagatct ccttcaaatt gggggaagag tttgaagaga ccactgcaga caaccggaaa    240

gtgaagagcc ttataacttt tgaaggtggg tcaatgatcc agatccaaag atggcttggc    300

aaacagacaa caattaaaag aagaattgtg gatggaagaa tggtagtgga gtgcaccatg    360
```

aacaatgttg tcagcactag gacctacgaa agggtgtag 399

<210> SEQ ID NO 12
<211> LENGTH: 1113
<212> TYPE: DNA
<213> ORGANISM: Mus musculus

<400> SEQUENCE: 12
gaggtagggt ttcgccagag accccggaag cgacggcttc tcgtctttgc taaggcttct 60
ggtttttgct acggtttctg atttcggctt tgggatgggt tgcgacggag gcaccatccc 120
caagaggcac gagctggtga aggggccgaa gaaggtcgag aaggttgaca aagacgctga 180
actggtagcc caatggaact actgtaccct aagtcaggaa atcctgaggc gcccaatagt 240
tgcctgtgag cttggcagac tgtataacaa agacgcggtc atcgagtttc tgttggacaa 300
atctgctgag aaggccctgg ggaaggcggc atcgcacatc agaagcatca agaatgtgac 360
agagctcagg ctttctgaca accccgcctg ggaaggagat aaagggaaca ccaagggcga 420
caagcatgat gacctccaga gagcgcggtt catctgccct gtggtgggcc tggagatgaa 480
tggccggcac aggttttgct tcctccgatg ctgcggttgt gtgttttctg aacgcgcctt 540
gaaggagata aaagctgaag tgtgtcacac gtgtggggct gccttccagg aggaggacat 600
cattgtgctc aatggcacca aggaggatgt ggagatgctg aagaagagga tggaggagag 660
gaggctgagg gccaagctgg aaaagaaaac aaagaaaccg aagacagcga ccgagtgtgc 720
gtcaaagccg gtaccacaca agattccgca gggccatcaa aagtgaagtc tggcaagcct 780
gaggaggcgg accctgatcc tagagagaag aaaagcaccc cggctcccag gggcgcagca 840
actaatggga gtgcgtctgg gaaagttggc aagcccccat gtggggccct gaagaggtcc 900
attgcagaga gcgaggagtc tgaaacctac aagtctatct tcaccagcca cagctctgcc 960
aagcgctcca aggaggagtc tgcgcactgg gtcacccaca catcctactg cttctgaagc 1020
gggaccgggc cttcaccctg ggtttcccgt ggccttctgt gccacacttg cttggtgtgg 1080
cactgtgcta taaagctgtc ctctgcagtc ctc 1113

<210> SEQ ID NO 13
<211> LENGTH: 976
<212> TYPE: DNA
<213> ORGANISM: Mus musculus

<400> SEQUENCE: 13
gatgcgccgg aagtgcactg cggcgaacgc caggaagtcg gagagcttgc agttgcagct 60
agttcttacc tgcagaacgc aagcggccgg agggtgtggg tacttttagc cagcggccgc 120
tgtcatgacg acccaggggg gcctagtggc caaccgaggc cggcggttca aatgggccat 180
tgagctgagt gggccgggag gaggcagcag gggccgaagt gaccggggca gtggacaggg 240
agactccctc tatccagtcg gttacttgga caagcaagtg cctgatacca gcgtgcaaga 300
gaccgaccgg atcctggtgg agaagcgctg ctgggacatc gccttgggtc ccctcaagca 360
gattcccatg aacctcttca tcatgtacat ggcaggcaac accatttcca tcttccctac 420
tatgatggtg tgtatgatgg cctggcgacc cattcaagca cttatggcca tttcagccac 480
tttcaagatg ctggagagtt caagtcagaa gtttcttcaa ggcttggtct atctcattgg 540
gaacctgatg ggtttggcat tggcagttta caagtgccag tccatgggac tgttgcctac 600
acatgcatca gactggctag cctttattga gccccctgag agaatggagt tcagtggagg 660
aggcttactt ctgtgacccc cagaaagcac catgcatatg gacctcatct gcattttaag 720

```
ctgttgactc ctaaatatcc tcccttaaaa cagtcatgca tgtggagaag agcctcctgt    780

ggtgaggcca gtgtgcagca tgttacagca gaaaagaaac tacagcacaa cttatgactg    840

aaaataatgt agaaaacttt atttatgttc ccagcacaga gcaaaacaaa caaaaccaga    900

ctctatgtaa acaaaagaat agcagctgct cagtagcagc ttctcctttc aataaattaa    960

acggttgaga acaatg                                                    976
```

<210> SEQ ID NO 14
<211> LENGTH: 179
<212> TYPE: DNA
<213> ORGANISM: Mus musculus

<400> SEQUENCE: 14

```
tttttttttt tttttttgc ttggcatatt tcttttcttt taaatacaac ttgcactgtt      60

tttactcata aatgagaagt tttatgttgt ttaacaatga cacctaaggc caagcgtcac    120

atacaaatca ggagtgaagc tctcatctgt gtagatgatg gtgtcctgcg ccatgtcct     179
```

<210> SEQ ID NO 15
<211> LENGTH: 2929
<212> TYPE: DNA
<213> ORGANISM: Mus musculus
<220> FEATURE:
<221> NAME/KEY: misc_feature
<222> LOCATION: (624)..(624)
<223> OTHER INFORMATION: Wherein N=A,T,C or G

<400> SEQUENCE: 15

```
ggcagctccc ggcgtgccct gccatctctg ctgcccgccg ccgacccctc cttcttctcg      60

tcccagtgcc accgagccgg agtccgagcc accgccgccg cagccacttc agccgcgggc    120

actatggcat ctggagttac agtgaatgat gaagtcatca aagtttttaa tgatatgaaa    180

gtaagaaaat cttctacaca ggaggagatc aaaaaaagaa agaaagcagt tctcttctgt    240

tttgagcgat gacgaaagac aaataatagt agaggaagcc aagcagatct tggtgggtga    300

cattggtgac actgtagagg accccctacac atcttttgtg aagttgttgc ctctgaatga    360

ttgccgatat gctttgtacg atgccacgta cgaaacaaaa gagtctaaga aagaagacct    420

agtatttata ttctgggctc ctgaaagtgc accgttaaaa agcaggatga tttatgctag    480

ctctaaagat gccattaaaa agaaatttac aggtattaaa catgagtggc aagtaaatgg    540

cttggacgat attaaggacc gctcgacgct gggatagaaa ctggggggca gtgttgtagt    600

ttcccttgaa ggaaagccac tatnaaataa tagccaagtg ccatttgatc ttaaggggct    660

tacacgtatc tctccagctc agtccactgg aattgtatta ggttttgttt ttttttgtta    720

attccctttt cactggtccc gttcgtgaat gagtgaatat aagaagcctg tcagtattgc    780

catgagactg tttcatatgg ttacttttct gtattcccaa ggaatgcctt cctgtcttat    840

tttagccaaa acaaactggt tccatgcctt ccttgcagtg aacgttacaa tggatgtggt    900

tgtcaatgtg aatagcttag agtactacaa agggtaagct aactgaatgc cttgaaaata    960

ttatccactg gtcggtcata tgggagactt gtttcagtat tatttatagt tgcacttgat   1020

taccgtcctc tgaggcactg gagccttcat acacctcacc tgccttggca agcctatttt   1080

tgtgacctgg cagcacagat ttaacactat tcgttaaaag cacttttttt ttaatgcgtt   1140

taatccctta taaagaatgc caattaagtt ttattacctg tcatcaattt atcctagtat   1200

ctcagtgttc attcttcttg ccttcatatt tttttcaaag aaacagctgt gctaatgtct   1260

ttggtttccc gatgagtgta cactactgta taatttatgt ttaccatatg agtcttgaaa   1320
```

```
cactacagat attttgaata tcagtcatgg tggcaatttc tgtataaaag agccttaaat   1380
ggaacattgt tttgagatca aactccctac cctcacaaaa gtggccacgt tgcaataaaa   1440
attgtggcag attacagaat gttgccttgt tttccttgga aattttgcaa attgttatgt   1500
gaaattttag ggtaacggtg attaagctct gcactggtat ttggaatttt ttttccttta   1560
atctttggtt taaaaacatc ttaaaatcac ttatatacaa tcattaaaag agtggtaatt   1620
ttataaatgc ttatttatgt tataaaatgg agatcagaaa aaaattcttt ttgcactttg   1680
gcctatccag tatcttatct atcctctaga taagctagga tattaatcca gagttacatt   1740
actgagaatt gagtagtata agtaggatgt ttttattact tggtcataat gaaaataatt   1800
tgtaaaatgt cattcgaagg ttaatgatga ttgtgatgtt taggaatgtt tgtctcagcc   1860
acagttcctt catagctttt ccaaaatgaa ttgggaaaaa aaaatcgtat agcagtctta   1920
aagcttagta atggaacttg gctgtggccc agagctttct ccttatagag aatttgatct   1980
gctccgtgtg cgctctctgc tattagccgg agctatttat ggcaaacaca tgcttttgta   2040
tcttgtcata gtcatccaca gatggcaaaa ctggacttga ttctactggc atgtaagaca   2100
ggcgtgctag tgagcagtcg tgtgtggctc tggactctga ccccagagct ctgaagaatg   2160
ctcttatcag aagataggaa atgaaaatat ccttttttaa aatatgtgga agtaatttgg   2220
gtataattag tttttttcta ccttttggaa agttgttttt ttgttgtttt ttttttttc    2280
ccagatgaga acattaacat agtggttaaa tgtctaggct tccatttaaa actacacaaa   2340
tgacttggga tctttttagc actaaggaat ttgatttcag ccttccagct gttgctgtga   2400
gttgttccag acctttctgt ggctttttgg taaggctgct tagaagcatg agaagcatga   2460
gaatggtaat gtgtgctaaa cctatgttta accaatcttt gcaccaaagg actttttcac   2520
caatttattt tgttattctt ccaaatatta agtgatttct aaaaggtaaa gggtgacctt   2580
ttgtttttat atctaatttc tcaatttctt tatatgcatt tttagaataa tttgagagat   2640
taaatgctgc ttgaaactat tatactttga gttttagatt ggccaaatac attaatgtag   2700
ttaaattcat ctttaaagta cacatatgtg cctagagcca aaaaataata atgatttaat   2760
ttatgacctt atgttgagac taatttcaca tcttattttg cagtcattta cagtgaaaca   2820
atgttccagc tagctttaaa agctatacgg tgctaattag taaaatattg agggcaatat   2880
tttactgcta gcttgcaaaa ttataagtgt tttaaaaata aaatacatg               2929
```

<210> SEQ ID NO 16
<211> LENGTH: 1330
<212> TYPE: DNA
<213> ORGANISM: Mus musculus

<400> SEQUENCE: 16

```
gacagtctgt cagctgcggc tggtttctgc acatttccat gcagcagaca gcacaggcac     60
agaaccttct ctgctgcatt agagaagtcc acagatagcc ccaagttaca taggtggccc    120
agcaaactca gtccattagt gctgtgaaaa gaagttcctt actccttgga ttcaccggtc    180
agagcaaaaa acgcagttac ctctgaagta aagccgaaca aacttctaca ctgatctcag    240
agagcaaggg caaggacgca cgttcacgga ctcgcttttt tcaacagaca acaaagacgc    300
tgtggtagaa tttcatttca aaatgaaggc ttttgtttgg accctaagtg tactactctt    360
cctactgggc agtggtcatt gcaaaggagg acaactcaat aaaaaaaata acccaaagga    420
gatatccccg tgctactgat gggaaagagg aagcaaagaa atgttcatat acattcttgg    480
tacctgaaca aaaaataaca gggccaatct gtgtcaacac caaaggtcag gatgcaggca    540
```

```
ctattaagga catgatcacc aggatggacc tggagaacct caaggatgtg ctgtctaggc    600

agaagcggga gatagatgtc ctgcagctgg tggtagatgt ggacgggaac attgtaaacg    660

aggtgaagct gctgagaaag gaaagccgga acatgaactc cagagtcacg cagctctaca    720

tgcagctact acatgagatc atccgtaaaa gagacaattc actcgaactt tcccagctgg    780

aaaacaaaat cctcaatgtc accacagaaa tgctgaagat ggcaacaagg tacagggagc    840

tagaggtgaa gtatgcgtcc ttgacggatc ttgtcaataa ccagtctgtg acgatcactg    900

tattggaaga gcagtgcctg aggatgtttt cccgacaaga cccccacgcg tctcccctc     960

ttgtccaggt ggtaccgcga cacagtccta acagccacca gtacacccct ggtctgctgg   1020

gaggcaatga gatacagagg gacccaggtt accccagaga cgtaatgcca ccacctgatc   1080

tgccaacagc tcccacgaaa agccctttca agattccagc agtgactttc atcaatgaag   1140

gtgagttact gcttcctggc caatggaaga acgaagctgg tatgctgatg ctgtatgatt   1200

cacgcaacaa tactcttatc ttagtaagtc ctacttctta tgtgctgatg ccattataca   1260

tgtccaatca aaattttcac tttttaaagt gatgtttgga tttgatataa aacatctctt   1320

ttctccgtgc                                                          1330
```

<210> SEQ ID NO 17
<211> LENGTH: 289
<212> TYPE: DNA
<213> ORGANISM: Mus musculus

<400> SEQUENCE: 17

```
ccaaagcacc cccatctttc gagttcgccc ccattccagt caacagagcc acttccaaga     60

ccacccctcc agcctaccca gagtaaccca aaagaacaaa aaattcccca tctgtactct    120

ttcgggctca taccttcttc tttggaacat cacgtgggtg agctccagca tatggaaatt    180

ctctggatat ttctgggaa accccctcccc gtgttcctct tcccgtggaa atgctatgcg    240

ggtttcgcaa tcgggtattc tcattaaatg gaaattctgt gtgcgctcc                289
```

<210> SEQ ID NO 18
<211> LENGTH: 980
<212> TYPE: DNA
<213> ORGANISM: Mus musculus

<400> SEQUENCE: 18

```
ggaggtgtgc ggctggctgt tggagtgaag ccttggaaga catggctccc aacgtgttgg     60

cttccgaacc ggagattccg aaggcatccg ggccgtgttg ctggggccgc ccggggctgg    120

caaggggacg cggcacccaa actggctgaa aacttttgtg tctgtcattt ggccaccggg    180

gacatgctga gagccatggt agcttctggc tcagagctag gaaaaaagct gaaggcgaca    240

atggatgcag ggaaactggt gagtgacgaa atggttgtgg agctaattga gaagaatttg    300

gagactcctt cgtgcaaaaa tggctttctt ctagatggct tccctcggac tgtgaggcag    360

gctgaaatgc ttgatgacct catggagaag aggaaagaga agctcgattc agtcattgag    420

ttcagcatcc aagactcgct gctgatccgg aggatcactg ggaggctgat tcaccccaag    480

agtggccggt cctaccatga ggaattcaac cctccaaagg agcccatgaa agatgatatc    540

actggggagc ccctgatccg caggtcagat gacaacgaga aagccttgaa gacccgcctg    600

gaggcctacc acactcagac cactccgctc gtggagtact acaggaaacg cggcattcac    660

tgcgccatcg atgcgtccca gacccctgac atcgtgtttg cgagcatcct ggcagccttc    720

tccaaagcca catcctagta acagaaggcc aggcgagacc gcacccctgc tcatctcccc    780
```

```
gccgtgggat ccctgctctt aggtgctggg cagagggaag agggtggtca tgggaaggaa    840

ggatggatgg atggtgaggg aggtggggag gggctcctcg agagaagatt ggaacagtgg    900

cagtgttata attagtaagg ttttttttt ttacacatag atgagaattt ttaaagtata    960

agcaagggaa aagattaatc                                                980
```

<210> SEQ ID NO 19
<211> LENGTH: 617
<212> TYPE: DNA
<213> ORGANISM: Mus musculus

<400> SEQUENCE: 19

```
gagtgtctcc acggactaca gtggatggca tcgaagattc cctttgccac agatctgaca     60

gactatgaga aaatgccagt aagtccattt gggaaagtga agcccagcgg agaggggaca    120

gcacaaaggc ctatagaaat aagtgcctca ccattagcag agctggagga caagataaag    180

cggcacacac agcagatccg cactcgaagt ttcctgggta caaacccaat gcaagacatt    240

aagacagcca accaggacct ggaaaccact aagaaacttc aggaggagtt aaggaaactg    300

aaagtggaga tgaccttgaa caaagaccat ccatttccat ctttcactgg aaacctttca    360

cttcacccac cagcatcaca gcctcaaaat atattttta acacgaaatc ctaggaaggc    420

agcgctgtca gcaggagtga caagtacctt ccacacgagg agctgctgtc ccccatgtgt    480

gtggggactg gcctggatga caactcgcgg gtaactcgcg ggtcttccct gccacacagg    540

ctatggcttt taatagacct gattccttcc tgaggctata gaaggtttag ctgcattaaa    600

cgagatgctt cagcagc                                                   617
```

<210> SEQ ID NO 20
<211> LENGTH: 7036
<212> TYPE: DNA
<213> ORGANISM: Mus musculus

<400> SEQUENCE: 20

```
gcctcgcgag ctctggcgtg gcgctcgccg gctggccctc acggggaaga ggtggcgttc     60

cgttggtgac gttaggctcc ggcggcgccg gcagggcgtt ctccggagct gtgcggccag    120

ctcgccgccg tcccgctgct gcgctcgcga tgggcgccca ggaccggccg cagtgtcact    180

tcgacatcga gatcaaccgg gaaccggttg gtcgaattat gtttcagctc ttctcagaca    240

tatgtccaaa aacatgcaaa aacttcctat gcctgtgctc aggggagaaa ggccttggga    300

aaacaactgg gaagaagtta tgttataaag gttctacatt ccaccgtgtg gttaaaaact    360

ttatgattca gggtggggac ttcagtgaag gtaatggaaa aggtggagaa tcaatttatg    420

gtggatactt taaagatgaa aactttattc tcaaacatga cagagcgttc cttttgtcaa    480

tggcaaatcg agggaaacat accaatggtt cccagttttt cataactaca aagcctgctc    540

cacacctgga tggggttcat gttgtttttg gactggtaat atctggtttt gaagtaattg    600

aacagattga aaatctgaaa acagatgctg caagcagacc ttatgcagat gtccgagtta    660

ttgactgtgg ggtgctggcc acaaagttga caaaagatgt ttttgagaaa aaaaggaaga    720

aaccaacctg ttcagaaggc tcggactctt cttcccgttc ctcttcctct tcagagtcct    780

cctcagagag tgaagttgag cgagagacaa tcagaaggag aagacataag aggaggccaa    840

aagtcagaca tgctaaaaag agacggaaag aaatgagcag ttcagaagaa ccgaggagga    900

agcgcacagt aagccctgaa ggttattctg agaggagtga tgtgaatgaa aaaagatcag    960

ttgactcaaa cactaaaaga gaaaagcctg ttgtccgccc agaagagatt cctccagttc   1020
```

```
ccgagaaccg atttttactt agaagagata tgcctgctat cactgtggag cctgaacaga   1080
acattccaga tgttgcacct gttgtaagtg atcagaaacc ctctgtatca aagtctggac   1140
ggaaaatcaa aggaagaggc acgattcgct atcacacacc tccaaggtca agatcccact   1200
ctgagtccaa agatgatgac agcagtgaaa cccctcctca ctggaaggag gagatgcaga   1260
gactgagagc ctacaggccc ccgagcggag agaagtggag caaaggagac aagctgagtg   1320
acccctgttc aagccgatgg gatgaaagaa gcctgtccca gagatccaga tcatggtcct   1380
ataatggata ctattcagat cttagtacag cgagacactc tgatggtcac cataagaaac   1440
acagaaagga aaagaagttt aagcataaaa aaaaagctaa aaagcagaaa cattgcagaa   1500
gacacagaca gacaaaaaag aggagaatag ttatgcctga tttggaaccc tcaagatctc   1560
ccacccaccg aatgaagtcc tcttgtgtta gagaaaggag atctcgtgcc tcctcctcct   1620
cctctcatca ctcatccaag cgcgactggt ctaaatcaga ccaggatgac gggagtgctt   1680
caacccattc cagcagagac tcctacagat ccaagtctca ttcacgatca gattctagag   1740
ggagctctag atcaagggct gtgtcaaagt cctcatctcg ttctctcaac agatcaaaat   1800
ctagatctag ttccaggtca ggaccccgaa gaacatcaat atcccccaaa aaacctgctc   1860
agctgagtga aaataagcca gttaagacag aacctttaag gccgtcagtg ccacagaatg   1920
gaaatgtgct agtgcaacca gtggcagcag aaaacattcc tgtaatacca ttgagtgaca   1980
gccctccccc ttctaggtgg aagcctgggc agaagccctg gaagccctct tacgagcgaa   2040
ttcaggagat gaaagctaaa acaacccact tgctgcctgt ccaaagcaca tacagcttaa   2100
caaatattaa agcaaccgtg agttcatcat cttatcacaa aagagaaaaa ccttcagaaa   2160
gtgatgggag tgcttattca aagtacagtg atagaagttc tggaagctca ggaaggtcgg   2220
ggagcaagtc ttctaggagc aggtcatcct ccaggtccta cacaaggtca aggtcaagaa   2280
gtctccctac ttcacgctca ctctctaggt ctccatcatc taggtctcac tcaccaaata   2340
agtacagtga tggttcccag cacagtaggt catcttcata tacttctgtt agcagtgatg   2400
atggaagacg agccatgttt agatccaaca ggaaaaaaag tgtcacttca cataaaagac   2460
atcgcagcaa ctctgaaaag acacttcaca gtaaatatgt cagaggcaga gagaaatcct   2520
cacgtcacag aaagtatagt gaaagtagat catctttaga ttacacttca gacagtgacc   2580
agtcacatgt tcaagtatac tcagccccag agaaggagaa gcagggaaaa gtggaagcat   2640
tgaatgataa gcaggggaaa ggcagagaag aaggaaaacc caagcctgaa tgggaatgtc   2700
ctcgttctaa aaaagagaac tccgaagatc actctagaga tgacagtgtg tccaaaggga   2760
agaattgtgc ggggagtaaa tggattcgg aatcaaactc agaacaagat gtgactaaga   2820
gcaggaaaag tgatccccgg agaggttcag aaaaggagga gggtgaagcc tcttcagact   2880
ccgagtcaga agttggtcag agtcacatca aagccaaacc cccagcaaag cctccaacaa   2940
gcacttttct gcccggcagc gacggtgcct ggaagtctag gagaccacag tcttcagcct   3000
ctgagtcaga gagctcctgc tccaacttgg ggaacattag aggagagccc cagaagcaaa   3060
aacactcaaa ggatgatctt aagggggatc acacaaaaag ggcaagagag aagtcaaaag   3120
ctaaaaaaga caaaaaacac aaggctccaa aacggaagca agctttccac tggcaacctc   3180
cactcgagtt tggtgacgat gaggaggagg agatgaatgg gaagcaagtt acacaggacc   3240
caaaagagaa aaggcatgtc tctgagaagt gtgaagctgt gaaagacggc attccaaacg   3300
tcgagaaaac ctgtgatgaa ggcagttctc caagtaaacc caagaagggt actttagagc   3360
aggacccact tgcagagggt ggacatgatc ccagctcttg tcctgcacct ctgaaagtgg   3420
```

```
aggacaacac ggccagctct ccacctagcg cccagcacct tgaagagcat ggcccaggtg   3480
gaggggagga cgtgcttcag acagatgaca acatggagat ttgcacgcct gataggactt   3540
cccctgcaaa gggagaggtg gtgtcccctt tagcaaacca caggctagac agcccagagg   3600
tgaacattat tccagagcag gatgagtgta tggcacatcc tagagcagga ggagaacaag   3660
agagtagcat gtctgaaagc aagaccttgg gtgaaagtgg ggttaaacag gacagctcta   3720
ccagtgtgac cagtcctgta gaaacttctg gaaagaagga gggggctgag aagagccaaa   3780
tgaacctcac agataagtgg aagccattgc aaggtgtagg gaatctgtca gtgtctactg   3840
caaccacatc cagtgctctg gatgtgaagg cattatctac tgtgcctgaa gtgaaaccac   3900
aaggcttgag gatagaaatc aaaagcaaaa ataaggttcg gcctgggtct ctctttgatg   3960
aagtaagaaa gacggcacgc ctaaatcgaa ggccacggaa tcaagagagt tccagtgatg   4020
atcagacacc tagtcgggat ggtgatagcc agtccaggag tccacacaga tctcgaagca   4080
aatccgaaac caaatctcga cacagaacaa ggtctgtctc atacagtcac tcacgaagtc   4140
gatctagaag ctctacgtca tcttaccgat caagaagcta ctctagaagc cggagcaggg   4200
actggtatag cagaggccga acccgcagcc ggagcagttc ctatggaagt ttccatagtc   4260
acaggacgtc cagcaggagc cggtccagga gcagctctta tgacctccat agccgctcca   4320
gatcctacac ctacgatagc tactacagcc ggagtcgtag ccgcagccgc agccagagga   4380
gtgacagtta ccatcggggt agaagttaca acaggcggtc caggagtggt agatcctatg   4440
gctcagacag tgaaagtgac agaagttact ctcatcaccg gagtcccagc gagagcagca   4500
gatacagctg agatgtctct gtacagattg tgtcttaagt gtaaatacct ggtaacttaa   4560
agcttaagaa actggatggc agtctgttgt gttttagtat tagacctcaa tcctatagtg   4620
gatatttctt gtcacttatt tacatgtgcg caaaagaatt taaagtgcag atgtccctag   4680
aaatatttct atgacccatt ttacagtagg caactatgga attttcattt tcttgaatca   4740
agaaatggta aatttgatgt aagtataatt tgcagtgtca ctgtagatag ggtttttctgt   4800
agatcacatt gtctgtagaa ttcaggtttc tttttgtttc aggttttagc atccatgctg   4860
ccaaacacaa ttatggagag ctgtcacaag acacgtgttc tccatgtccc catgtcccca   4920
tgctggttgt cgtcttggtg tgtgctgtca gatgaggctg tccacatcca tattgaccat   4980
ggccaggtgt gcagggtggt agctcattcc tctgtgtccc agctgtgagc acccacactt   5040
cacagggaat gccagcccag ccaccccagc tcctgctttg gtgcttggtg cctttggttc   5100
ctcgtatacc ctatgtcata ttgtcacata ctgcatttcc tgatgccaga aaatgaattg   5160
tgattttttt tttttaaatt cactggcacc aaaaataatt tcttctgagc tgggttcact   5220
gtgagtgtag ggcttcttc caaacacaga tatgtggtgg aggtcccttg gaacagaacc   5280
tgtatggctg gtcatcttgt tctgcacatg tgtgctaaag tgccgagctg aagaatgtcc   5340
ttcagaagca gctccacaga cactccagcc aagcttcact ctcactgtgg caatagtagc   5400
agccctgccc caaccatcct attccctgtt tgtgtcgaga caccccccac ccccaccccc   5460
acgctgcccc ctgactccat gaagccctgc ctgatggagg aaacccagga caaaagttgg   5520
gggcagcagg gtcacaggct ctgctgcaca gaaaggggtt cttacggctt tgtgtggctc   5580
ctccaggaag aatctaacct gtaaaaacta gtgtgggttt gtttctttgt tttgttttac   5640
tctttagttt gcattctttc cccaagtgta cttaatcacc ttagtgccgg ttaaatccag   5700
ttcacagact tcctgtcagg tatatggtgt agaagtctgt actctcctat cccacccagg   5760
ccttgctagt gcatttggga agagtaaagg ccttgggctg gaggaaatta ctaaagccct   5820
```

```
ggccagatgg aggggaagta ctggatatat gaaagtagtc ttccagggcc atgtggctca   5880

gtgatatata gcatgtgctt agcatgtaag tagctctggg atcagaggtc agcaccccac   5940

aaataaataa tggtgttact ctgtgatgta tgtaagcagc attttggtgg ccagccagct   6000

tattgttcca ccatgtctgt aaattagtta attagaagga taacatcgga actcagtgct   6060

tggcgggtta gacatgtggt ttatagtgag tgggtccttc tacccccccc ccccctttaa   6120

agttgcctac aaagaagggt gtttgaatct agtattcagt aggaagaatg cattcagagc   6180

ccaaataaac tggcaaatgt aattagtaag aaaaggtcac tattgggcca tatattctta   6240

tttggttgct gtgtaacaag ttatcccaaa tttctcagcc taagagtgcc tatgtgtcat   6300

tgacaaacag gcaatggtag ggttgactca tctgctcagg gtctcaaggt aaggtctgga   6360

agagctcatt tctcagaaga ctctgggaag acgtgacttg tagctgggcc cctctagagc   6420

cctcggtgga tgcccacatc gcctgctgta ggccttgcca gcttcaacca gcagggaccc   6480

tttgagtctt gtcttttttt caaaacctct gccctcctcc tgctttaagg gtccatgtaa   6540

gtagatcaga ctccagagat aaatctctac tcgaagtccc gtggccagag gaattacaga   6600

cattgtcggg ttctggggat tagcatagca agaggaaggg catccaccta ccacctactg   6660

ctgcatggac agggcttaac ctgtaccagc aggcactcat gttacgtaat gtcaaccttg   6720

ctgtttatac tcgactgaat acagaaatgg cttttcttct tatccacgat cattctgtat   6780

tttgaagtta ttttttaat aaaattgaat tatgttgtgt aatgtgctta atagaaaatg   6840

ctttctttat tggatgattt tgtaacatcc tgtttactgc aagtggcata gttgatattg   6900

ttcaaaaatg tagaaaatac ttttgtacat actagcaatg tctaatttgt atatacttct   6960

atgaaatttc tctacaactt gaaaaggatc ttgtagaaat gaaaatacat gctgagtttg   7020

agcctaaaaa aaaaaa                                                   7036
```

```
<210> SEQ ID NO 21
<211> LENGTH: 2190
<212> TYPE: DNA
<213> ORGANISM: Mus musculus

<400> SEQUENCE: 21

gaagcaggga cgagtggagg tgccgcaggc tgagtcgcgg ccgggatgtc cgggcagccg     60

ccgccaccgc cgccgcaaca gcagccgccg ccgccgccgc cccccgcctc ggcggccgcc    120

cccgccaccg cgccgcccgg cctggcggtg ggccccggcc cggccgcagg cgtcccggtc    180

ccgggcctgg cggcgggcag cagcgccgct gccccttttcc cgcacggcga ctcggccctc   240

aacgagcagg agaaggagct gcagaggcgg ctgaagcgcc tctacccggc tgtggatgag    300

caggagacgc cgctgccccg gtcctggagc ccgaaggaca agttcagcta catcggcctc    360

tcgcagaaca acctgcgggt gcactacaaa ggtcatggta aaacccccaa agatgcagca    420

tctgttcgag ccacgcatcc aataccagcg gcctgtggga tttattattt tgaagtaaaa    480

attgtcagta agggaagaga tggctacatg ggaattggtc tttctgctca aggtgtgaac    540

atgaatagac taccaggttg ggataaacat tcatatggtt accatgggga tgatggacat    600

tcattttgtt cttctggaac tggacaaccg tatggaccaa cttttacaac tggtgatgtc    660

attggctgtt gtgttaatct tatcaacaat acctgctttt acacgaagaa tggacatagt    720

ttaggtattg ctttcaccga cttaccgcca aatttgtatc ctactgtggg gcttcagaca    780

ccaggagaag tggttgatgc caactttggg caacatcctt ttgtgtttga tatagaagac    840

tacatgcgag aatggagaac caaaatacag gcccagatag accgctttcc tatcggggat    900
```

```
cgagaaggag aatggcagac catgatccaa aaaatggttt catcttattt agtccaccat    960

gggtactgtg ccacagcaga ggcctttgcc agatctacag accagactgt tctagaagaa   1020

ttagcttcca ttaagaatag acaaagaatt cagaagttgg tgttagcagg acgaatggga   1080

gaagccattg aaacaacaca acagttatac ccaagtttac ttgaaagaaa tcccaatctc   1140

cttttcacat taaaagtacg tcagtttata gaaatggtga atggtacaga cagtgaagtg   1200

cggtgtttgg gaggccgaag tccaaaatct caagacagtt atcccgtcag tcctcgaccc   1260

tttagtagtc caagcatgag ccccagtcat ggaatgagta tccacagctt agcaccaggc   1320

aaaagcagca ctgcacattt ttctggtttt gaaagttgta gcaatggtgt aatatcaaat   1380

aaagcacacc aatcatattg ccatagtaaa caccagctat ccagcttgac tgtaccggag   1440

ctaaacagtc tcaatgtatc aaggtcacag caagttaata actttaccag taatgatgta   1500

gacatggaaa cagatcacta ctccaatgga gttggagaaa cttcatccaa tggtttccta   1560

aatggtagct ctaaacatga ccacgaaatg gaagattgtg acaccgaaat ggaagttgac   1620

tgcagtcagt taagacgcca gctgtgtgga ggaagtcagg ctgccataga gaggatgatt   1680

cactttggcc gagagctaca agccatgagt gagcagctga ggagagaatg tggcaagaac   1740

acagcaaata agaaaatgct gaaggacgca ttcagcttac tagcatattc ggatccttgg   1800

aatagtccag ttggaaatca gcttgaccca attcagagag aacctgtgtg ctcagctctt   1860

aacagtgcaa tattagaaac ccacaatctg ccaaagcaac ctccacttgc cctagccatg   1920

ggacaggcca cacagtgtct aggcctgatg gctcggtcag gagttgggtc ctgtgcattt   1980

gccacagtgg aagactacct acattagcta tgcacttcaa gagctcacac tcacattgtg   2040

gcaaacagtc aacatggaag tagaccggct ctgctgattt gaaatttaga ttttttttta   2100

attatgtact ggggacaggt ttttgtcgct ttacattgct tcctagtttt acagcatgat   2160

gcaaatgaat tttctaactt agtgtttagg                                    2190
```

<210> SEQ ID NO 22
<211> LENGTH: 857
<212> TYPE: DNA
<213> ORGANISM: Mus musculus

<400> SEQUENCE: 22

```
gcagtcacgt gaggcgctaa gatggcggcg tcccagcgac caagttggtc cgagtcgaag     60

gttgctggtg ttgtgcagga gggaaatagg gaagcacccc aggacatcaa gatggcactt    120

tataaacatg gtcagctgat tccttcccta ggagatgcaa agttcagaag cccgataatc    180

tctgaaatta tagaaaagaa gtttgaacat tatagaaacg acaagacttt aaatatacat    240

ggaactttgg tctttggaac aagtagtagt ttgtctggca taatggcaaa cttagttttc    300

cgaaacagtt tcaaggttaa atatgaagct ttgaagacct atgcatccct gactacactt    360

ccagttttgg ctaccatcgt ttcttacaag ctctttgtaa cagatgcttt gcaatcaggt    420

gacataagca aggaaagctg tgttctgagg agcgcactaa ttggcatggc atgcggcgtt    480

tcctacccca gtgctttggc tttctataaa aatggacgtt tggcagttaa gtatcagact    540

gttccactgc caccaaaggg aagagttatg ctccattggt tgctcctttg tcaaactggg    600

atgaaagcaa tggctattcc tctgttcttt cagatagtaa tgggagcttt tactggctta    660

catcattaca atatatgtga aaaaccacgt gcaaggcttg tgcctgatga ttaaccaaag    720

actccatgga ctccatggaa gccggttcaa tggcatgaac ttctttatag acggactttg    780

ccactggtct aagagggaaa aggaactttt gcctggcata tatcagacac tcagtaatta    840
```

```
tgaatgttat aaatgtt                                                 857

<210> SEQ ID NO 23
<211> LENGTH: 1146
<212> TYPE: DNA
<213> ORGANISM: Mus musculus

<400> SEQUENCE: 23

tggacccagc tgaggagcga agagctgctg gcagcgccga ttcccagcac gccgcttttt     60

agaacttcag ttgtcaaaat gggcagaatc tttcttgacc atatcggtgg tacccgtctg    120

ttttcttgtg caaactgtga tacaatcctg accaatcgct cagaactcat ctctactcgg    180

ttcacaggcg ccactggtag agcatttctt tttaacaagg tagttaactt gcagtacagt    240

gaagttcaag atcgggtcat gctcactggc cgccacatgg ttcgagatgt gagctgcaaa    300

aactgcaata gcaaactggg atggatctat gagtttgcta ctgaagacag ccagcgttat    360

aaggaaggcc gtgtgatcct ggaacgtgca ctagttcgag agagtgaagg ctttgaagag    420

catgtaccat ctgataactc ttgaagaaaa aagataaatc catcttttcc caggtctcct    480

tcactgaaaa caaaatctcc ttacatacac tgtcacctta gcatcagaat cggattcatg    540

aactgcggaa caagaggttt tgagaatcta agatggaacc ttttttctt tcttttttt    600

ttttaaattt ggtattttcc aacccaacag cagtttgtag agagaatttt atgcataggc    660

tggtaatttt ttccctgtgt ttacatcttg agacagaaga gtttgcagct acatggttgg    720

ctatgtgagg gaaaaaaatt ggggtcctta gagtgaaaag gagtgttttg tgtatatttt    780

gagtggagaa tatgtcaaga gcatggtttt taaatttatt tgggctttat ttaaaatttt    840

ctttttaacc cagttatttc acttaatttg ctagcttcaa gaagagatcc gaatctgtgc    900

ccagcgctgg aggctcagtg ttagcatggc ttgtgctggc cagtgtgcca tattcttgtt    960

ggagaggaac tgtagcacca gaacccattc ttccttgtca gtcttgaccc acagatgtca   1020

ccacccctag ttccttgtca ccatggactt ggtgttgatt ggaaactttc tgaaatgggg   1080

cagaactgct tggttgtctt ttcccatgta acttaagcat agtaatataa ataaagtggt   1140

agttgg                                                            1146

<210> SEQ ID NO 24
<211> LENGTH: 966
<212> TYPE: DNA
<213> ORGANISM: Mus musculus

<400> SEQUENCE: 24

aaaatgagta ctacatggct atttacgaat gggaagaata aggcttaact tttaatgtaa     60

ttaaatctgt gcactacatt cctgagcaat gagcagaatg tattttaagt atgtattaaa    120

tatttgaaat tataaatcta ggccgctgta gcccgcatcc agaggcaggg gcagctaggt    180

ttctttgagt tagagaccag cctggtctag gtagtaagtt ccaggactac cagagctgtg    240

cagcgagact gtctcaaaaa ccaaaccaaa ccaaaaccca acccaaacca aacaaagcca    300

aacaacaaca acaaaaacaa aaaaacccac caaaaaaacc aaggaaacaa aacaaccaaa    360

aatcaaaaaa ctaggctact ttaaaatgtc attatttatt ttgttaaaat tcctgagata    420

aacactattc taacaaaaga gccattaaga ctaagaatct ctaagatagt tttatgttc    480

tcaaattcag aagaactaaa cacattattg cagtattaat aaaataaaaa ctcaagataa    540

gaaggtcaaa tgtgtccaag ataattgtct cctccacaat gaggcaaatc cataaggaat    600

aatgggggga agttcaatgc attagctttt gacagtcaaa acaggaacct ttaaaatact    660
```

```
ctgttcatgg ttaaaaataa tttgtactct aagtccagtg atcattgcca gggagaacca    720

aagttgagaa atttctatta aaaacatgac tcagaggaaa acatacaggg tctggtcatg    780

aaggaaatga tctggccccc attggtcact cctacagtca catggtcagg gcatctttaa    840

aagtgagcta tctggacttc agaggctcat agcaccctcc tgtgctgcag cctttctcac    900

ctggaagaca gctcctcctc gaaggtttac aaaatgtgtg atgcctttgt gggaacctgg    960

aagctt                                                               966
```

```
<210> SEQ ID NO 25
<211> LENGTH: 564
<212> TYPE: DNA
<213> ORGANISM: Mus musculus
<220> FEATURE:
<221> NAME/KEY: misc_feature
<222> LOCATION: (433)..(488)
<223> OTHER INFORMATION: Wherein N=A,T,C or G

<400> SEQUENCE: 25

tcaaaataca aacatagact ttattaaatg ctgctcaatc ctcagtaaag atctctcatt     60

ataaaacagt tttccataca actgcaaggc aagaggctgg aatggtactg gtaacaacag    120

tgtgaaaaat acctgaccag gtaaaaacag acaaagcttc tacatagtca gctctgagga    180

cacctgctgc agttccttta aataaagcca ggcagtgaca gctagcagtc tgcatcacac    240

tgtgggaggg acccaaagct ccaccctgca ggcaggcagg cctggggact ggcagggtga    300

ggactgggaa ggccctgcct ccagccttgg aggagaggaa tgaaggaggt gagcctcggg    360

tccacccgtg gcctgtgctg ctccgcacac gctccgggga gccgctgctg aaggggggat    420

ttgggaacat canaattttg gtttacttcc cccccccaac tttaatactt tgtgcttcag    480

aagcctgnaa atgtcagatg ttgtaaaacc cagagtatgg cagtgtcttt aatgaggctg    540

ggctcttgtc ccctgcccac acct                                           564
```

```
<210> SEQ ID NO 26
<211> LENGTH: 399
<212> TYPE: DNA
<213> ORGANISM: Mus musculus

<400> SEQUENCE: 26

atgtgtgatg cctttgtggg aacctggaag cttgtctcca gtgaaaactt cgatgattac     60

atgaaagaag tgggagtggg ctttgccaca aggaaagtgg caggcatggc caagcccacc    120

atgatcatca gcgtaaatgg ggatttggtc accatccggt cagagagtac ttttaaaaac    180

accgagattt ccttcaaact gggcgtggaa ttcgatgaaa tcaccgcaga cgacaggaag    240

gtgaagagca tcataaccct agatggcggg gccctggtgc aggtgcagaa gtgggatgga    300

aagtcgacca caataaagag aaaacgagat ggtgacaagc tggtggtgga atgtgttatg    360

aaaggcgtga cttccacaag agtttatgaa agggcatga                           399
```

```
<210> SEQ ID NO 27
<211> LENGTH: 2113
<212> TYPE: DNA
<213> ORGANISM: Mus musculus

<400> SEQUENCE: 27

tggcggtggc ctgagcagcg cgagtgtgat gaggctgccc tgcctcgcag ctccgctcgc     60

agccagctga cagcgcctgc cctcagcaca cccggagggg agccgcgggg ccgtgacctt    120

ggccgaggag ggcagattga tcatccttgt atctgagcta ccaagttctg ggtgaaatgg    180
```

```
ctcagggaaa taattatgga cagaccagca acggggtggc ggacgaatca cccaacatgc    240

tggtgtacag aaagatggaa gatgtcatag cacgtatgca agacgagaaa aacggaattc    300

ccatccgtac cgtcaaaagc ttcctttcca agatccccag tgtcttctcc gggtcagaca    360

ttgttcaatg gttaataaag aacttaacta tagaagatcc agtggaggct ctccatttgg    420

gaacgctaat ggctgcccat ggctacttct ttcccatctc agatcatgtc ctcacactca    480

aggatgacgg caccttctac cggtttcaga caccctattt ttggccgtca aattgttggg    540

agccagaaaa cacagactat gctgtttacc tctgcaagag aacaatgcaa aacaaggcaa    600

ggctagagct agcagattat gaagccgaga gcctggccag gctgcagaga gcatttgccc    660

ggaagtggga gttcattttt atgcaagcag aagcacaagc taaagtggac aagaagagag    720

acaaaattga aaggaagatc ctcgatagtc aagagagagc attctgggat gtccacaggc    780

ctgtgcctgg atgtgtaaat actacagaag tggacattaa gaagtcatcc cggatgagaa    840

acccacacaa aacacgaaag tctgtctatg gtttacaaaa tgacatccga agtcacagtc    900

ccacccacac acctacacca gaaaccaagc ctcctacaga agatgagctg caccaacaga    960

taaaatactg gcaaatacag ttagatagac atcggttaaa aatgtcaaaa gttgctgata   1020

gtctactaag ctatacggaa cagtatgtag aatatgaccc atttcttgtg ccgcctgacc   1080

cttccaatcc atggctttca gatgatacga ctttctggga acttgaagca agcaaagaac   1140

caagtcaaca gagggtaaaa cgatggggtt ttggtatgga tgaggcattg aaagacccag   1200

ttgggagaga gcagttcctt aagtttctag aatcagaatt cagctcagag aacttaaggt   1260

tctggttggc agtggaggac ctgaagagaa ggcctatccg agaggtcccc tcgagagtgc   1320

aggaaatatg gcaagaattt ctggctcctg ggcccccag tgccattaac ttggattcta   1380

agagttatga caagaccaca cagaatgtga aggaaccagg acgatacaca tttgaagatg   1440

ctcaggagca tatttacaag ctgatgaaga gcgactccta cccccgcttt ataagatcta   1500

gtgcctacca ggaacttcta caggcaaaga gaaagggaaa aactctcaca tccaagagct   1560

taacaagcct tgttcagtct tactagaagg accgtctttg tcacatgagt gctgaacgga   1620

gccatcgccc ataccttgta gcccatcgct gttacctgga gccaaggacg ttagaccaag   1680

atgttgcatg aacaaaggac tggaattgtt cttttctgtg tgcacataaa gtcatcacac   1740

ttgccaaggg acgctgtcat ttcattgcct tcatcttcat gtgtcgtctg cttccctctc   1800

tcctcgtgct aagctggatc cgtgtccttt tctttttaac gagttcaagt gaacgaaaac   1860

ttatttcccc cccttcctct ccttttcttg aagcttctgc tagatgaaaa ttcactgaaa   1920

attcagtcag tcacaaactg gaagaattgt aaaagaaaaa aaaagtatat atcactaagt   1980

acacacatgg cttcacactt attaactaat aaattggcac agaaggtgtc gtttcaccct   2040

tgtatccaca gtctgaagca agcacccatt ttcatctgtt ctccggacat tgtctgttcc   2100

tgtttcttgc aca                                                      2113
```

```
<210> SEQ ID NO 28
<211> LENGTH: 1657
<212> TYPE: DNA
<213> ORGANISM: Mus musculus

<400> SEQUENCE: 28

aaaacatgga gtcagctccg gcagccccg accccgccgc cagcgaaccg ggcagcagcg      60

gctcggaggc ggccgcgggc tccagggaga ccccgctgac ccaggacacg ggccgcaaga    120

gcgaggcacc gggcgcgggg cgcaggcaga gctatgcgag ctccagccga ggtatctcag    180
```

```
tcacgaagaa gacacacaca tctcaaattg aaattattcc atgcaagatc tgtggagaca    240
aatcgtcagg aatccattat ggtgtcatta cgtgtgaagg ctgcaagggc tttttcagga    300
gaagtcagca gagcaatgcc acctactcct gtcctcgtca gaagaactgt ttgattgatc    360
ggaccagcag aaaccgctgc cagcattgtc ggctgcagaa atgcctggcc gtggggatgt    420
ctcgagatgc tgtcaagttt ggtcggatgt ccaagaagca gagagacagc ttgtacgccg    480
aggtgcagaa gcaccggatg cagcagcagc agcgagacca ccagcagcag cctggggagg    540
cggagccgct gacgcccacc tacaacatct cagccaatgg gctgacggaa ctgcatgatg    600
acctcagcac ctatatggat gggcacaccc ccgagggcag caaggccgac tcagccgtca    660
gcagcttcta cctggacatc cagccctccc cagaccagtc gggattggac atcaatggga    720
tcaaacccga acccatatgt gactacacac cagcatctgg cttcttcccc tactgttcct    780
tcaccaacgg agagacttcc ccaaccgtgt ccatggcaga actagaacac cttgcccaga    840
acatatccaa atcccacctg gaaacctgcc agtacttgcg ggaagagctc cagcagataa    900
cgtggcagac cttcctgcag gaggagattg aaaactacca gaacaagcag agagaggtga    960
tgtggcagct gtgtgccatc aagattacag aagctatcca gtatgtggtg gagtttgcca   1020
aacgcattga tggatttatg gagctgtgtc aaaatgatca aattgtgctt ctaaaagcag   1080
gctcgctaga ggtggtgttt attaggatgt gccgtgcctt tgactctcag aacaacaccg   1140
tgtactttga cgggaagtat gcgagccccg atgtcttcaa gtccctaggt tgtgaagact   1200
tcatcagctt tgtgtttgaa tttgggaaga gtttgtgttc tatgcacctg accgaagacg   1260
aaatcgcgtt attttctgca ttcgtactga tgtcagcgga tcgctcgtgg cttcaggaaa   1320
aggtaaaaat agaaaagctg caacagaaaa ttcagctggc ccttcagcac gtcctacaga   1380
agaaccaccg agaagatgga attctaacca agctaatatg caaggtgtct acgttaagag   1440
ccctatgtgg acgacatacg gaaaagctaa tggcatttaa agcaatatac ccagacattg   1500
tgcgactcca ttttcctcca ttatacaagg aattgttcac ttcagaattt gagccagcca   1560
tgcaaatcga tgggtaaatg tcgcgcccga gcacttctag aacatctgga gtacaaacat   1620
gaaagtaaga gagaaaattt ttaaaaaaaa aaaaaaa                            1657
```

```
<210> SEQ ID NO 29
<211> LENGTH: 2567
<212> TYPE: DNA
<213> ORGANISM: Mus musculus

<400> SEQUENCE: 29

aattcagggt aggggtttc tactgaggac tttttcttct tcacagctgc cttctgaaat      60
gtgtggagca actggtggat ggtttcctag cctttcaaag gtagtttaca aatgatttga    120
agtgctgatc ctttcagagt ctcaacagat tatttcttaa acagctcata cattgctgtt    180
tatgcatgaa ttagaaccgg gccacgtaga aaacactgtg attgtacctg ggagttggcg    240
agaaaaccag tgctctccct tgattctgct gcacgaggag aatgggctgt gatcggaact    300
gtgggctcat tgctggagct gttattggtg cagtcctggc tgtgtttgga ggcattctca    360
tgccagtcgg agacatgctt attgagaaga caatcaaaag ggaagttgtc cttgaagaag    420
gaaccactgc tttcaaaaac tgggttaaaa caggcaccac tgtgtacaga cagttttgga    480
tctttgatgt gcaaaaccca gatgacgtgg caaagaacag cagcaaaatc aaggttaaac    540
aaagaggtcc ttacacatac agagttcgtt atctagccaa ggaaaatata actcaggacc    600
ccgaggacca cactgtgtct tttgtacagc ccaatggagc catctttgag ccttcactgt    660
```

```
ctgttggaac agaggatgac aacttcacag ttctgaatct ggctgtagca gctgcaccac    720

atatctacca aaattcattt gttcaagttg tgctcaactc tcttataaaa aagtccaagt    780

cttctatgtt ccaaacaaga tctttgaaag aactcttgtg ggttacaaa gatccattcc     840

tcagtttggt tccatatcct ataagtacca cagttggtgt gttttatcct tacaatgaca    900

ctgtagatgg agtttataaa gttttcaatg gaaaggataa cataagcaaa gttgccataa    960

ttgagtccta taaagggaaa aggaatttgt cctattggcc aagctattgc gacatgatta   1020

atggcacaga cgcagcctcc tttccacctt ttgttgaaaa gtctcggaca ttgagattct   1080

tttcctctga catttgcagg tctatctacg ctgtgttcgg atctgaaatc gaccttaaag   1140

gaatccccgt gtacagattt gttcttccag ccaatgcctt tgcatcaccc ctccagaatc   1200

cagacaacca ttgtttctgc actgaaaaag taatctccaa taactgtaca tcttatggtg   1260

tgctagacat tggcaaatgc aaagaaggaa agcctgtgta tatttcgctt ccacatttcc   1320

tacatgcaag tccagatgtt tcagaaccta ttgaaggctt acatccaaat gaagatgagc   1380

ataggacata cttagatgtg gaacccataa ctggattcac tctacaattt gcaaaacgac   1440

tgcaggtcaa catattggtc aagccagcta gaaaaataga agcattaaag aatctgaaga   1500

gaccttacat tgtacctata ctgtggctaa atgagactgg gaccattggt gatgaaaaag   1560

cagaaatgtt caaaacacaa gtgactggga aaatcaagct ccttggcatg gtagagatgg   1620

ccttacttgg gattggagtg gtgatgtttg ttgcttttat gatttcatat tgtgcttgca   1680

aatccaagaa tggaaaataa gtagtggatg agcctacata tacactggct acatctttgg   1740

taaagccgat cacaaaatga aaacttaata tatgcttcgt tttacaaaa cacacctatc    1800

tttaggagaa gaaatggtgg tgtgtgctct ctctctcttt ctctttctct cttattgcag   1860

atatatattt atttgtaaat atatatatat gcaataagtc acagcatatt tcaaaagatt   1920

aatatgtcac tataggcaat attttttaat aaaatcttgc acttttatta aaagtccatc   1980

atttgcaact gagtggactt caatttctgt agacccaatt atcctgtttg gttctgattt   2040

actgatttgt tccatgttgg caaatttcaa gaatgtacat tctgagaaat ttttgttttc   2100

cctcactgga ggaaactgct atcatgactg gggtggcccc tttgtttata gcaaatttgg   2160

cttgcaactg tcagcacatg gcataagtat aacatcttga aagacttaag aatgaaaaat   2220

gaacaattca catgtgagcc actgcttata tattaagtct ctccctctct ggagttcttg   2280

gctacagcaa ggccagatat cacattggtt ttggttttgt tgtttttgtt ttgtttttgt   2340

tttttactct ctgacacaga gcttatgaaa tggacttttt tttttttttt tttttagcat   2400

accttagctc tttgtatttt aagtatgtcg tcatgttcca tgctgcatag ctctttaaaa   2460

aacctgagta ggtttttctc tttctgctca gctgcaacta ataacaacct tggagagctg   2520

ttatagtgtt aaaagatgta aatgataata aaagaattat taaatgg                 2567
```

<210> SEQ ID NO 30
<211> LENGTH: 1649
<212> TYPE: DNA
<213> ORGANISM: Mus musculus

<400> SEQUENCE: 30

```
gagctgtgct tgtctaggtt ggcgctgaag gatacacaga agcaaatgca cagatcggag     60

atgactccca cgggggcagg cctgaaggcc accatcttct gcatcttgac ctgggtcagc    120

ctgacggctg gggaccgcgt atacatccac cccttccatc tcctttacca caacaagagc    180

acctgcgccc agctggagaa ccccagtgtg gagacactcc cagagtcaac gttcgagcct    240
```

```
gtgcccattc aggccaagac ctcccctgtg aatgagaaga ccctgcatga tcagctcgtg    300
ctggccgccg agaagctaga ggatgaggac cggaagcggg ctgcccaggt cgcaatgatc    360
gccaacttcg tgggcttccg catgtacaag atgctgaatg aggcaggaag tggggccagt    420
ggggccatcc tctcaccacc agctctcttt ggcaccctgg tctctttcta ccttggatcc    480
ttagatccca cggccagcca gctgcagacg ctgctggatg tccctgtgaa ggagggagac    540
tgcacctccc gactagatgg acacaaggtc ctcgctgccc tgcgggccat tcagggcttg    600
ctggtcaccc agggtgggag cagcagccag acacccctgc tacagtccat tgtggtgggg    660
ctcttcactg ctccaggctt tcgtctaaag cactcatttg ttcagagcct ggctctcttt    720
acccctgccc tcttcccacg ctctctggat ttatccactg acccagttct tgccactgag    780
aaaatcaaca ggttcataaa ggctgtgaca gggtggaaga tgaacttgcc actggagggg    840
gtcagtacag acagcaccct acttttcaac acctacgttc acttccaagg aacgatgaga    900
ggtttctctc agctgcctgg agtccatgaa ttctgggtgg acaacagcat ctcggtgtct    960
gtgcccatga tctccggcac tggcaacttc cagcactgga gtgacaccca gaacaacttc   1020
tccgtgacgt gcgtgcccct aggtgagaga gccaccctgc tgctcatcca gccccactgc   1080
acctcagatc tcgacagggt ggaggccctc atcttccgga acgacctcct gacttggata   1140
gagaacccgc ctcctcgggc catccgcctg actctgcccc agctggaaat ccgaggatcc   1200
tacaatctgc aggacctgct ggctgaggac aagctgccca cccttttggg tgcggaggca   1260
aatctgaaca acattggtga caccaacccc cgagtgggag aggttctcaa tagcatcctc   1320
ctcgaactca aagcaggaga ggaggaacag ccgaccacgt ctgtccagca gcctggctca   1380
ccggaggcac tggatgtgac cctgagcagc cccttcctgt tcgccatcta agagcaggac   1440
tcaggcacgc tgcactttct gggcagagtg aataaccccc agagtgtggt gtgaggcctt   1500
gtgcctagcc catggagaca aggccggtgt cggagaaccg ttctgggcaa aactcagtgc   1560
tgtcacccct ggctccccat cacgccttgt agcgcggcag aggccgtctc cttggagact   1620
gcgctgaccg agaataaatg atgagcagc                                     1649
```

<210> SEQ ID NO 31
<211> LENGTH: 1239
<212> TYPE: DNA
<213> ORGANISM: Mus musculus

<400> SEQUENCE: 31

```
gatgaccgca acagtagttg ctgcggctgc cactgcaacc atggtctcca gcagcagcgg     60
cctcgccgcc gcccgcctgt tgtcgcgcac cttcctcctg caacagaatg ggatacgaca    120
cgggtcttac acagcctctc ggaaacatat ctatattgat aaaaatacga agattatttg    180
ccagggtttc acaggcaaac agggtacctt tcacagtcag caggctttgg agtacggcac    240
caaactcgtg ggaggaacca ctccagggaa gggtggccag aagcacctgg gcttgcccgt    300
ctttaatact gtgaaggaag ccaaagagaa aacaggagca acggcttctg tcatctatgt    360
ccctcctcct tttgctgctg ctgccattaa tgaagcaatc gacgcggaga ttcccttggt    420
tgtgtgcatt acggaaggta ttccgcagca ggatatggtg cgggtcaagc acagactgac    480
acgccaggga acgacgaggc taatcgggcc aaactgcccc ggcgtcatca accctggaga    540
atgcaaaatc ggcatcatgc ctggccacat tcacaagaag ggaagaatag gtatcgtgtc    600
caggtccggt actctgactt atgaagcagt tcaccaaaca acccaagtcg gattggggca    660
gtccttgtgt attggcattg gaggtgaccc ttttaatggg actgatttta ttgattgcct    720
```

```
tgaagtcttc ctgaatgatc cagccacaga aggcatcata ctgattggtg aaattggtgg    780

tcacgctgaa gaaaatgctg ccgcgtttct gaaggagcat aactcaggtc caaaggccaa    840

gcctgtagtg tccttcattg ctggtataac tgctcctcct ggcagaagga tgggccatgc    900

aggggcaatt attgctggag gaaaaggtgg cgctaaagag aagatctctg ctcttcagag    960

tgctggggtg gttgtcagca tgtcccccgc acagctggga actaccattt ataaggagtt   1020

tgaaaagagg aagatgcttt gaaggacaca acaagaaatt ctttaaagct gtggaagaaa   1080

tctagacgtg agggccagtc caggctgtca gcccatgcag ctgacactgg ttggtctctc   1140

agtatgtggg aaatccaggc aagttttaga atgtcctaaa ttgagctatt ttcacttact   1200

gtgtaacaga gacagataat aaatctatca tttgatttg                          1239
```

<210> SEQ ID NO 32
<211> LENGTH: 1787
<212> TYPE: DNA
<213> ORGANISM: Mus musculus

<400> SEQUENCE: 32

```
ggggccctct ttccgacctg cccacggccc cgcccacctg aatgtaggtg aaaggtcggc     60

ggagccgctc gggcagcgga gcaagaccaa gactgcccgg agctgacaga cagacagaca    120

gaagactgag catggcagac gagccgaaac ccatcagtcc gtttaagaac ctcctggctg    180

gcggcttcgg cggcatgtgc ctggtgtttg tggggcaccc cctggacacg gtcaaggtcc    240

gactgcagac acaaccacca agtttgtctg gacagccacc tatgtactct gggaccttgg    300

actgtttccg gaagactctt atgagagagg gcatcacagg gctgtatcgg ggcatggctg    360

cgcccatcat tggagtcacc cctatgttcg ccgtgtgctt ctttgggttt ggtctgggga    420

agaaactaca gcagaaatct ccagaggatg aacttagcta cccacagctg tttacagctg    480

ggatgttatc tggtgtgttc accacaggaa tcatgacccc tggagaacgg atcaaatgct    540

tactgcagat tcaggcttct tcaggggaga acaagtacag tggcaccttg gactgcgcaa    600

agaagctgta tcaagagttc gggatccgcg gcttctacaa agggactgtg ctcacactca    660

tgcgagatgt tcctgccagt gggatgtatt tcatgacata tgaatggctt aaaaatctct    720

tcactccaga ggggaaaaga gtggtcagtg acctcagcgt gcctcggatc ctggtggctg    780

gtggctttgc agggatcttc aactgggccg tggcaatccc cccggacgtg ctcaagtctc    840

gattccagac tgcacctcct ggaaaatatc ctaatggttt cagagatgtg ttgagagagc    900

tgatccgaga agaaggagtc acctccttgt acaaagggtt caatgcagtc atgatccgcg    960

ccttcccagc caacgccgcc tgtttccttg gctttgaaat tgccatgaag ttccttaatt   1020

ggattgcccc caacttgtga agctgaagac tcttcaagac ctgtggaagc tggacactgt   1080

tgctgagagg caggggcagg aggaggaagt cctgagaggg aggggaggga agaggtgtga   1140

tcagagctcc aggcttggct gtgatggtga aactgttgcc ttaatgatat cctctacctt   1200

gtataacttg gtgccatttt gaaacttgaa tttagaggat ttccagagaa ttggagatgg   1260

aataaatagt ttatagactc gataccttttg gccaaattgc cacctactgg ttgactgaag   1320

gccctgttac actcaaaata ctccttcccg aagaggtgat ggctgactct ctggaggccc   1380

cttgcctact ttcagccagc taaaccagga gctgggatct ttaattgcta gccaggaaaa   1440

ctcaagagat gtctctggtg ccatccatat actcctggct gtgcatggga tgtgggtgtg   1500

aaccacacat ctgtctatcc aatggactgg gtagataata cctaagaaca gcccacctac   1560

taaccatttt tttttgatat ttttacacaa gaaataataa gaagaaagct acaattgtct   1620
```

```
aaatccccag gagaaagtag agaattttcc ctcctacaca gtgaagacag tcccagcctc   1680

ctgggataag tgtgagagcc ataatgtatg aaggctcctt ttgcacattc tttccccatg   1740

agagcactca gttttaacag gaaacaataa atattgtttc taatttt                 1787
```

<210> SEQ ID NO 33
<211> LENGTH: 1169
<212> TYPE: DNA
<213> ORGANISM: Mus musculus

<400> SEQUENCE: 33

```
cggacgcgtg ggcggacgcg tgggtaagtt tccgcgtttc tctcaaccgc agccagcagt     60

gaaaatgtca gcgccagagg gtctgggaga tgctcatggc gacgccgacc gcggcgacct    120

ttccggggac ctccgtagtg tgctggtcac gagcgtgctc aacctcgagc cgctagatga    180

agatctctac agaggaaggc attactgggt acctacctcc cagcggctct ttgggggtca    240

aattatgggc caggccctgg tggctgcagc caagtctgtg agtgaagacg tccatgtcca    300

ctccctgcac tgctactttg tccgggcagg ggacccgaaa gtgccagtgc tgtaccacgt    360

agagaggata cggacaggag ccagcttctc agtgcgcgcc gtgaaggctg tgcagcatgg    420

caaggccatc ttcatctgcc aggcctcctt ccagcagatg cagcccagcc cgctgcagca    480

ccagttctcc atgccctccg tgcccccgcc agaagacctg ctggatcacg aggccctcat    540

tgaccagtac ttaagggacc ctaaccttca caagaagtat cgagtggggc tgaaccgagt    600

tgctgcccag gaggtaccta ttgagatcaa ggtggtgaac ccacccaccc tgacccagct    660

gcaggcactg gagcccaaac agatgttctg ggtgcgtgcc cggggctaca ttggggaagg    720

tgacatcaag atgcattgct gtgtggctgc ttatatctct gactacgcct tcctgggtac    780

agcactgctg ccccaccagt ccaagtataa ggtgaacttc atggcgtcac tggatcactc    840

catgtggttt catgccccat tccgagccga ccactggatg ctgtacgagt gtgagagccc    900

ctgggctggt ggctctcgag ggctggtgca tgggcggctg tggcgtcggg atggggtcct    960

tgctgtgacc tgtgcccagg agggtgtgat ccgattgaag cctcaggtgt cagagagtaa   1020

gctatagtga aagatgcctg gctcggcctg gggctaaaag gactttgcac tgccatttct   1080

gaggcaggag tcacagttga gagctgggct tcctgcctct tacatacaat aaagagattg   1140

ctaacactgg aaaaaaaaaa aaaaaaaaa                                     1169
```

<210> SEQ ID NO 34
<211> LENGTH: 2795
<212> TYPE: DNA
<213> ORGANISM: Mus musculus

<400> SEQUENCE: 34

```
ggcttcccga agtctcctgc tgctagtaag aggaagtact gcagggctga tgtcgcgacc     60

ttgtggactc ccggagcctg tcaggtaaag ctctccggct ccaagcaccg gagcctgacc    120

aagccgggct ctgatcattg cacaggccct atctatccac cctgcagttc aggctcctca    180

gggctcccct ccagccggaa ctttgctctt ctgctcctgg ggacagagtt ggggtttcca    240

cctaacaaga ttcacacacg cgcaggcgtg tcctcatctc ccagggtcac agcgtttccc    300

ttttgccaat ccgagtcact cttcaggaac ccccacagcg gaacctcaga accccaacat    360

ggccagacag ttatgcatca gccaaacaga gttcaagttc ctgggtggct tcttccaccc    420

ataaccgagg ttcttgctca aggcattgct gctcccagcc tggcctcagt actacaaggc    480

tgttctgaga actcaacaca gaatgggcca gccctgctcc tattttgatg gtattgtctc    540
```

```
gacacaatta gacttttatt ttcctgctgc ctctgggcag ttctaggggt tgtttaaaag    600
ccttcttcct ctttggctgg ctaattgtct tttctggaca gaggcctgtg agtatcagct    660
gtactgtgtg ccagctttca ttggcccttt ccaggacatt tgattggttt gcagccagct    720
ctctgtcaca tggatgggat ggggcttgtg gggggggggg cggtgtttga gaataagcaa    780
acccctctaa ccaaaggctt gttaaggatg cgctagtgat taacactcac agctcagggc    840
caccttgttc atgaactggc cactttacct gcacggctac cctcgagcaa gttacagatg    900
aggacttctc gaggctccag gagatgatgg gtagcccagg ctgatctcaa actttcggta    960
gtcgttctgc ctcagcttct ccaagcacta ggaggttgca ggtgtgagct agttaccgca   1020
cccggctcca cccagctttt gagatggaat gagttctggc tgacctaaac atctggtttt   1080
gcacagtcat actgcggaat agtgagaact aatgttacac tttctacagc cactgtgaca   1140
aagtcctacc aactggatga cttgaggaat agcaattagc ctctcttggg tctgaaggac   1200
ccataatcag gtctgaagtc cataatcaag gtattagcag gcacacaatc agaagtctct   1260
ggggatgttc cattgcccct tccagcttct ggtaactttc gatcatcctt ggcttatagc   1320
agcagatttt gggtccccat tcccatctgt ctgtctgtct gtctgtctct ctgtgtgtgt   1380
gtgtgtgtgt gtgtgtgtgt gtgtgtgtgt gtgtgtgtgt acatctatgt ctatagcctc   1440
ttccttcaaa gacacctgtt gttggattgg gagttctccc tacattcagg atggtgcaat   1500
ctcaagagcc ttaactactt acatctgcaa agaacccatt tctgaataac accacattct   1560
caggctctat gttgacatga ataaggtggt cactgtcaca caccatgcaa acaagcagca   1620
taaagcatag agctcatccg agggactcgg aaagagccac atgaaaacag tcccatttgt   1680
ggtgctaaat ctaaactttg gcggtaacta tcagtgatgg tacagtccct tgagctgcca   1740
cagaggcaac cttgtcactt tggaagttgg atcaagcgct caccctcggg cctcacctca   1800
aagtcaccga gtcaggtttt gggaaacaat ctgatagatg atgccaaggc tcgcctgaga   1860
aagtctgatg tcgggaccag atattctcac ctgtcctcta ataaattctc tgtccttgta   1920
ccactgctgg ccagaggagg aaagttgtat ttgatgttca cggtccgctc agacaagctg   1980
aaaagggaac ctggagaagt ctgcttccct ggaggaaaga gggacccggt ggacacagat   2040
gacacagcca ctgctctccg tgaagcccag gaggaggtgg ggctgcatcc ccaccaagtg   2100
gaggtggtct ctcacctggt gccatacgta tttgataatg atgcactggt aaccccccgta   2160
gtgggttttc tagaccacaa cttccaggcc caacctaatg ctgatgaagt gaaggaagtc   2220
ttctttgtgc ctttggacta tttcctccat ccccaagtct actaccagaa gcaaatcaca   2280
cagtctggcc gtgatttcat catgcattgc ttcgagtaca aagaccctga gactggtgtg   2340
aactacctaa tccagggaat gacctcgaaa ctggctgtgt tggtggcctt aattattttg   2400
gaacaaagtc ctgccttcaa gattgatttt gatctccatg acctgatacc gtcttgtgaa   2460
aggaccttcc tttggagata ttctttaagc aagttgtgaa gaccctgaaa cccaaaagaa   2520
cgtacatgag gtttttgtgt gagcttatgc tcagaacaac agtgtttagc aagtggcatc   2580
tgacaggtgt gaatattttc ctacaatgtg gctgtgagat ccttgcctga cttcctgttg   2640
ctgctttaga acactaaaag tttttcaaaa ctggaaaaat gcactggcag gggagaataa   2700
ttttacccat ttaaaaaaat ggcacgattt ttagtcatat tagggaaatt tgtcacatag   2760
taggccctta ataaatattt gtcaaatata tggct                              2795
```

<210> SEQ ID NO 35
<211> LENGTH: 2998

<212> TYPE: DNA
<213> ORGANISM: Mus musculus

<400> SEQUENCE: 35

```
ctgtcagcca actgattgca gatgtggttg gcattggagg aaccagattc cagcagtcct     60
tgtctatcat caacaactgt gccaacagcg accggatcat caagcacacc agcttttcct    120
ctgatgtgaa agatttgact aagaggatcc gcacagtcct gatggccaca gcccagatga    180
aggagcacga gaacgacccg gagatgctgg tggacctcca gtacagcctg gctaagtcct    240
acgccagcac ccctgagctc aggaagacgt ggctagacag tatggcgagg attcacgtta    300
aaaatgggga cctctcagag gcggcaatgt gctatgtcca cgtgacagcc ttggtggcag    360
aatatctcac acggaaaggc atgttcagac aggggtgcac agccttcagg gttatcacac    420
caaacatcga tgaagaggct tccatgatgg aagacgtcgg catgcaggac gtccatttca    480
acgaggatgt gctgatggag ctgctggagc agtgtgcgga tggactttgg aaggcggagc    540
gctatgagct gatcgctgac atctataagc tcatcatccc catctacgaa aagcggaggg    600
atttcgagag actagcccat ctgtatgaca cgctacaccg cgcatacagc aaagtgacag    660
aggtcatgca ctcgggccgc aggctcctgg ggacctactt ccgggtggct ttctttggac    720
aggggttctt cgaagacgaa gatgggaagg aatacatcta caaagagccc aagctcacgc    780
ctctgtcaga gatttctcag agactcctta aactttactc ggataaattt ggttccgaaa    840
atgtcaaaat gatacaggat tctggcaagg tcaacccgaa ggatctggac tccaagtttg    900
cctacatcca ggtgacccac gtgaccccat tctttgacga aaaggagtta caagagagga    960
gaacagagtt tgaacgatgt cacaacatcc ggcgcttcat gtttgagatg cccttcaccc   1020
agaccgggaa gaggcagggt ggcgtggagg agcagtgtaa gcggcggacc atcctgacag   1080
caatacactg cttcccctac gtgaagaagc ggatccctgt catgtaccag caccacactg   1140
acctgaaccc cattgaggtg gccatcgatg aaatgagcaa gaaggtggcc gagctccgcc   1200
agctctgctc gtcggctgaa gtggatatga tcaaactgca gctcaaactg cagggcagtg   1260
tgagcgtcca ggtcaatgct ggtccgctag catatgcccg agccttcctc gatgacacca   1320
acacaaaaag ataccctgac aataaggtga aactgctgaa ggaagttttc aggcaatttg   1380
tggaagcttg tggtcaagcc ttggcagtga acgagcgtct cattaaagaa gaccaactgg   1440
agtaccagga agagatgaag gccaactaca gggagatggc caaggagctc tccgacatca   1500
tgcgtgagca gatttgcccc ctggaggaga agacaagcgt gctaccaaat tccctgcaca   1560
tcttcaacgc catcagcggg acaccaacaa gcacagtggt tcaagggttg accagctcgt   1620
cctcagttgt gtgattttac ctcatgaacc gtgtgtgggg acatgctttg tcatgtgcaa   1680
actcaggatg acttccagag ctaatcactg gtgtggccaa gcacaggaag aagccatggg   1740
gaatgggaga gagaaggagc ctggactgtg atatttaata gcagatttta taggagtcgg   1800
gggaaggtgc acatagtttt ttaaatctca ctggcaatat ttagttttcc tcatgtctta   1860
acaggtatat gtggatactc ttgagctgaa gttcagtttt attcttctta cagtatagta   1920
ttaaaataaa tggtctaaag gaaaagaggg aaagtgtgct gggacacctg tggcaggtgt   1980
cctgggatac ctgtagcagg tgtcctggga cacctgtagc aggtgtgctg ggacacctgt   2040
agcaggtgct gggacacctg tagcaggtgt tgctgggact gggacacctg tagcaggtgt   2100
tgctgggact gggacacctg taacaggtgt tgctgggact gggacacctg tagcaggtgt   2160
tgctgggact gggacacctg tagaaggtgt cctgggactg ggacacctgt agcagacaaa   2220
gcagcactga acctggggtt ggggactaag ctggaaaaat cttgaaaata tttttctccc   2280
```

```
tggggcacat tcaggttgag tacaagaact atttttgtgt ctaattttga tgacggaaag   2340

gaattgccta ttgtaatttt gtactagtga atgaggagac ttagagcctt tatattcatg   2400

ccttgtgttg gcaacatgag cacttcagaa gctgagtgtg agcctaagcc tagtcagcat   2460

tatagaacca aaggcctgta ctagcaaaca cacccatgct aaaacctaaa accccatgta   2520

catactgact gtcaatacag cctccttgct atgtccacac actcaccaca tttctacact   2580

tttaatacgt cagtgtccat gttaagttta ttattcgtgg cccatttgtg ctgttctcag   2640

tatatgcaaa cacattggac ttcactgttt attcttgtac ataagaagtg caatatggag   2700

atgtatacag tctttgctat attaggttta taaactgttt taaaaaaatt catccttttg   2760

ccaaaatgat gaactaagtg attggtaaac cctaagccct gtatgagtgg agggatagtt   2820

taaagttttc accatgttat attttctttt gagactttaa tttagtaatt ttatatttgg   2880

gaaaaaaaat aaaggttttt aatttaactg gaatcactgc cctgctgtaa ttaaatatcc   2940

tgtaccccaa ctgtattaaa aataacattg ctgattttct ggtaataaaa aaaaaaaa     2998
```

```
<210> SEQ ID NO 36
<211> LENGTH: 2103
<212> TYPE: DNA
<213> ORGANISM: Mus musculus

<400> SEQUENCE: 36

aagacttcgg cggcggcctt tggagatgca gtcggctcgg atgaccccga gtgtggggcg     60

acagctgctg cggctggggg cccgaagctc gcgatctact actgtgcttc agggacaacc    120

ccggcctatc tctgcccagc gactttatgc cagggaggcc actcaggcag ttctggacaa    180

gccagaaacc ctctcctctg atgcttccac cagagaaaaa ccagccaggg cagaatcgaa    240

gtcctttgct gtggggatgt tcaaaggcca gcttaccatt gatcaggtgt tcccataccc    300

atctgtgctc agtgaagaac aggcacaatt tctcaaagag ctggtgggac cagtggcccg    360

gttctttgag gaagtgaatg accctgccaa gaacgacgcc ttggagaagg tggaggacga    420

cactttgcag ggactcaagg aactgggggc atttggcctg caagtaccca gcgagctggg    480

tggtttgggc ctctctaata cccagtatgc tcgcttggca gagattgtgg gcatgcatga    540

ccttggtgtt agcgttaccc tgggagctca tcagagcatc ggtttcaaag gcatcttgct    600

ctatggcaca aaggcccaga gagaaaaata ccttcccaga gtggcatctg ggcaggcttt    660

ggctgctttc tgcctaacag agccctcgag tggatccgat gtagcctcca tccgaagctc    720

agccataccc agcccctgtg gaaaatatta cactctcaat gggagcaaga tctggatcag    780

taatgggggc ctggctgaca ttttcactgt ctttgccaag acgccaatta aagatgcagc    840

cacgggggcc gtgaaagaga agatcacagc ttttgtagtg gaaaggagct tcggaggggt    900

tacccatggg ctccctgaaa agaagatggg catcaaagca tctaacacgt cagaggtgta    960

ctttgatgga gtgaaggtgc catcagagaa tgtgctagga gaggtgggag atggcttcaa   1020

ggttgctgtc aacatcctca acaacggaag attcgggatg gctgcaaccc tcgcaggcac   1080

catgaaatcc ctcattgcca aggcggttga tcatgctact aatcgtaccc agtttgggga   1140

caaaattcac aactttgggg tgatccagga aaagctggct cggatggcta ttctgcagta   1200

tgtgactgag tccatggctt acatgctgag tgccaacatg gaccagggat tcaaagactt   1260

ccagatagaa gccgccatca gcaaaatctt ttgctcggag gcggcctgga aagtggcaga   1320

tgagtgcatc caaataatgg ggggcatggg cttcatgaag gaaccagggg tggagcgtgt   1380

gctccgagat attcgaatct tccggatctt tgaaggggca aatgacattc ttcgactgtt   1440
```

```
tgtggctctg caaggctgta tggacaaagg aaaggaactc actgggctgg gcaatgccct   1500

gaagaatcct tttggaaacg ttggcctcct gatgggagaa gcaggcaaac agctgagacg   1560

gaggacagga atcggcagtg gtttgagtct gtcagggatt gtccacccag agttaagtcg   1620

cagtggtgaa ctggcagtgc aggctctgga tcaatttgcc accgtggtgg aggccaagct   1680

ggtgaaacac aagaaaggga ttgtcaacga gcagttcctg ctgcagcgac tggcggacgg   1740

cgccattgac ctctatgcca tggtggtggt tctgtccaga gcctcaaggt ccctgagtga   1800

gggctacccg acggcacagc atgagaaaat gctctgtgat agctggtgca ttgaggctgc   1860

aactcggatc cgagaaaaca tggccagtct gcagtccagc cctcagcatc aggagctctt   1920

ccggaacttc agaagcatct ccaaggccat ggtggagaat ggtggcctgg tcaccggtaa   1980

ccccctggga atctgagact cccaatcagg ccctggcaag gtcatgtgcc ttctctgatg   2040

ccaaaaccct ttatgggggt gatggagtac ttattgcctt aacaataaat tttctaccaa   2100

gtc                                                                 2103
```

```
<210> SEQ ID NO 37
<211> LENGTH: 3187
<212> TYPE: DNA
<213> ORGANISM: Mus musculus

<400> SEQUENCE: 37

cggagctcag ggctgaagat ggttcctctc ctgcccttat atgctctgct gctgctgttc     60

ctgtgtgata ttaaccctgc aaatgccaac agttactatg acaaggtcct ggctcacagc    120

cgcatcaggg gtcgggatca gggcccaaac gtctgtgccc tccagcaaat tctgggcacc    180

aaaaagaaat acttcagctc ctgtaagaac tggtatcaag gtgctatctg cgggaagaaa    240

accactgtgc tatatgaatg ctgccctggc tatatgagaa tggaagggat gaaaggctgc    300

cccgcagtga tgcctattga ccatgtttat ggcacgctgg gcattgtggg agccactacc    360

actcagcact actccgatgt ctcgaagctg agagaagaga ttgaaggaaa agggtcatac    420

acgtacttcg cgccgagtaa cgaggcttgg gagaacctgg attctgacat tcgcagagga    480

ctggagaaca atgtcaatgt tgagctactg aatgccttac acagccacat ggttaataag    540

agaatgttaa ccaaggacct gaaacacggc atggttattc cttcaatgta caacaatctg    600

gggcttttta ttaaccatta tcccaatggg gttgtcactg tgaactgtgc tcgagtcatc    660

catgggaacc agattgccac aaatggtgtc gtccatgtca ttgaccgtgt cctgacacaa    720

attggtacct ccatccaaga cttccttgaa gcagaagacg acctttcatc atttagagca    780

gccgccatca cctctgacct cttggagtcc cttggaagag atggtcactt cacgctcttt    840

gctcccacca atgaagcttt cgagaaactg ccacgaggtg tcctagaaag gatcatggga    900

gacaaagtgg cttctgaagc tctcatgaag taccacatcc taaataccct ccagtgctct    960

gaggccatca ctggaggagc cgtgtttgag accatggaag gaaacactat tgagataggg   1020

tgcgaagggg acagtatctc cattaacgga atcaagatgg tgaacaagaa agacattgtg   1080

actaagaatg gtgtcatcca cctgattgat gaagtcctca ttcctgattc tgccaaacaa   1140

gttattgagc tggctggaaa acagcaaacc actttcaccg acctggtagc ccaattaggc   1200

ttggcatcct ctctgaagcc agatggagag tacaccttat tagcacctgt gaacaatgcg   1260

ttctctgatg acactctgag catggaccaa cgccttctta agctaattct gcaaaatcac   1320

atattgaaag taaaagttgg ccttagcgac ctctacaatg gacagatact ggaaaccatt   1380

ggaggcaaac aactccgagt ctttgtgtat cggacggcta tctgcataga aaactcatgc   1440
```

```
atggtgagag gaagcaagca gggaaggaat ggtgccattc acatattccg agaaatcatc   1500

caaccagcag agaaatccct gcacgacaag ctgcggcaag acaagcgctt tagcatcttc   1560

ctcagcctcc ttgaagctgc agatttgaaa gatctcctga cacagcccgg agattggacc   1620

ttgtttgcac caaccaatga tgccttcaag ggaatgacta gcgaagaaag ggagcttctg   1680

attggggata aaaatgctct ccaaaacatc attctttatc acctgacccc aggggtttat   1740

attggaaagg gattcgaacc cggagtcact aatatcctga agaccacaca gggaagcaaa   1800

atctatctga aaggagtaaa cgaaacgctt ctagtgaatg agttgaagtc caaagaatct   1860

gacatcatga cgacaaatgg tgtcatccac gtcgtggaca aactcctcta tccagcagat   1920

attccagttg gaaatgatca gctcttggaa ttactgaaca aactgataaa atacatccaa   1980

atcaagtttg ttcgtggcag caccttcaaa gaaatcccca tgactgtcta tagacctgca   2040

atgacgaaga tccaaattga aggtgatccc gacttcaggc tgattaaaga aggcgaaacg   2100

gtgacagaag tgatccacgg agagccagtc attaaaaagt acaccaaaat catagatgga   2160

gttcctgttg aaataactga aaaacagact cgggaagaac gaatcattac aggtcctgag   2220

ataaaatata ccaggatttc cacaggaggt ggagaaacag gagagacctt gcagaaattc   2280

ttgcaaaaag aggtctccaa ggtcacaaag ttcattgaag gtggcgatgg tcacttattt   2340

gaagatgagg agattaaaag actgcttcag ggagacacac ctgcaaagaa gataccagcc   2400

aacaaaaggg ttcaagggcc tagaagacga tcaagagaag gccgttctca gtgaaaaccc   2460

agaggccaga ccacagagtt tatataatcc taaatcaacg atctgatttt aagggaaatt   2520

gtaagagcca ccacactgac ttcagaatct gaaatgacaa ccaacagaag ccaatcttca   2580

agcaagtcca aacacagagt tcatgtcttt gtttctgcat gagaaatata agaaaatgat   2640

agctagtctc ctgtggggta ggaactgagg aaatatagga ccatgcaggg attttatctc   2700

aatgagaaaa cttctgatta aagtagaatc caccaaagaa catcattgtg actgggtcca   2760

tacagctaag tctttgcaca gtaaaaacct tccgcctcag gaagaggctg gaaaaaccca   2820

aagcacacag ttacctttcc aggggaggct aaggtatcaa aaggggtgtt cagttataca   2880

acatgcaaac aaacctacca aattacgaac agtggtgtta catatttctc atgcaatgtg   2940

ggtttcctgc taaattttgt tatttttaca cttgatttat atcctcgaga tgattgtcat   3000

aagcttcttg caatacaaat gttttctctc aaacatttca ataaaaccat tcttcaggta   3060

taaagagaat tactgcagag ttggtaattc agaaaactca aggtttaagt taaaagtgag   3120

tttagacttt ggaataggac ttcatacctt tttttattgt taacaagtac tcaataaagt   3180

aaactga                                                              3187
```

<210> SEQ ID NO 38
<211> LENGTH: 1871
<212> TYPE: DNA
<213> ORGANISM: Mus musculus

<400> SEQUENCE: 38

```
ggtcctgcga gtttagccat ggcgctcagc tttctctctc caagcctttc ccgcctcggc     60

ctgtgggctt ctgtagtgat cctgatggta accgtcctga agctcctcag cctgctgttt    120

cggaggcaga agctggccag ggctttggac agcttcccag ggccccccaa gcactggctt    180

tttggtcatg cccttgagat ccagaagaca ggaggcctgg acaaggtggt aacttggacc    240

gaacagttcc cctatgccca cccactctgg cttggacaat ttattgtttt cctgaacatc    300

tatgagcctg actatgctaa agctgtatac agccgagggg acccgaaggc tgcatatgtg    360
```

```
tatgacttct tcctccagtg gatcggaaaa ggcctactgg ttctggaagg gccaaaatgg    420

ttccagcacc gcaagctgct cacacctggc ttccattatg atgtgctgaa gccctatgtg    480

gccatatttg ctgagtccac acgggtgatg ctggacaagt gggagaaaaa ggctagtgag    540

aataagagct ttgacatctt ctgtgacgtg ggccacatgg cactggacac cctcatgaag    600

tgcacctttg gcaaaggaga cagcggccta agccacagtg acaacagcta ctacctggca    660

gttagtgacc tcacactgct gatgcagcag cgcatcgact ccttccagta ccataatgac    720

ttcatttact ggctcacacc acatggccgc cgtttcttgc gggcctgcca gatagcccat    780

gaccatacag atcatgtcat caggcagcgg aaggcagctc tgcaggatga gaaggagcag    840

aaaaagcttc aggagcggag acacctggac ttcctcgaca ttctcctggg tgcccgggat    900

gaaagtggga tcaagttgtc agatgcagac ctccgggctg aagtggacac attcatgttc    960

gaaggccacg acaccaccac tagtggtatc tcttggtttc tctactgcat ggccctttat   1020

cctatgcacc agcagcgatg tagggaggag gtccgtgaga tcctagggga ccgggactcc   1080

ttccagtggg atgatctggc ccagatgacc tacctgacca tgtgcatgaa ggagtgcttc   1140

cgcctctacc cacctgtacc ccaagtgtac cgccagctca gcaagccagt aacctttgtg   1200

gatggccgct ctctacctgc aggcagcctg atctctctgc acatctatgc cctccatcgg   1260

aacagtgctg tgtggcctga cccagaggtc tttgacccac tgcgcttttc tcctgagaat   1320

atgacaggac ggcatccctt tgccttcatg cctttttctg cagggcccag gaattgcatt   1380

gggcaacagt ttgccatgaa cgagatgaag gtggtcacag ccctctgttt gctgcgcttt   1440

gaattctctc cagatccctc aaagatcccc attaaggtcc cccagctgat cttgcgctcc   1500

aaaaatggca tccacctcta cctgaagcca ctgggccctg ggtctggaaa gtaggtctta   1560

ggagagcaag gatatggagt cattgtggat ccctgcctgt ggggggtttg tgagataaaa   1620

gcatgcacat tgagagtatc ctggaagaca ttctcttgta aacatgtgtg tggaatgatt   1680

caatgcctgg gctttcaaac tcattccttc actccacaaa tatttgctga atgtttccct   1740

gtcttgagaa acttcattta tttctcataa ctgcatttat ttagccatct cagtgtgcat   1800

tttggatata atagacataa ggaaaattgc ttaaactaaa tctgtacaaa ataaataata   1860

ctttaaaaag c                                                        1871
```

<210> SEQ ID NO 39
<211> LENGTH: 11009
<212> TYPE: DNA
<213> ORGANISM: Mus musculus

<400> SEQUENCE: 39

```
gacctctact gcaagctggt tgggggtccg gtggctggcg gagatcccaa tcagacaatc     60

cagggccagt actgtgacat ctgtacagct gccaacagca acaaggcaca ccctgtgagc    120

aacgccatcg atggcacgga gcgctggtgg cagagcccac ccctgtcccg tggcctggag    180

tacaatgagg tcaacgtcac actggacctg ggccaggtgt tccatgtggc ctatgtgctc    240

atcaagtttg ccaactcacc tcggcctgac ctctgggtgc tggagcggtc cacagacttc    300

ggtcacactt atcagccgtg gcagttcttt gcctcctcca agagggattg tttggagcgg    360

tttggacctc ggactctaga gcgcatcacg caggacgacg acgtcatctg caccacagaa    420

tactcgcgaa tagtgccttt ggagaatggc gagattgtgg tgtccttggt aaatgggcgc    480

cctggggcct tgaacttctc ctactcaccg ttacttcgag acttcaccaa agccaccaac    540

atccgcttgc ggtttctgcg aaccaacacg ctactgggcc acctcatggg caaggcgctg    600
```

-continued

```
cgggacccca cagtcacccg caggtattat tacagcatca aagacatcag cattggtggg    660
cgctgtgtct gtcatggcca cgcagatgtc tgtgacgcca aggacccatt ggatcctttc    720
aggctgcagt gtgcctgcca gcacaataca tgtggaggct cttgtgaccg atgctgtcca    780
ggcttcaacc agcagccgtg gaagcccgcc accacggaca gcgccaatga gtgccagtcc    840
tgcaattgcc acggccatgc ctacgactgt tactacgacc ctgaggtgga tcggcgcaat    900
gccagccaga accaggacaa cgtgtaccag ggtggaggtg tctgcctgga ttgccagcat    960
cacactacgg gtatcaactg tgagcgttgt ctgcctggct tcttccgtgc cctgaccag    1020
cctctcgact cacctcatgt ctgtcggccc tgcgactgtg agtcagactt cacggatggg   1080
acctgtgaag acttgacggg ccgctgttac tgcaggccga acttcacagg agagctatgt   1140
gctgcctgcg ctgagggcta cacggacttc ccacactgct accctctgcc ttcatttcct   1200
cacaatgaca cgagagaaca ggtgcttccc gctggacaaa tcgtgaactg tgattgcaat   1260
gctgcaggga cccagggcaa tgcctgccgg aaggacccaa ggttgggacg gtgtgtctgc   1320
aaacccaact tccggggtgc ccactgtgag ctctgtgctc ctggattcca cgggcctagc   1380
tgccacccat gccagtgttc cagccctggg gtagccaaca gcctctgtga cccagagtct   1440
ggccagtgca tgtgccgcac cggctttgag ggggacaggt gtgaccactg tgcccttggc   1500
tatttccact tccctctctg tcagctgtgt ggctgcagcc cagcagggac cctgcctgaa   1560
ggctgtgacg aggctggccg ctgccagtgc cgacctggct ttgacggtcc tcactgtgac   1620
cgatgccttc caggatacca tgggtatccc gactgtcacg cttgtgcctg tgaccctcgg   1680
ggggccctgg atcaacagtg tggagtgggc ggtttgtgcc actgccgtcc tggcaacaca   1740
ggtgccactt gtcaggaatg tagccccggc ttctacggct tccccagctg catcccctgc   1800
cactgctctg ccgatggctc cttgcataca acctgtgacc cgacaaccgg ccagtgtagg   1860
tgtcgacccc gagtgacagg actacattgt gatatgtgtg taccaggcgc ctataacttc   1920
ccctactgtg aagctggctc ttgtcatcct gctggtctgg ccccagccaa tcctgccctt   1980
cctgagacac aggctccctg tatgtgccgg gctcacgtgg aagggccaag ctgtgatcgc   2040
tgtaaacctg ggtactgggg gctgagcgcc agcaaccctg aaggctgcac acgctgcagc   2100
tgtgacccac gaggcaccct gggtggagtt actgagtgcc agggcaatgg gcagtgcttc   2160
tgcaaggctc acgtgtgtgg caagacctgt gcagcctgca aggatggctt ctttggcctg   2220
gattatgctg actactttgg ctgccgtagc tgtaggtgtg atgttggtgg tgccctgggt   2280
cagggctgtg aaccaaagac aggtgcctgc aggtgccgcc ctaacaccca aggacccacc   2340
tgtagcgagc cagcgaagga ccactacttg ccagacctgc accacatgcg gctggaacta   2400
gaggaggcgg ccactcccga gggccacgct gtacgctttg gcttcaaccc cctggagttt   2460
gagaacttta gctggagagg ctacgcacac atgatggcta tccagcccag gattgtggcc   2520
aggctgaacg tgacctcccc tgacctcttt cgactggttt tccgatatgt caaccgtgga   2580
tcaaccagcg tgaatgggca gatctctgtt cgtgaagagg gcaagctttc cagctgtacc   2640
aactgcacag agcagagcca gccagtggct ttcccaccca gcactgagcc tgcctttgtc   2700
actgtgcccc agaggggctt tggggaaccc tttgtgctga accccggcat ctgggccttg   2760
ctggtcgagg ctgaaggtgt actcttggac tacgtggtcc tactgcccag cacctactat   2820
gaggcagctc tcctacagca tcgagtaacg gaggcctgta cctaccgtcc ctcagccctg   2880
cactccacag agaactgtct tgtctatgct cacctacccc tggatggctt cccttcagca   2940
gctggaactg aggccctgtg tcgccatgac aacagcctgc cccggccctg ccccacagag   3000
```

```
cagctcagcc cctcacaccc accgctggcg acctgcttcg gcagtgatgt ggacatccag   3060
ctcgagatgg ccgtgcctca gcctggccaa tatgttctcg tggtggaata tgtcggtgag   3120
gattcacacc aagagatggg agtggctgtg cacacccctc agagagcccc ccagcaaggg   3180
gtgctcaacc tccacccctg cccatacagc tccctgtgcc ggagtccggc tcgggacacc   3240
cagcatcatc tagccatctt ccacctggac tctgaggcta gcatccggct cacagctgag   3300
caagctcact tcttcctgca cagcgtcacc ctggtacctg tggaggagtt cagtactgag   3360
tttgtggagc cccgggtctt ctgtgtgagc agtcatggaa ctttcaaccc cagcagtgct   3420
gcctgtctag cctcccgatt cccgaagcca ccgcagccca tcatccttaa ggactgccag   3480
gtcttgccgc tgcctcccga cctgcctctg actcagtctc aggagctctc accaggtgca   3540
ccccccgagg gaccacagcc tcggccgcca actgcggtgg atcctaatgc agaacccacc   3600
ttgctgcgcc acccccaggg cacggtggtc ttcaccaccc aggtgcccac cctgggccgc   3660
tatgccttcc tgctgcacgg ctaccagccg gtccacccct ccttccctgt ggaggtactc   3720
attaatggtg gccgcatctg gcagggccac gccaacgcca gcttttgtcc tcatggttat   3780
ggctgccgta ccctggtgtt gtgtgagggt cagacgatgc tggatgttac agacaacgag   3840
ctcaccgtga ctgtgcgtgt gccagaaggc cggtggctct ggctggacta cgtactcatt   3900
gtccctgagg atgcttacag ctccagttac ctccaagagg agcctttgga caaatcctat   3960
gacttcatca gccactgtgc cacccagggc taccacatta gccccagcag ctcatctcca   4020
ttctgccgga atgccgccac ctccttgtct ctcttctaca acaacggggc cctcccttgt   4080
ggctgccacg aggtgggtgc cgtaagcccc acgtgcgaac ccttcggggg ccagtgtccc   4140
tgccggggcc acgttattgg ccgtgactgt tcccgctgtg ccaccggcta ctggggtttc   4200
cccaactgca ggccctgtga ctgtggagcc cgcctgtgtg acgagctcac gggccagtgt   4260
atctgtccac cacgcactgt tccccctgac tgcttggtct gccagccaca gagctttggt   4320
tgccacccct tggtgggctg tgaggagtgt aactgctcag ggcccggcgt ccaggagctg   4380
acggacccta cctgtgacat ggacagcggc cagtgcagat gcagacccaa tgtagctgga   4440
cgtcgctgtg atacctgtgc cccgggcttc tatggctatc ctagctgtcg cccctgtgac   4500
tgccatgagg caggcaccat ggctagcgtg tgtgaccccc tcacaggcca atgccattgc   4560
aaggagaacg tgcagggctc aagatgtgac cagtgtcgcg tggggacctt ctccttggat   4620
gctgctaacc ccaagggctg tacccgctgc ttctgtttcg ggccacaga gcgctgtggg    4680
aactctaacc tcgcccgcca tgagttcgtg gacatggagg gctgggtgct gttgagcagt   4740
gaccggcagg tggtacccca cgagcatcgg cctgagatag agctgctgca cgcagatctg   4800
cgctctgtgg ctgacacttt ctcagagctg tactggcagg ctccgccctc ctatctggga   4860
gacagggtgt catcctacgg tggaaccctc cactatgagc tgcactcaga gacccagcga   4920
ggtgatatct tcattcccta cgagagccgg ccggacgtcg tgctgcaggg caaccaaatg   4980
agcatcgcct tcctggaact ggcgtaccct ccgcctggcc aggttcaccg aggacagcta   5040
cagctggtag aggggaactt ccggcacttg gagactcaca accccgtgtc ccgagaagaa   5100
ctcatgatgg tgctggccgg cctggagcag ctgcagatcc gtgctctctt ctcgcagacc   5160
tcttccagtg tctccttgcg tagagtggta ctggaggtgg ctagcgaggc tggtaggggg   5220
cctccagcca gcaatgtgga actgtgtatg tgccctgcca actaccgtgg ggactcgtgc   5280
caggaatgtg cccctggcta ttaccgggac accaagggtc tcttcctagg ccgatgtgtc   5340
ccctgtcagt gccatggcca ttcagatcgc tgccttcctg gctctggcat ttgtgtgggc   5400
```

-continued

```
tgccagcaca acacagaagg ggaccaatgt gagcgctgta ggcctggctt tgtcagcagt   5460
gatcccagta accctgcatc cccatgtgtg agctgccctt gccccttggc agtgccctcc   5520
aataattttg cagacggttg cgtcttaaga aatggccgaa cccagtgcct ctgcaggcca   5580
ggctatgctg gtgcctcctg cgagcggtgt gcacctggct tttttgggaa ccccctggtg   5640
ctaggcagct cctgtcagcc ctgcgactgc agcggtaatg gagaccccaa catgatcttc   5700
agtgactgcg acccccctgac gggtgcctgt cgaggctgcc tccgtcacac cactgggccc   5760
cactgtgaac gctgtgcccc aggcttctat ggcaatgctt tgttgccagg caactgcacc   5820
cggtgtgact gttccccatg tgggacagaa acctgtgatc cccagagtgg acgctgcctg   5880
tgcaaagcag gcgtgactgg acaacgttgt gaccgctgtt tggaaggata cttcggtttt   5940
gagcaatgcc agggctgccg cccttgtgcc tgtggaccag ctgccaaggg ctccgagtgc   6000
caccctcaga gcggtcagtg tcactgccag ccagggacca caggacccca gtgcctcgag   6060
tgcgcccctg gctactgggg cctcccagag aagggctgca ggcgctgcca gtgtccccga   6120
ggccactgtg acccacacac gggccactgc acctgtcccc cggggctcag cggggaacgc   6180
tgtgacacct gcagccagca gcaccaggtg cctgtaccgg gcaagcctgg gggccatggc   6240
atacactgtg aagtgtgtga ccactgtgtg gttctccttc tggatgacct cgagcgggct   6300
ggtgccctcc tccccgctat ccgtgagcag ctgcagggta tcaatgccag ctccgcggcc   6360
tgggccaggc tgcacaggct gaatgcctcc attgctgacc tgcagagtaa actccggagg   6420
ccaccgggac cccgctacca ggcagcacag cagctacaga ctctagagca gcagagtata   6480
agccttcaac aggacacgga gaggctgggc agtcaggcca caggggtcca aggtcaggca   6540
ggccagctac tggacaccac agagtccaca ctgggccggg cacagaagtt gttggagtct   6600
gtgcgagctg tgggccgtgc cctgaatgag ctggcatctc gcatgggcca aggatctcca   6660
ggcgatgcct tggtaccgtc tggcgagcag ctgcgctggg ctctggctga agtggagcgg   6720
ctgctctggg atatgcggac gcgtgacctg gggcccagg gggcagtggc agaggccgaa   6780
ctggccgaag cccagaggct gatggctcgt gtccaggagc agctgaccag cttctgggag   6840
gagaaccagt cattggccac acacattcgg gaccagctgg ctcagtatga gtctggcctc   6900
atggatcttc gtgaggccct gaaccaggcc gttaatacca cccgggaggc tgaggaactc   6960
aacagccgca accaggaacg ggtgaaggaa gccctgcaat ggaaacagga actgtcccag   7020
gacaatgcca ccctgaaggc cactcttcaa gctgccagtc tcatcttggg ccatgtttct   7080
gagcttctgc agggcataga ccaggctaag gaggacctag agcacctggc ggccagcctg   7140
gatggagcct ggacaccctt actgaagagg atgcaggcct tttcccctgc cagcagcaag   7200
gtggacttgg tagaggctgc tgaggcccac gctcagaagc tgaaccagct ggcaatcaac   7260
ctgtctggca tcatccttgg catcaatcag gaccgcttca tccagagggc tgtggaagcc   7320
tccaatgcct acagcagcat ccttcaggcc gttcaggctg ccgaggatgc ggcaggccag   7380
gcactgaggc aggccagccg cacatgggag atggtggtgc agcggggcct agcagctgga   7440
gcccggcagc tgttagccaa cagcagtgcc ctggaggaga ccatccttgg acaccagggg   7500
aggctgggcc ttgctcaggg ccgtctgcag gctgcgggga tccagcttca taatgtctgg   7560
gccaggaaga accagctagc agcccagatc caggaggcac aagccatgct ggccatggac   7620
acgagcgaga ccagtgagaa gattgctcac gccaaggctg tggctgccga agccctcagt   7680
acggccaccc acgtgcagtc tcagcttcag ggtatgcaga agaatgtgga gaggtggcag   7740
agccagctgg gaggcctgca aggccaggac ctgagccagg tggaacggga tgcaagcagt   7800
```

```
tcagtgtcca ccctggagaa gacattgcca cagctgctgg ccaaactgag ccgtctagag   7860

aaccgtggag ttcacaatgc cagcctggct ttgtctgcca acattggtcg tgtgcgcaag   7920

ctcattgccc aagcccggag tgccgccagc aaggtcaagg tgtccatgaa gttcaatggg   7980

cgttcagggg tacgactgcg tcccccacga gaccttgccg accttgctgc gtacactgcc   8040

ctcaagttcc acatccagag cccagtgcca gcgcccgaac ctggcaagaa cacgggggac   8100

cactttgttc tgtacatggg cagccgccag gccactgggg actacatggg agtgtctctg   8160

cgtaatcaga aggtgcactg ggtgtacagg ctaggaaagg ctggccccac aactctcagc   8220

atcgacgaga acatcgggga gcagtttgca gccgtcagca tcgacaggac cctccagttt   8280

ggccacatgt ctgtcaccgt ggagaaacag atggttcatg agatcaaggg agacacggtg   8340

gcccctggga gcgagggact actcaacctg catcctgacg attttgtctt ctacgtggga   8400

ggatacccca gcaacttcac gccccctgaa cccctccgat tccctggcta cctgggctgc   8460

attgagatgg aaacactgaa tgaggaggtg gtcagcctct acaattttga gcagaccttc   8520

atgctggaca cggcagtaga taaaccttgt gctcgctcca aggccaccgg tgacccatgg   8580

ctcacagatg gctcctacct ggatggcagt ggctttgccc gcatcagctt tgagaagcag   8640

ttcagcaaca caaaacgctt tgaccaggag ctgcggcttg tgtcctacaa tgggatcatc   8700

tttttcctca agcaagagag ccagttcttg tgcctggcag tgcaggaagg caccctggtg   8760

ctcttctatg acttcggctc tggcctgaag aaggccgacc cactgcagcc ccccacaagcc   8820

ttgacggcag ccagcaaggc gatccaagtg tttctattgg ctggcaatcg caaacgtgtg   8880

ttggtgcgtg tggagcgggc cactgtgttc agcgtagacc aggataacat gctggagatg   8940

gctgatgcct actacttggg aggdgtgcca cctgaacagc tgcccttgag cctacggcag   9000

ctcttcccct ccggaggctc tgtccgtggy tgcatcaagg gtattaaggc tctgggcaag   9060

tacgtggacc tcaaacggtt gaacaccacg ggcatcagtt tcggctgcac cgctgacctg   9120

ctagtgggac gcaccatgac ttttcacggc cacggcttcc tgcccctggc acttcctgat   9180

gtggcaccca tcaccgaagt ggtctattct ggctttggct ttcgtggcac ccaggacaac   9240

aacctgctgt attaccgtac ctccccggat gggccgtacc aggtatccct gagggagggc   9300

cacgtgacac tccgttttat gaaccaagag gtggaaactc aaagggtctt tgctgatggt   9360

gctcctcact atgttgcctt ctatagcaat gtcacagggg tatggctgta tgtggatgac   9420

cagctacaac tagtaaagtc tcatgagaga acaactccca tgctccaact acagcccgag   9480

gaaccctcac ggcttctcct gggaggcctg cctgtgtctg gtaccttcca caacttcagt   9540

ggctgcatca gcaatgtttt tgtacagcga cttcggggac cacagcgtgt gtttgaccta   9600

caccagaaca tggggagtgt caatgtaagc gtaggctgta caccagccca actcatcgag   9660

acctcaaggg ccacggctca gaaggtttcc cgccgtagtc gacaacccag ccaggacctt   9720

gcctgcacga caccctggct ccctgggact attcaggatg cataccagtt tgggggaccc   9780

ctgcccagtt acctacagtt tgtgggtatc tctccgtccc acaggaatag gctccacctc   9840

tccatgcttg tccgtccaca tgcggcttcc cagggcctcc tgctctctac agcccccatg   9900

tcgggccgca gcccttcgtt ggtactcttt ctaaaccatg gacactttgt cgcacagact   9960

gagggccctg ggccccggct ccaggtccag agtcgccagc actcacgggc tggccagtgg  10020

cacagggtgt ccgtccgctg ggaatgcag cagatccagc ttgtggtgga cggcagccag   10080

acctggagcc agaaggctct ccaccatcgg gtccccaggg cagagcgacc acagccctac  10140

accctctctg taggaggtct tcctgccagc agttacagtt ccaagctccc tgtgtctgtg  10200
```

```
gggttcagcg gctgtctgaa gaaattacag ctggataagc agccactgag gaccccaacg  10260

caaatggtgg gggtcacacc ctgtgtctca ggcccccctgg aagatggcct gttcttccca  10320

ggcagtgagg gagttgtcac attagagctc cccaaggcca agatgcccta tgtgagcctg  10380

gagctagaga tgcggccctt ggcagctgct ggcctcatct tccacctggg ccaggccctg  10440

gccactccct acatgcagct gaaggtgctg acagaacagg tcctgctgca ggcaaatgat  10500

ggggcagggg agttttccac gtgggtgacc taccccaagc tttgtgatgg acggtggcac  10560

cgagtggcag tgatcatggg cagggacaca ctccggctgg aggtagacac acagagcaac  10620

cacaccacag gccgtttgcc agagagcttg gctggttctc cagcacttct gcacctcggg  10680

agcctgccca agtcttcaac tgctcggcca gagctccctg cctaccgagg atgcttgagg  10740

aagctgctga tcaatggggc ccctgtcaac gtgactgctt ctgtacaaat ccagggggca  10800

gtggggatgc gcggatgccc ctcaggaacc ctagcacttt ccaagcaggg aaaggcactg  10860

acccagaggc acgccaagcc cagtgtctcc ccgctacttt ggcattgagg gttcccagac  10920

cttggggttt gcctacactt tctatgaata acaagtcatt tctggtttac actgtctttt  10980

agaggaaaag gactctgtag aacagatat                                   11009
```

<210> SEQ ID NO 40
<211> LENGTH: 2468
<212> TYPE: DNA
<213> ORGANISM: Mus musculus

<400> SEQUENCE: 40

```
caggctgagc tcatggcttc cccccctgagg ttcgacgggc gtgtggtctt ggtcaccggc     60

cccgggggag gattgggccg agcttacgcc ctggcgtttg cagaaagagg agcattagtc    120

attgtgaacg acttaggagg ggacttcaag ggaattggta aaggctcctc tgctgcagac    180

aaggttgtgg cagagataag aaggaaaggc ggaaaagcag tggccaatta cgattcagtt    240

gaagcaggcg agaagcttgt gaagacggca ctggacacat ttggcagaat agacgttgtg    300

gtcaacaatg ctggaatcct gagggaccgt tccttctcca ggataagtga tgaagactgg    360

gatataattc atagagttca tttgcggggc tccttccaag tgacccgggc agcatgggac    420

catatgaaga aacagaatta tggaagaatc cttatgactt cctcagcttc tggaatatat    480

ggcaactttg gccaggcgaa ttatagtgct gcaaagctgg gcattctggg tctctgcaat    540

actctcgcca ttgaaggcag gaagaacaac attcattgca acaccattgc cccccaacgct    600

gggtcacgga tgacggagac tgtgttgccg gaagatcttg ttgaagccct gaagccagag    660

tatgtggccc ctctggtgct ttggctttgc catgagagct gtgaggaaaa tggtggccta    720

tttgaggttg gagcaggatg gattggaaaa ttgcgctggg agaggaccct gggcgccatc    780

gtcagaaagc ggaatcagcc catgactccc gaggcagtga gggacaactg ggagaagatc    840

tgtgacttca gcaatgccag caagccgcag accattcaag aatcaacagg tggtatagtc    900

gaagttttac ataaggtaga ttcagaagga atctcaccaa accgtaccag tcacgcggca    960

cctgcagcca cgtcaggatt cgttggtgct gttggccata aacttccttc attttcttct   1020

tcgtatacgg agctgcagag tattatgtat gccctcggag tgggagcgtc agtcaaaaat   1080

ccaaaggatt tgaagtttgt ttatgaaggc agtgctgact tctcctgttt gcccaccttc   1140

ggagtcattg tcgctcagaa gtccatgatg aatggagggc tggcagaggt tcctgggctg   1200

tcattcaact ttgcaaaggc tcttcacggg gagcagtact tggagctgta taagccactt   1260

cttcgatcag gagaattaaa atgtgaagca gttattgctg acatcctgga taaaggctct   1320
```

```
ggcgtagtga ttgttatgga cgtctattct tattctggga aggaacttat atgctataat   1380

cagttctctg tctttgttgt tggctctggg ggctttggtg gaaaacggac atcagaaaaa   1440

ctcaaagcag ctgtagctgt accaaatcga cctccagatg ctgtactgag agatgccacc   1500

tcactgaatc aggccgcgct gtaccgcctc agcggagact ggaatcctct acacattgac   1560

ccggactttg cgagcgttgc cggttttgag aagcccatat tacatggact atgtaccttt   1620

ggattttctg caaggcatgt tttacagcag tttgcagata atgatgtatc aagattcaag   1680

gcgattaagg ttcgttttgc caaaccagtg tatccaggac agactctaca aactgagatg   1740

tggaaggaag gaaacagaat tcattttcaa accaaggtcc acgagactgg agatgttgtc   1800

atttcaaatg cgtacgtgga tctcgtgcct gcatctggag tttcaaccca gacaccttca   1860

gagggtggag agctccagag tgctcttgtg tttggggaga taggccgccg cctcaagagt   1920

gttggccgtg aggtggtaaa gaaagcgaat gctgtgtttg aatggcatat cacgaaaggt   1980

gggactgttg cagccaagtg gaccattgac ctgaagagcg gctcagggga ggtgtaccaa   2040

ggccccgcaa agggctctgc tgatgtgacc atcatcattt ccgatgagga ttttatggaa   2100

gtggtcttcg gcaagcttga cccacagaag gccttcttca gtggcaggct gaaggccaga   2160

gggaacatca tgctgagcca gaaactacag atgattctta aagactatgc caagctctga   2220

agggaaccca ctgtgtgctg ttaaaggagt caataattaa atactgtcta cccagctgag   2280

ccgcagcctt ctgcgatcca caggagtgtg caggagaaat cgcttcacat ttccagattc   2340

agataacttg catattttca ttttctacta atttttcaca tatttttaca aggaactgta   2400

atctaggtag caaaataatc attctgttca tagatctgta tcttaataaa aaaaatcaac   2460

caaaaacc                                                            2468
```

<210> SEQ ID NO 41
<211> LENGTH: 60
<212> TYPE: DNA
<213> ORGANISM: Mus musculus

<400> SEQUENCE: 41

```
gcgtgccatg attctttcat ccaaacttcc cagaagcgaa tctaatcctc ttagttccat     60
```

<210> SEQ ID NO 42
<211> LENGTH: 60
<212> TYPE: DNA
<213> ORGANISM: Mus musculus

<400> SEQUENCE: 42

```
tgtcatatca ctgggtagac aggtacccat taccttagca agtatgttta gtgctcagtg     60
```

<210> SEQ ID NO 43
<211> LENGTH: 60
<212> TYPE: DNA
<213> ORGANISM: Mus musculus

<400> SEQUENCE: 43

```
cagttgtagt cacttgatac tgcattccga acttgagtct attgaatcca gaatgtgaat     60
```

<210> SEQ ID NO 44
<211> LENGTH: 60
<212> TYPE: DNA
<213> ORGANISM: Mus musculus

<400> SEQUENCE: 44

```
gactgcagcc ttggagcaaa acttaggttt tcatatgttt ttaaatatgt tgcttttgtg     60
```

<210> SEQ ID NO 45
<211> LENGTH: 60
<212> TYPE: DNA
<213> ORGANISM: Mus musculus

<400> SEQUENCE: 45
atgcacagaa taagttctcc aacatttatt attggtcagt tgatgttgct tagtgtcccc 60

<210> SEQ ID NO 46
<211> LENGTH: 60
<212> TYPE: DNA
<213> ORGANISM: Mus musculus

<400> SEQUENCE: 46
aacacagcct attttcgtga acattgaagt ttgtaacgga aagataggat ctcattttca 60

<210> SEQ ID NO 47
<211> LENGTH: 60
<212> TYPE: DNA
<213> ORGANISM: Mus musculus

<400> SEQUENCE: 47
aggctacttc cttctcctca cctacatgta ttccctgctt cttagaattg tagctcattg 60

<210> SEQ ID NO 48
<211> LENGTH: 60
<212> TYPE: DNA
<213> ORGANISM: Mus musculus

<400> SEQUENCE: 48
gtaattgaac caagtcttta ctgaatgcct ggaaaatgaa agcttaatca acttaccctg 60

<210> SEQ ID NO 49
<211> LENGTH: 60
<212> TYPE: DNA
<213> ORGANISM: Mus musculus

<400> SEQUENCE: 49
ttccgttgtg gtcatcgtgt gcggtggcaa caacattagt agccaacagc ttcaggagct 60

<210> SEQ ID NO 50
<211> LENGTH: 60
<212> TYPE: DNA
<213> ORGANISM: Mus musculus

<400> SEQUENCE: 50
agcagtagct cagtcctggg acagaagacg aggcctggat gtgaagattc ctgaggccaa 60

<210> SEQ ID NO 51
<211> LENGTH: 60
<212> TYPE: DNA
<213> ORGANISM: Mus musculus

<400> SEQUENCE: 51
atgattgaac ccttcttggg gacctggaaa ctggtctcca gtgaaaactt cgagaattac 60

<210> SEQ ID NO 52
<211> LENGTH: 60
<212> TYPE: DNA
<213> ORGANISM: Mus musculus

<400> SEQUENCE: 52
aagaaaccga agacagcgac cgagtgtgcg tcaaagccgg taccacacaa gattccgcag 60

<210> SEQ ID NO 53
<211> LENGTH: 60
<212> TYPE: DNA
<213> ORGANISM: Mus musculus

<400> SEQUENCE: 53
gcagcatgtt acagcagaaa agaaactaca gcacaactta tgactgaaaa taatgtagaa 60

<210> SEQ ID NO 54
<211> LENGTH: 60
<212> TYPE: DNA
<213> ORGANISM: Mus musculus

<400> SEQUENCE: 54
gtgacgcttg gccttaggtg tcattgttaa acaacataaa acttctcatt tatgagtaaa 60

<210> SEQ ID NO 55
<211> LENGTH: 60
<212> TYPE: DNA
<213> ORGANISM: Mus musculus

<400> SEQUENCE: 55
gagactaatt tcacatctta ttttgcagtc atttacagtg aaacaatgtt ccagctagct 60

<210> SEQ ID NO 56
<211> LENGTH: 60
<212> TYPE: DNA
<213> ORGANISM: Mus musculus

<400> SEQUENCE: 56
gtatgattca cgcaacaata ctcttatctt agtaagtcct acttcttatg tgctgatgcc 60

<210> SEQ ID NO 57
<211> LENGTH: 60
<212> TYPE: DNA
<213> ORGANISM: Mus musculus

<400> SEQUENCE: 57
agtaacccaa aagaacaaaa aattccccat ctgtactctt tcgggctcat accttcttct 60

<210> SEQ ID NO 58
<211> LENGTH: 60
<212> TYPE: DNA
<213> ORGANISM: Mus musculus

<400> SEQUENCE: 58
ggaggggctc ctcgagagaa gattggaaca gtggcagtgt tataattagt aaggtttttt 60

<210> SEQ ID NO 59
<211> LENGTH: 60
<212> TYPE: DNA
<213> ORGANISM: Mus musculus

<400> SEQUENCE: 59
acctgattcc ttcctgaggc tatagaaggt ttagctgcat taaacgagat gcttcagcag 60

<210> SEQ ID NO 60
<211> LENGTH: 60
<212> TYPE: DNA
<213> ORGANISM: Mus musculus

<400> SEQUENCE: 60
ctcgactgaa tacagaaatg gcttttcttc ttatccacga tcattctgta ttttgaagtt 60

<210> SEQ ID NO 61
<211> LENGTH: 60
<212> TYPE: DNA
<213> ORGANISM: Mus musculus

<400> SEQUENCE: 61
gtcgctttac attgcttcct agttttacag catgatgcaa atgaattttc taacttagtg 60

<210> SEQ ID NO 62
<211> LENGTH: 60
<212> TYPE: DNA
<213> ORGANISM: Mus musculus

<400> SEQUENCE: 62
ctattcctct gttctttcag atagtaatgg gagcttttac tggcttacat cattacaata 60

<210> SEQ ID NO 63
<211> LENGTH: 60
<212> TYPE: DNA
<213> ORGANISM: Mus musculus

<400> SEQUENCE: 63
gcagaactgc ttggttgtct tttcccatgt aacttaagca tagtaatata aataaagtgg 60

<210> SEQ ID NO 64
<211> LENGTH: 60
<212> TYPE: DNA
<213> ORGANISM: Mus musculus

<400> SEQUENCE: 64
cctttctcac ctggaagaca gctcctcctc gaaggtttac aaaatgtgtg atgcctttgt 60

<210> SEQ ID NO 65
<211> LENGTH: 60
<212> TYPE: DNA
<213> ORGANISM: Mus musculus

<400> SEQUENCE: 65
atgtcagatg ttgtaaaacc cagagtatgg cagtgtcttt aatgaggctg ggctcttgtc 60

<210> SEQ ID NO 66
<211> LENGTH: 60
<212> TYPE: DNA
<213> ORGANISM: Mus musculus

<400> SEQUENCE: 66
cctttgtggg aacctggaag cttgtctcca gtgaaaactt cgatgattac atgaaagaag 60

<210> SEQ ID NO 67
<211> LENGTH: 60
<212> TYPE: DNA
<213> ORGANISM: Mus musculus

<400> SEQUENCE: 67
gcttctgcta gatgaaaatt cactgaaaat tcagtcagtc acaaactgga agaattgtaa 60

<210> SEQ ID NO 68
<211> LENGTH: 60
<212> TYPE: DNA
<213> ORGANISM: Mus musculus

<400> SEQUENCE: 68
gtggacgaca tacggaaaag ctaatggcat ttaaagcaat atacccagac attgtgcgac 60

<210> SEQ ID NO 69
<211> LENGTH: 60
<212> TYPE: DNA
<213> ORGANISM: Mus musculus

<400> SEQUENCE: 69
atatattaag tctctccctc tctggagttc ttggctacag caaggccaga tatcacattg 60

<210> SEQ ID NO 70
<211> LENGTH: 60
<212> TYPE: DNA
<213> ORGANISM: Mus musculus

<400> SEQUENCE: 70
actttctggg cagagtgaat aacccccaga gtgtggtgtg aggccttgtg cctagcccat 60

<210> SEQ ID NO 71
<211> LENGTH: 60
<212> TYPE: DNA
<213> ORGANISM: Mus musculus

<400> SEQUENCE: 71
aagatgcttt gaaggacaca acaagaaatt ctttaaagct gtggaagaaa tctagacgtg 60

<210> SEQ ID NO 72
<211> LENGTH: 60
<212> TYPE: DNA
<213> ORGANISM: Mus musculus

<400> SEQUENCE: 72
tgggtgtgaa ccacacatct gtctatccaa tggactgggt agataatacc taagaacagc 60

<210> SEQ ID NO 73
<211> LENGTH: 60
<212> TYPE: DNA
<213> ORGANISM: Mus musculus

<400> SEQUENCE: 73
ttgagagctg ggcttcctgc ctcttacata caataaagag attgctaaca ctggaaaaaa 60

<210> SEQ ID NO 74
<211> LENGTH: 60
<212> TYPE: DNA
<213> ORGANISM: Mus musculus

<400> SEQUENCE: 74
tcagaacaac agtgtttagc aagtggcatc tgacaggtgt gaatattttc ctacaatgtg 60

<210> SEQ ID NO 75
<211> LENGTH: 60
<212> TYPE: DNA
<213> ORGANISM: Mus musculus

<400> SEQUENCE: 75
ccctgtatga gtggagggat agtttaaagt tttcaccatg ttatattttc ttttgagact 60

<210> SEQ ID NO 76
<211> LENGTH: 60
<212> TYPE: DNA
<213> ORGANISM: Mus musculus

<400> SEQUENCE: 76
ctggcaaggt catgtgcctt ctctgatgcc aaaacccttt atgggggtga tggagtactt 60

<210> SEQ ID NO 77
<211> LENGTH: 60
<212> TYPE: DNA
<213> ORGANISM: Mus musculus

<400> SEQUENCE: 77
tggtgaaaca caagaaaggg attgtcaacg agcagttcct gctgcagcga ctggcggacg 60

<210> SEQ ID NO 78
<211> LENGTH: 60
<212> TYPE: DNA
<213> ORGANISM: Mus musculus

<400> SEQUENCE: 78
tagctggtgc attgaggctg caactcggat ccgagaaaac atggccagtc tgcagtccag 60

<210> SEQ ID NO 79
<211> LENGTH: 60
<212> TYPE: DNA
<213> ORGANISM: Mus musculus

<400> SEQUENCE: 79
ctgcagagtt ggtaattcag aaaactcaag gtttaagtta aaagtgagtt tagactttgg 60

<210> SEQ ID NO 80
<211> LENGTH: 60
<212> TYPE: DNA
<213> ORGANISM: Mus musculus

<400> SEQUENCE: 80
ctgtcttgag aaacttcatt tatttctcat aactgcattt atttagccat ctcagtgtgc 60

<210> SEQ ID NO 81
<211> LENGTH: 60
<212> TYPE: DNA
<213> ORGANISM: Mus musculus

<400> SEQUENCE: 81
taaaagcatg cacattgaga gtatcctgga agacattctc ttgtaaacat gtgtgtggaa 60

<210> SEQ ID NO 82
<211> LENGTH: 60
<212> TYPE: DNA
<213> ORGANISM: Mus musculus

<400> SEQUENCE: 82
gattcaatgc ctgggctttc aaactcattc cttcactcca caaatatttg ctgaatgttt 60

<210> SEQ ID NO 83
<211> LENGTH: 60
<212> TYPE: DNA
<213> ORGANISM: Mus musculus

<400> SEQUENCE: 83
cctacacttt ctatgaataa caagtcattt ctggtttaca ctgtctttta gaggaaaagg 60

<210> SEQ ID NO 84
<211> LENGTH: 60
<212> TYPE: DNA
<213> ORGANISM: Mus musculus

<400> SEQUENCE: 84
atcatcattt ccgatgagga ttttatggaa gtggtcttcg gcaagcttga cccacagaag 60

```
<210> SEQ ID NO 85
<211> LENGTH: 60
<212> TYPE: DNA
<213> ORGANISM: Mus musculus

<400> SEQUENCE: 85

tttcaaacca aggtccacga gactggagat gttgtcattt caaatgcgta cgtggatctc     60


<210> SEQ ID NO 86
<211> LENGTH: 60
<212> TYPE: DNA
<213> ORGANISM: Mus musculus

<400> SEQUENCE: 86

gcaggagaaa tcgcttcaca tttccagatt cagataactt gcatattttc attttctact     60
```